US009593333B2

(12) United States Patent
Alexander et al.

(10) Patent No.: US 9,593,333 B2
(45) Date of Patent: Mar. 14, 2017

(54) MODULATION OF APOLIPOPROTEIN C-III (APOCIII) EXPRESSION IN LIPOPROTEIN LIPASE DEFICIENT (LPLD) POPULATIONS

(71) Applicant: Ionis Pharmaceuticals, Inc., Carlsbad, CA (US)

(72) Inventors: Veronica J. Alexander, San Diego, CA (US); Nicholas J. Viney, Carlsbad, CA (US); Joseph L. Witztum, San Diego, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 14/768,180

(22) PCT Filed: Feb. 14, 2014

(86) PCT No.: PCT/US2014/016546
§ 371 (c)(1),
(2) Date: Aug. 14, 2015

(87) PCT Pub. No.: WO2014/127268
PCT Pub. Date: Aug. 21, 2014

(65) Prior Publication Data
US 2015/0376614 A1  Dec. 31, 2015

Related U.S. Application Data

(60) Provisional application No. 61/764,969, filed on Feb. 14, 2013, provisional application No. 61/880,779, filed on Sep. 20, 2013.

(51) Int. Cl.
C12N 15/11 (2006.01)
C12N 15/113 (2010.01)
A61K 31/7088 (2006.01)
A61K 45/06 (2006.01)

(52) U.S. Cl.
CPC ........ *C12N 15/113* (2013.01); *A61K 31/7088* (2013.01); *A61K 45/06* (2013.01); *C12N 2310/11* (2013.01); *C12N 2310/315* (2013.01); *C12N 2310/322* (2013.01); *C12N 2310/3341* (2013.01); *C12N 2310/341* (2013.01); *C12N 2310/346* (2013.01); *C12N 2320/30* (2013.01)

(58) Field of Classification Search
None
See application file for complete search history.

(56) References Cited

U.S. PATENT DOCUMENTS

| 4,981,957 | A | 1/1991 | Lebleu et al. |
| 5,118,800 | A | 6/1992 | Smith et al. |
| 5,319,080 | A | 6/1994 | Leumann |
| 5,359,044 | A | 10/1994 | Cook et al. |
| 5,393,878 | A | 2/1995 | Leumann |
| 5,446,137 | A | 8/1995 | Maag et al. |
| 5,466,786 | A | 11/1995 | Buhr et al. |
| 5,514,785 | A | 5/1996 | Van Ness et al. |
| 5,519,134 | A | 5/1996 | Acevedo et al. |
| 5,567,811 | A | 10/1996 | Misiura et al. |
| 5,576,427 | A | 11/1996 | Cook et al. |
| 5,591,722 | A | 1/1997 | Montgomery et al. |
| 5,597,909 | A | 1/1997 | Urdea et al. |
| 5,610,300 | A | 3/1997 | Altmann et al. |
| 5,627,053 | A | 5/1997 | Usman et al. |
| 5,639,873 | A | 6/1997 | Barascut et al. |
| 5,646,265 | A | 7/1997 | McGee |
| 5,670,633 | A | 9/1997 | Cook et al. |
| 5,700,920 | A | 12/1997 | Altmann et al. |
| 5,792,847 | A | 8/1998 | Buhr et al. |
| 5,801,154 | A | 9/1998 | Baracchini et al. |
| 6,268,490 | B1 | 7/2001 | Imanishi et al. |
| 6,525,191 | B1 | 2/2003 | Ramasamy |
| 6,582,908 | B2 | 6/2003 | Fodor et al. |
| 6,600,032 | B1 | 7/2003 | Manoharan et al. |
| 6,670,461 | B1 | 12/2003 | Nielsen et al. |
| 6,673,661 | B1 | 1/2004 | Liu et al. |
| 6,770,748 | B2 | 8/2004 | Imanishi et al. |
| 6,794,499 | B2 | 9/2004 | Wengel et al. |
| 7,034,133 | B2 | 4/2006 | Wengel et al. |

(Continued)

FOREIGN PATENT DOCUMENTS

| WO | WO 99/14226 | 3/1999 |
| WO | WO 00/63364 | 10/2000 |

(Continued)

OTHER PUBLICATIONS

Sugandhan et al, Familial Chylomicronemia Syndrome, 2007, Pediatric Dermatology, vol. 24, No. 3, p. 323-325.*
"Executive Summary of the Third Report of the National Cholesterol Education Program (NCEP) Expert Panel on Detection, Evaluation, and Treatment of High Blood Cholesterol in Adults (Adult Treatment Panel III) " JAMA (2001) 285:2486-2497.
ADA "Standards of Medical Care in Diabetes—2008" Diabetes Care (2008) 31: S12-S54.
Albaek et al., "Analogues of a Locked Nucleic Acid with Three-Carbon 2′,4′-Linkages: Synthesis by Ring-Closing Metathesis and Influence of Nucleic Acid Duplex Stability" J. Org. Chem. (2006) 71:7731-7740.
Allshire, "Molecular biology. RNAi and heterochromatin—a hushed-up affair." Science (2002) 297(5588): 1818-1819.
Altmann et al., "Second Generation Antisense Oligonucleotides—Inhibitionof PKCO. and c-RAF Kinase Expression by Chimeric Oligonucleotides Incorporating 6′-SubstitutedCarbocyclic Nucleosides and 2′-O-Ethylene Glycol Substituted Ribonucleosides" Nucleosides Nucleotides (1997) 16: 917-926.

(Continued)

*Primary Examiner* — Kate Poliakova-Georgantas
(74) *Attorney, Agent, or Firm* — Ionis Pharmaceuticals, Inc. Patent Dept.

(57) ABSTRACT

Provided are methods, compounds, and compositions for reducing expression of ApoCIII mRNA and protein for treating, preventing, delaying, or ameliorating Fredrickson Type I dyslipidemia/FCS/LPLD, in a patient. Such methods, compounds, and compositions increase HDL levels and/or improving the ratio of TG to HDL and reducing plasma lipids and plasma glucose in the patient, and are useful to treat, prevent, delay, or ameliorate any one or more of pancreatitis, cardiovascular disease, metabolic disorder, and associated symptoms.

23 Claims, No Drawings

(56) References Cited

U.S. PATENT DOCUMENTS

| | | | |
|---|---|---|---|
| 7,053,207 | B2 | 5/2006 | Wengel |
| 7,399,845 | B2 | 7/2008 | Seth et al. |
| 7,598,227 | B2 | 10/2009 | Crooke et al. |
| 7,741,457 | B2 | 6/2010 | Seth et al. |
| 7,750,141 | B2 | 7/2010 | Crooke et al. |
| 8,530,439 | B2 | 9/2013 | Crooke et al. |
| 9,157,082 | B2 | 10/2015 | Mullick et al. |
| 2001/0053519 | A1 | 12/2001 | Fodor et al. |
| 2003/0228597 | A1 | 12/2003 | Cowsert et al. |
| 2004/0171570 | A1 | 9/2004 | Allerson et al. |
| 2004/0208856 | A1* | 10/2004 | Crooke ............... C12N 15/113 424/93.21 |
| 2005/0130923 | A1 | 6/2005 | Bhat et al. |
| 2007/0031844 | A1 | 2/2007 | Khvorova et al. |
| 2007/0287831 | A1 | 12/2007 | Seth et al. |
| 2008/0039618 | A1 | 2/2008 | Allerson et al. |
| 2011/0060030 | A1 | 3/2011 | Crooke et al. |
| 2012/0270929 | A1 | 10/2012 | Crooke et al. |

FOREIGN PATENT DOCUMENTS

| | | |
|---|---|---|
| WO | WO 01/49687 | 7/2001 |
| WO | WO 03/004602 | 1/2003 |
| WO | WO 2004/011624 | 2/2004 |
| WO | WO 2004/035765 | 4/2004 |
| WO | WO 2004/093783 | 11/2004 |
| WO | WO 2004/106356 | 12/2004 |
| WO | WO 2005/021570 | 3/2005 |
| WO | WO 2005/121371 | 12/2005 |
| WO | WO 2006/047842 | 5/2006 |
| WO | WO 2007/134181 | 11/2007 |
| WO | WO 2008/101157 | 8/2008 |
| WO | WO 2008/150729 | 12/2008 |
| WO | WO 2008/154401 | 12/2008 |
| WO | WO 2009/006478 | 1/2009 |
| WO | WO 2009/067647 | 5/2009 |
| WO | WO 2009/100320 | 8/2009 |
| WO | WO 2010/036696 | 4/2010 |
| WO | WO 2010/036698 | 4/2010 |
| WO | WO 2011/017521 | 5/2011 |
| WO | WO 2011/123401 | 10/2011 |
| WO | WO 2011/139702 | 11/2011 |
| WO | WO 2012/149495 | 11/2012 |
| WO | WO 2014/179626 | 11/2014 |

OTHER PUBLICATIONS

Altmann et al., "Second Generation of Antisense Oligonucleotides: From Nuclease Resistance to Biological Efficacy in Animals" Chimia (1996) 50(4): 168-176.

Altmann et al., "Second-generation antisense oligonucleotides: structure-activity relationships and the design of improved signal-transduction inhibitors." Biochem. Soc. Trans. (1996) 24: 630-637.

Altschul et al., "Basic Local Alignment Search Tool" J. Mol. Biol. (1990) 215:403-410.

Baker et al., "2'-O-(2 Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J. Biol. Chem. (1997) 272: 11944-12000.

Bickerton et al., "Preferential uptake of dietary Fatty acids in adipose tissue and muscle in the postprandial period" Diabetes (2007) 56(1):168-176.

Borghei et al., "Familial Chylomicronemia Syndrome Presenting With Acute Necrotizing Pancreatitis in a Five Month Infant" J. Nepal Paediatr. Soc. (2010) 30(2):110-112.

Braasch et al., "Locked nucleic acid (LNA): fine-tuning the recognition of DNA and RNA" Chem. Biol. (2001) 8:1-7.

Branch et al., "A good antisense molecule is hard to find," TIBS (1998) 23:45-50.

Brisson et al., "Comparison of the efficacy of fibrates on hypertriglyceridemic phenotypes with different genetic and clinical characteristics" Pharmacogenetics and Genomics (2010) 20:742-747.

Brunzell JD., "Familial Lipoprotein Lipase Deficiency" GeneReviews™, University of Washington 1993-2015 (updated Apr. 24, 2014).

Bury et al., "Immunonephelometric quantitation of the apolipoprotein C-III in human plasma" Clinica Chimica Acta. (1985) 145:249-258.

Catapano et al., "ESC/EAS Guidelines for the management of dyslipidaemias: The Task Force for the management of dyslipidaemias of the European Society of Cardiology (ESC) and the European Atherosclerosis Society (EAS)" Atherosclerosis (2011) 217S: S1-S44.

Chan et al., "An ABC of apolipoprotein C-III: a clilnically useful new chardiovascular risk factor?" Int J Clin Pract (2008) 62:799-809.

Chan et al., "Markers of triglyceride-rich lipoprotein remnant metabolism in visceral obesity" Clin. Chem. (2002) 48:278-283.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Crooke et al., "Basic Principles of Antisense Therapeutics" Antisense Research and Application (1998) Chapter 1:1-50.

Davidsson et al., "A proteomic study of the apolipoproteins in LDL subclasses in patients with the metabolic syndrome and type 2 diabetes." J. Lipid Res. (2005) 46:1999-2006.

Elayadi et al., "Application of PNA and LNA oligomers to chemotherapy" Curr. Opinion Invest. Drugs (2001) 2: 558-561.

Ferns et al., "Investigation and management of hypertriglyceridaemia." J Clin Pathol (2008) 61:1174-118.

Fredrickson et al., "A system for phenotyping hyperlipoproteinemia" Circulation (1965) 31:321-327.

Fredrickson et al., "Fat transport in lipoproteins—an integrated approach to mechanisms and disorders" N. Engl. J. Med. (1967) 276(1):34-42.

Freier et al., "The ups and downs of nucleic acid duplex stability: structure-stability studies on chemically-modified DNA:RNA duplexes" Nucleic Acids Research (1997) 25(22):4429-4443.

Frieden et al., "Expanding the design horizon of antisense oligonucleotides with alpha-L-LNA" Nucleic Acids Research (2003) 31(21):6365-6372.

Gastaldelli et al., "Assessment of methods for improving tracer estimation of non-steady-state rate of appearance" J. Appl. Physiol. (1999) 87:1813-1822.

Gaudet et al., "Efficacy and long-term safety of alipogene tiparvovec (AAV1-LPLS447X) gene therapy for lipoprotein lipase deficiency: an open-label trial" Gene Therapy (2013) 20:361-369.

Gaudet et al., "Review of the clinical development of alipogene tiparvovec gene therapy for lipoprotein lipase deficiency" Atherosclerosis Supplements 11 (2010) 55-60.

Gautschi et al. "Activity of a Novel bcl-2/bc1-xL-Bispecific Antisense Oligonucleotide Against Tumors of Diverse Histologic Origins" J. Natl. Cancer Inst. (2001) 93:463-471.

Goodman et al., "Report of the National Cholesterol Education Program Expert Panel on Detection, Evaluation, and Treatment of High Blood Cholesterol in Adults " Arch. Int. Med. (1988) 148:36-39.

Gordon et al., "High density lipoprotein as a protective factor against coronary heart disease. The Framingham Study" Am. J. Med. (1977) 62:707-714.

Gu et al. "Base Pairing Properties of D- and L-Cyclohexene Nucleic Acids (CeNA)" Oligonucleotides (2003) 13(6): 479-489.

Gu et al., "Enzymatic Resolution and Base Pairing Properties of D- and L-Cylohexenyl Nucleic Acids (CeNA)" Nucleosides, Nucleotides & Nucleic Acids (2005) 24(5-7): 993-998.

Gu et al., "Synthesis of enantiomeric-pure cyclohexenyl nucleoside building blocks for oligonucleotide synthesis" Tetrahedron (2004) 60(9): 2111-2123.

Hall et al., "Establishment and Maintenance of a Heterochromatin Domain" Science (2002) 297: 2232-2237.

Hegele et al., "A polygenic basis for four classical Fredrickson hyperlipoproteinemia phenotypes that are characterized by hypertriglyceridemia." Hum Mol Genet (2009) 18:4189-4194.

(56) References Cited

OTHER PUBLICATIONS

Hegele et al., "Hypertriglyceridemia: phenomics and genomics." Mol Cell Biochem (2009) 326:35-43.
Hertz et al., "Mode of action of peroxisome proliferators as hypolipidemic drugs. Suppression of apolipoprotein C-III" J. Biol. Chem. (1995) 270:13470-13475.
Horvath et al., "Stereoselective synthesis of (-)-ara-cyclohexenyl-adenine" Tetrahedron Letters (2007) 48: 3621-3623.
International Search Report for application PCT/US2004/010946 dated Feb. 22, 2006.
International Search Report for application PCT/US2012/035694 dated Jul. 19, 2012.
International Search Report for application PCT/US2014/016546 dated Aug. 18, 2014.
Jenuwein "An RNA-Guided Pathway for the Epigenome" Science (2002) 5590: 2215-2218.
Jones et al., "RNA quantitation by fluorescence-based solution assay: RiboGreen reagent characterization." Analytical Biochemistry (1998) 265:368-374.
Kashyap ML, "Mechanistic studies of high-density lipoproteins." Am. J. Cardiol. (1998) 82:42U-48U.
Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.
Kumar et al., "The first analogues of LNA (locked nucleic acids): phosphorothioate-LNA and 2'-thio-LNA" Bioorg Med Chem Lett. (1998) 8:2219-2222.
Lee et al., "LDL containing apolipoprotein CIII is an independent risk factor for coronary events in diabetic patients." Arterioscler Thromb Vasc Biol (2003) 23:853-858.
Leumann et al., "DNA Analogues: From Supramolecular Principles to Biological Properties" Bioorganic & Medicinal Chemistry (2002) 10:841-854.
Maher et al., "Comparative hybrid arrest by tandem antisense oligodeoxyribonucleotides or oligodeoxyribonucleoside methylphosphonates in a cell-free system" Nuc. Acid. Res. (1988) 16(8):3341-3358.
Martin, "New acces to 2'-O-alkylated ribonucleosides and properties of 2'-O-alkylated oligoribonucleotides" Helv. Chim. Acta. (1995) 78:486-504.
Mauger et al., "Apolipoprotein C-III isoforms: kinetics and relative implication in lipid metabolism." J. Lipid Res (2006) 47:1212-1218.
Mendivil et al., "Low-density lipoproteins containing apolipoprotein C-III and the risk of coronary heart disease." Circulation (2011) 124:2065-2072.
Mittendorfer et al., "What does the measurement of whole-body fatty acid rate of appearance in plasma by using a fatty acid tracer really mean?" Diabetes (2003) 52:1641-1648.
Nauwelaerts et al., "Cyclohexenyl nucleic acids: conformationally flexible oligonucleotides" Nucleic Acids Research (2005) 33(8): 2452-2463.
Nauwelaerts et al., "Structural Characterization and Biological Evaluation of Small Interfering RNAs Containing Cyclohexenyl Nucleosides" J. Am. Chem. Soc. (2007) 129(30): 9340-9348.
NCEP "Third Report of the National Cholesterol Education Program (NCEP) Expert Panel on Detection, Evaluation, and Treatment of High Blood Cholesterol in Adults (Adult Treatment Panel III) final report." Circulation (2002) 106:3143-421.
New England Biolabs 1998/99 Catalog (cover page and pp. 121 and 284).
Nordestgaard et al., "Large lipoproteins are excluded from the arterial wall in diabetic cholesterol-fed rabbits." J Lipid Res (1988) 29:1491-1500.
Nordestgaard et al., "Reduced atherogenesis in cholesterol-fed diabetic rabbits. Giant lipoproteins do not enter the arterial wall." Arteriosclerosis (1988) 8:421-428.

Normand-Lauziere et al., "Increased postprandial nonesterified fatty acid appearance and oxidation in type 2 diabetes is not fully established in offspring of diabetic subjects." PLoS One (2010) 5: e10956.
Onat et at., "Apolipoprotein C-III, a strong discriminant of coronary risk in men and a determinant of the metabolic syndrome in both genders." Atherosclerosis (2003) 168:81-89.
Ooi et al., "Apolipoprotein C-III: understanding an emerging cardiovascular risk factor" Clinical Science (2008) 114:611-624.
Orum et al., "Locked nucleic acids: A promising molecular family for gene-function analysis and antisense drug development" Curr. Opinion Mol. Ther. (2001) 3:239-243.
Pal-Bhadra et al., "Heterochromatic Silencing and HP1 Localization in *Drosophila* are Dependent on the RNAi Machinery" Science (2004) 303: 669-672.
Reynolds et al., "Rational siRNA design for RNA interference" Nature Biotechnology (2004) 22(3):326-330.
Robeyns et al., "Oligonucleotides with cyclohexene-nucleoside building blocks: crystallization and preliminary X-ray studies of a left-handed sequence GTGT ACAC" Acta Crystallographica, Section F: Structural Biology and Crystallization Communications (2005) F61(6): 585-586.
Robeyns et al., "Structure of the Fully Modified Left-Handed Cyclohexene Nucleic Acid Sequence GTGTACAC" J. Am. Chem. Soc. (2008) 130(6): 1979-1984.
Sacks et al., "VLDL, apolipoproteins B, CIII, and E, and risk of recurrent coronary events in the Cholesterol and Recurrent Events (CARE) trial." Circulation (2000) 102:1886-1892.
Sanghvi et al., "Heterocyclic Base Modifications in Nucleic Acids and Their Applications in Antisense Oligonucleotides" Antisense Research and Applications (1993) pp. 273-288.
Shachter NS, "Apolipoproteins C-I and C-III as important modulators of lipoprotein metabolism." Curr. Opin. Lipidol (2001) 12:297-304.
Singh et al., "LNA (locked nucleic acids): synthesis and high-affinity nucleic acid recognition" Chem. Commun. (1998) 455-456.
Singh et al., "Synthesis of 2'-amino-LNA: a novel conformationally restricted high-affinity oligonucleotide analogue with a handle" J. Org. Chem. (1998) 63: 10035-10039.
Smith et al., "Comparison of biosequences" Adv. Appl. Math. (1981) 2(4):482-489.
Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.
Toskes PP, "Hyperlipidemic pancreatitis" Gastroenterol Clin North Am (1990) 19:783-791.
Tremblay et al., "Etiology and risk of lactescent plasma and severe hypertriglyceridemia" Journal of Clinical Lipidology (2011) 5:37-44.
Verbeure et al., "RNase H mediated cleavage of RNA by cyclohexene nucleic acid (CeNA)" Nucleic Acids Research (2001) 29(24): 4941-4947.
Verdel et al., "RNAi-Mediated Targeting of Heterochromatin by the RITS Complex" Science (2004) 303: 672-676.
Volpe et al., "Regulation of heterochromatic silencing and histone H3 lysine-9 methylation by RNAi." Science (2002) 297(5588): 1833-1837.
Wahlestedt et al., "Potent and nontoxic antisense oligonucleotide containing locked nucleic acids" Proc. Natl. Acad. Sci. USA (2000) 97: 5633-5638.
Wang et al., "A Straightforward Stereoselective Synthesis of D- and L-5-Hydroxy-4-hydroxymethyl-2-cyclohexenylguanine" J. Org. Chem. (2001) 66: 8478-8482.
Wang et al., "Cyclohexene Nucleic Acids (CeNA) Form Stable Duplexes With RNA and Induce RNASE H Activity"Nucleosides, Nucleotides & Nucleic Acids (2001) 20(4-7) 785-788.
Wang et al., "Cyclohexene Nucleic Acids (CeNA): Serum Stable Oligonucleotides that Activate RNase H and Increase Duplex Stability with Complementary RNA" J. Am. Chem. (2000) 122: 8595-8602.
Wang et al., "Stereocontrolled Synthesis of Ara-Type Cyclohexenyl Nucleosides" J. Org. Chem. (2003) 68: 4499-4505.

(56) References Cited

OTHER PUBLICATIONS

Watts et al., "Differential regulation of lipoprotein kinetics by atorvastatin and fenofibrate in subjects with the metabolic syndrome." Diabetes (2003) 52:803-811.
Weinstock et al., "Severe Hypertriglyceridemia, Reduced High Density Lipoprotein, and Neonatal Death in Lipoprotein Lipase Knockout Mice" J. Clin. Invest. (1995) 96:2555-2568.
Weissglas-Volkov et al., "Genetic causes of high and low serum HDL-cholesterol." J Lipid Res (2010) 51:2032-2057.
Woolf et al. "Specificity of antisense oligonucleotides in vivo"PNAS (1992) 89:7305-7309.
Yuan et al., "Hypertriglyceridemia: its etiology, effects and treatment" CMAJ. (2007) 176(8):1113-1120.
Zhang et al., "PowerBLAST: A New Network BLAST Application for Interactive or Automated Sequence Analysis and Annotation" Genome Res. (1997) 7:649-656.
Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.
Search report for EP 14751357.6 dated Sep. 23, 2016.
Gaudet et al., "Targeting APOC3 in the Familial Chylomicronemia Syndrome" New England Jouranl of Medicine (2014) 371: 2200-2206.
Norata et al., "Apolipoprotein C-III: From Pathophysiology to Pharmacology" Trends in Pharmacological Sciences (2015) 36: 675-687.

\* cited by examiner

# MODULATION OF APOLIPOPROTEIN C-III (APOCIII) EXPRESSION IN LIPOPROTEIN LIPASE DEFICIENT (LPLD) POPULATIONS

CROSS REFERENCED TO RELATED APPLICATIONS

This application is a U.S. National Phase filing under 35 U.S.C. §371 claiming priority to International Serial No. PCT/US2014/016546 filed Feb. 14, 2014, which claims priority to U.S. Provisional Application No. 61/880,779, filed Sep. 20, 2013, and U.S. Provisional Application No. 61/764,969, filed Feb. 14, 2013, each of which is incorporated herein by reference in its entirety.

SEQUENCE LISTING

The present application is being filed along with a Sequence Listing in electronic format. The Sequence Listing is provided as a file entitled BIOL0218USASEQ_ST25.txt, created on Aug. 13, 2015 which is 16 Kb in size. The information in the electronic format of the sequence listing is incorporated herein by reference in its entirety.

FIELD OF THE INVENTION

Provided herein are methods, compounds, and compositions for reducing expression of Apolipoprotein C-III (ApoCIII) mRNA and protein, reducing triglyceride levels and increasing high density lipoprotein (HDL) levels or HDL activity in Fredrickson Type I dyslipidemia patients. Also, provided herein are compounds and compositions for use in treating Fredrickson Type I dyslipidemia or associated disorders thereof.

BACKGROUND

Lipoproteins are globular, micelle-like particles that consist of a non-polar core of acylglycerols and cholesteryl esters surrounded by an amphiphilic coating of protein, phospholipid and cholesterol. Lipoproteins have been classified into five broad categories on the basis of their functional and physical properties: chylomicrons, very low density lipoproteins (VLDL), intermediate density lipoproteins (IDL), low density lipoproteins (LDL), and high density lipoproteins (HDL). Chylomicrons transport dietary lipids from intestine to tissues. VLDLs, IDLs and LDLs all transport triacylglycerols and cholesterol from the liver to tissues. HDLs transport endogenous cholesterol from tissues to the liver Apolipoprotein C-III (also called APOC3, APOC-III, ApoCIII, and APO C-III) is a constituent of HDL and of triglyceride (TG)-rich lipoproteins. Elevated ApoCIII is associated with elevated TG levels and diseases such as cardiovascular disease, metabolic syndrome, obesity and diabetes (Chan et al., *Int J Clin Pract,* 2008, 62:799-809; Onat et at., *Atherosclerosis,* 2003, 168:81-89; Mendivil et al., *Circulation,* 2011, 124:2065-2072; Mauger et al., *J. Lipid Res,* 2006. 47: 1212-1218; Chan et al., *Clin. Chem,* 2002. 278-283; Ooi et al., *Clin. Sci,* 2008. 114: 611-624; Davidsson et al., *J. Lipid Res.* 2005. 46: 1999-2006; Sacks et al., *Circulation,* 2000. 102: 1886-1892; Lee et al., *Arterioscler Thromb Vasc Biol,* 2003. 23: 853-858). ApoCIII slows clearance of TG-rich lipoproteins by inhibiting lipolysis, both through inhibition of lipoprotein lipase (LPL) and by interfering with lipoprotein binding to cell-surface glycosaminoglycan matrix (Shachter, *Curr. Opin. Lipidol,* 2001, 12, 297-304). As ApoCIII inhibits LPL leading to a decrease in lipolysis of TGs, it would be unexpected that inhibition of ApoCIII would have a beneficial effect in LPL deficient (LPLD) subjects.

LPLD is characterized by the inability of affected individuals to produce functionally active LPL. LPL is mainly produced in skeletal muscle, fat tissue, and heart muscle and has multiple key functions, among which is the catabolism of TG-rich lipoproteins (e.g. VLDL) and chylomicrons (CM). Off-loading TG from CM (and VLDL) normally protects against excessive postprandial rise in CM mass and TG. In LPLD, LPL is dysfunctional and more than 12 hours after meals hyperTG and chylomicronaemia are still present and visible as lipemia.

The Fredrickson system is used to classify primary (genetic) causes of dyslipidemia such as hypertriglyceridemia in patients. Fredrickson Type I (also known as LPLD or Familial Chylomicronemia Syndrome (FCS)) is usually caused by mutations of either the LPL gene, or of the gene's cofactor ApoC-II, resulting in the inability of affected individuals to produce functionally active LPL (i.e. LPLD). Patients have mutations that are either homozygous (having the same mutation on each allele) or compound heterozygous (having different mutations on each allele). The prevalence is approximately 1 in 1,000,000 in the general population and much higher in South Africa and Eastern Quebec as a result of a founder effect.

Currently, Fredrickson Type I, FCS, LPLD, patients respond minimally, or not at all, to TG-lowering drugs such as statins, fibrates and nicotinic acid (Tremblay et al., J Clin Lipidol, 2011, 5:37-44; Brisson et al., Pharmacogenet Genom, 2010, 20:742-747). Clinical management of Fredrickson Type I, FCS, LPLD, patients generally consist of severe reduction in all dietary fat to much less than 20% of caloric intake and the use of medium-chain TG, which are absorbed via the portal system and therefore do not directly enter into plasma. Such a life-long dietary regimen presents significant compliance issues for patients. Even when patients are compliant to the diet and are tightly followed in a lipid clinic by a dietician and a medical team, TGs often do not decrease below the threshold of increased pancreatitis risk. Recently, a gene therapy product (Glybera®) has been approved in Europe for treating adult LPLD patients suffering from severe or multiple pancreatitis attacks despite dietary fat restrictions. Patients treated with Glybera® require administration of an immunosuppressive drug prior to and following Glybera® treatment. Glybera® will only be offered through dedicated centers with expertise in treating LPLD and by specially trained doctors to ensure ongoing safety of the treatment (http://www.uniqure.com/products/glybera/).

Accordingly, there is still a need to provide patients with Fredrickson Type I dyslipidemia, FCS, LPLD, novel treatment options. Antisense technology is emerging as an effective means for reducing the expression of certain gene products and may prove to be uniquely useful in a number of therapeutic, diagnostic, and research applications for the modulation of ApoCIII. We have previously disclosed compositions and method for inhibiting ApoCIII by antisense compounds in US 20040208856 (U.S. Pat. No. 7,598,227), US 20060264395 (U.S. Pat. No. 7,750,141), WO 2004/093783 and WO 2012/149495, all incorporated-by-reference herein. An antisense oligonucleotide targeting ApoCIII has been tested in a Phase I clinical trial and was shown to be safe. Currently, an antisense oligonucleotide targeting ApoCIII is in Phase II clinical trials to assess its effectiveness in the treatment of diabetes or hypertriglyceridemia.

SUMMARY OF THE INVENTION

Certain embodiments provide a method of treating, preventing, delaying or ameliorating Fredrickson Type I dyslipidemia, FCS, LPLD, comprising administering a therapeutically effective amount of a compound comprising an ApoCIII specific inhibitor to the animal. Certain embodiments provide an ApoCIII specific inhibitor for use in treating, preventing, delaying or ameliorating Fredrickson Type I dyslipidemia, FCS, LPLD.

Certain embodiments provide a method of reducing triglyceride levels in an animal with Fredrickson Type I dyslipidemia, FCS, LPLD, comprising administering a therapeutically effective amount of a compound comprising an ApoCIII specific inhibitor to the animal.

Certain embodiments provide a method of increasing HDL levels and/or improving the ratio of TG to HDL in an animal with Fredrickson Type I dyslipidemia, FCS, LPLD, comprising administering a therapeutically effective amount of a compound comprising an ApoCIII specific inhibitor to the animal.

Certain embodiments provide a method of preventing, delaying or ameliorating a cardiovascular and/or metabolic disease, disorder, condition, or symptom thereof, in an animal with Fredrickson Type I dyslipidemia, FCS, LPLD, comprising administering a therapeutically effective amount of a compound comprising an ApoCIII specific inhibitor to the animal.

Certain embodiments provide a method of preventing, delaying or ameliorating pancreatitis, or symptom thereof, in an animal with Fredrickson Type I dyslipidemia, FCS, LPLD, comprising administering a therapeutically effective amount of a compound comprising an ApoCIII specific inhibitor to the animal.

In certain embodiments, the ApoCIII specific inhibitor is a nucleic acid, peptide, antibody, small molecule or other agent capable of inhibiting the expression of ApoCIII. In certain embodiments, the nucleic acid is an antisense compound. In certain embodiments, the antisense compound is an oligonucleotide targeting ApoCIII. In certain embodiments, the oligonucleotide is a modified oligonucleotide targeting ApoCIII. In certain embodiments, the modified oligonucleotide has a nucleobase sequence comprising at least 8 contiguous nucleobases of a nucleobase sequence of SEQ ID NO: 3. In certain embodiments, the modified oligonucleotide consists of the nucleobase sequence of SEQ ID NO: 3.

Certain embodiments provide a method of reducing triglyceride levels in an animal with Fredrickson Type I dyslipidemia, FCS, LPLD, comprising administering to the animal a therapeutically effective amount of a compound comprising a modified oligonucleotide having the sequence of SEQ ID NO: 3 wherein the modified oligonucleotide comprises: a gap segment consisting of 10 linked deoxynucleosides, a 5' wing segment consisting of 5 linked nucleosides, and a 3' wing segment consisting 5 linked nucleosides; wherein the gap segment is positioned immediately adjacent to and between the 5' wing segment and the 3' wing segment, wherein each nucleoside of each wing segment comprises a 2'-O-methoxyethyl sugar, wherein each cytosine is a 5-methylcytosine, and wherein each internucleoside linkage is a phosphorothioate linkage.

Certain embodiments provide a method of increasing HDL levels and/or improving the ratio of TG to HDL in an animal with Fredrickson Type I dyslipidemia, FCS, LPLD, by administering to the animal a therapeutically effective amount of a compound comprising a modified oligonucleotide having the sequence of SEQ ID NO: 3 wherein the modified oligonucleotide comprises: a gap segment consisting of 10 linked deoxynucleosides, a 5' wing segment consisting of 5 linked nucleosides, and a 3' wing segment consisting 5 linked nucleosides; wherein the gap segment is positioned immediately adjacent to and between the 5' wing segment and the 3' wing segment, wherein each nucleoside of each wing segment comprises a 2'-O-methoxyethyl sugar, wherein each cytosine is a 5-methylcytosine, and wherein each internucleoside linkage is a phosphorothioate linkage.

Certain embodiments provide a method of preventing, delaying or ameliorating a cardiovascular and/or metabolic disease, disorder, condition, or symptom thereof, in an animal with Fredrickson Type I dyslipidemia, FCS, LPLD, by administering to the animal a therapeutically effective amount of a compound comprising a modified oligonucleotide having the sequence of SEQ ID NO: 3 wherein the modified oligonucleotide comprises: a gap segment consisting of 10 linked deoxynucleosides, a 5' wing segment consisting of 5 linked nucleosides, and a 3' wing segment consisting 5 linked nucleosides; wherein the gap segment is positioned immediately adjacent to and between the 5' wing segment and the 3' wing segment, wherein each nucleoside of each wing segment comprises a 2'-O-methoxyethyl sugar, wherein each cytosine is a 5-methylcytosine, and wherein each internucleoside linkage is a phosphorothioate linkage.

Certain embodiments provide a method of preventing, delaying or ameliorating pancreatitis or symptom thereof, in an animal with Fredrickson Type I dyslipidemia, FCS, LPLD, by administering to the animal a therapeutically effective amount of a compound comprising a modified oligonucleotide having the sequence of SEQ ID NO: 3 wherein the modified oligonucleotide comprises: a gap segment consisting of 10 linked deoxynucleosides, a 5' wing segment consisting of 5 linked nucleosides, and a 3' wing segment consisting 5 linked nucleosides; wherein the gap segment is positioned immediately adjacent to and between the 5' wing segment and the 3' wing segment, wherein each nucleoside of each wing segment comprises a 2'-O-methoxyethyl sugar, wherein each cytosine is a 5-methylcytosine, and wherein each internucleoside linkage is a phosphorothioate linkage.

In certain embodiments, the ApoCIII specific inhibitor is a nucleic acid, peptide, antibody, small molecule or other agent capable of inhibiting the expression of ApoCIII. In certain embodiments, the nucleic acid is an antisense compound targeting ApoCIII. In certain embodiments, the antisense compound is an antisense oligonucleotide. In certain embodiments, the antisense oligonucleotide is a modified oligonucleotide. In certain embodiments, the modified oligonucleotide has a nucleobase sequence comprising at least 8 contiguous nucleobases of ISIS 304801, AGCTTCTTGTCCAGCTTTAT (SEQ ID NO: 3). In certain embodiments, the modified oligonucleotide is at least 70%, at least 75%, at least 80%, at least 85%, at least 90%, at least 95%, at least 98% or at least 100% complementary to SEQ ID NO: 1, SEQ ID NO: 2 or SEQ ID NO: 4.

DETAILED DESCRIPTION OF THE INVENTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference for the portions of the document discussed herein, as well as in their entirety.

DEFINITIONS

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Where permitted, all patents, applications, published applications and other publications, GENBANK Accession Numbers and associated sequence information obtainable through databases such as National Center for Biotechnology Information (NCBI) and other data referred to throughout in the disclosure herein are incorporated by reference for the portions of the document discussed herein, as well as in their entirety.

Unless otherwise indicated, the following terms have the following meanings:

"2'-O-methoxyethyl" (also 2'-MOE, 2'-O(CH$_2$)$_2$—OCH$_3$ and 2'-O-(2-methoxyethyl)) refers to an O-methoxy-ethyl modification of the 2' position of a furosyl ring. A 2'-O-methoxyethyl modified sugar is a modified sugar.

"2'-O-methoxyethyl nucleotide" means a nucleotide comprising a 2'-O-methoxyethyl modified sugar moiety.

"3' target site" refers to the nucleotide of a target nucleic acid which is complementary to the 3'-most nucleotide of a particular antisense compound.

"5' target site" refers to the nucleotide of a target nucleic acid which is complementary to the 5'-most nucleotide of a particular antisense compound.

"5-methylcytosine" means a cytosine modified with a methyl group attached to the 5 position. A 5-methylcytosine is a modified nucleobase.

"About" means within ±10% of a value. For example, if it is stated, "a marker may be increased by about 50%", it is implied that the marker may be increased between 45%-55%.

"Active pharmaceutical agent" means the substance or substances in a pharmaceutical composition that provide a therapeutic benefit when administered to an individual. For example, in certain embodiments an antisense oligonucleotide targeted to ApoCIII is an active pharmaceutical agent.

"Active target region" or "target region" means a region to which one or more active antisense compounds is targeted. "Active antisense compounds" means antisense compounds that reduce target nucleic acid levels or protein levels.

"Administered concomitantly" refers to the co-administration of two agents in any manner in which the pharmacological effects of both are manifest in the patient at the same time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

"Administering" means providing a pharmaceutical agent to an individual, and includes, but is not limited to administering by a medical professional and self-administering.

"Agent" means an active substance that can provide a therapeutic benefit when administered to an animal. "First Agent" means a therapeutic compound of the invention. For example, a first agent can be an antisense oligonucleotide targeting ApoCIII. "Second agent" means a second therapeutic compound of the invention (e.g. a second antisense oligonucleotide targeting ApoCIII) and/or a non-ApoCIII therapeutic compound.

"Amelioration" refers to a lessening of at least one indicator, sign, or symptom of an associated disease, disorder, or condition. The severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding. Examples of antisense compounds include single-stranded and double-stranded compounds, such as, antisense oligonucleotides, siRNAs, shRNAs, ssRNAi and occupancy-based compounds.

"Antisense inhibition" means the reduction of target nucleic acid levels or target protein levels in the presence of an antisense compound complementary to a target nucleic acid compared to target nucleic acid levels or target protein levels in the absence of the antisense compound.

"Antisense oligonucleotide" means a single-stranded oligonucleotide having a nucleobase sequence that permits hybridization to a corresponding region or segment of a target nucleic acid. As used herein, the term "antisense oligonucleotide" encompasses pharmaceutically acceptable derivatives of the compounds described herein.

"ApoA5", "Apolipoprotein A-V" or "ApoA-V" means any nucleic acid or protein sequence encoding ApoA5.

"ApoCII", "Apolipoprotein C-II" or "ApoC2" means any nucleic acid or protein sequence encoding ApoCII. The ApoCII protein is a component of chylomicrons and VLDL particles and activates LPL to hydrolyze TGs.

"ApoCIII", "Apolipoprotein C-III" or "ApoC3" means any nucleic acid or protein sequence encoding ApoCIII. For example, in certain embodiments, an ApoCIII includes a DNA sequence encoding ApoCIII, a RNA sequence transcribed from DNA encoding ApoCIII (including genomic DNA comprising introns and exons), a mRNA sequence encoding ApoCIII, or a peptide sequence encoding ApoCIII.

"ApoCIII specific inhibitor" refers to any agent capable of specifically inhibiting the expression of ApoCIII mRNA and/or the expression or activity of ApoCIII protein at the molecular level. For example, ApoCIII specific inhibitors include nucleic acids (including antisense compounds), peptides, antibodies, small molecules, and other agents capable of inhibiting the expression of ApoCIII mRNA and/or ApoCIII protein. In certain embodiments, the nucleic acid is an antisense compound. In certain embodiments, the antisense compound is a an oligonucleotide targeting ApoCIII. In certain embodiments, the oligonucleotide targeting ApoCIII is a modified oligonucleotide targeting ApoCIII. In certain embodiments, the oligonucleotide targeting ApoCIII has a sequence as shown in SEQ ID NO: 3 or another sequence, for example, such as those disclosed in U.S. Pat. No. 7,598,227, U.S. Pat. No. 7,750,141, PCT Publication WO 2004/093783 or WO 2012/149495, all incorporated-by-reference herein. In certain embodiments, by specifically modulating ApoCIII mRNA level and/or ApoCIII protein expression, ApoCIII specific inhibitors may affect components of the lipogenic pathway. Similarly, in certain embodiments, ApoCIII specific inhibitors may affect other molecular processes in an animal.

"ApoCIII mRNA" means a mRNA encoding an ApoCIII protein.

"ApoCIII protein" means any protein sequence encoding ApoCIII.

"Atherosclerosis" means a hardening of the arteries affecting large and medium-sized arteries and is characterized by the presence of fatty deposits. The fatty deposits are called "atheromas" or "plaques," which consist mainly of cholesterol and other fats, calcium and scar tissue, and damage the lining of arteries.

"Bicyclic sugar" means a furosyl ring modified by the bridging of two non-geminal ring atoms. A bicyclic sugar is a modified sugar.

"Bicyclic nucleic acid" or "BNA" refers to a nucleoside or nucleotide wherein the furanose portion of the nucleoside or nucleotide includes a bridge connecting two carbon atoms on the furanose ring, thereby forming a bicyclic ring system.

"Cap structure" or "terminal cap moiety" means chemical modifications, which have been incorporated at either terminus of an antisense compound.

"Cardiovascular disease" or "cardiovascular disorder" refers to a group of conditions related to the heart, blood vessels, or the circulation. Examples of cardiovascular diseases include, but are not limited to, aneurysm, angina, arrhythmia, atherosclerosis, cerebrovascular disease (stroke), coronary heart disease, hypertension, dyslipidemia, hyperlipidemia, hypertriglyceridemia and hypercholesterolemia.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-O-methoxyethyl modifications.

"Chimeric antisense compound" means an antisense compound that has at least two chemically distinct regions.

"Cholesterol" is a sterol molecule found in the cell membranes of all animal tissues. Cholesterol must be transported in an animal's blood plasma by lipoproteins including very low density lipoprotein (VLDL), intermediate density lipoprotein (IDL), low density lipoprotein (LDL), and high density lipoprotein (HDL). "Plasma cholesterol" refers to the sum of all lipoproteins (VDL, IDL, LDL, HDL) esterified and/or non-esterified cholesterol present in the plasma or serum.

"Cholesterol absorption inhibitor" means an agent that inhibits the absorption of exogenous cholesterol obtained from diet.

"Co-administration" means administration of two or more agents to an individual. The two or more agents can be in a single pharmaceutical composition, or can be in separate pharmaceutical compositions. Each of the two or more agents can be administered through the same or different routes of administration. Co-administration encompasses parallel or sequential administration.

"Complementarity" means the capacity for pairing between nucleobases of a first nucleic acid and a second nucleic acid. In certain embodiments, complementarity between the first and second nucleic acid can be between two DNA strands, between two RNA strands, or between a DNA and an RNA strand. In certain embodiments, some of the nucleobases on one strand are matched to a complementary hydrogen bonding base on the other strand. In certain embodiments, all of the nucleobases on one strand are matched to a complementary hydrogen bonding base on the other strand. In certain embodiments, a first nucleic acid is an antisense compound and a second nucleic acid is a target nucleic acid. In certain such embodiments, an antisense oligonucleotide is a first nucleic acid and a target nucleic acid is a second nucleic acid.

"Contiguous nucleobases" means nucleobases immediately adjacent to each other.

"Constrained ethyl" or "cEt" refers to a bicyclic nucleoside having a furanosyl sugar that comprises a methyl (methyleneoxy) (4'-CH(CH$_3$)—O-2') bridge between the 4' and the 2' carbon atoms.

"Cross-reactive" means an oligomeric compound targeting one nucleic acid sequence can hybridize to a different nucleic acid sequence. For example, in some instances an antisense oligonucleotide targeting human ApoCIII can cross-react with a murine ApoCIII. Whether an oligomeric compound cross-reacts with a nucleic acid sequence other than its designated target depends on the degree of complementarity the compound has with the non-target nucleic acid sequence. The higher the complementarity between the oligomeric compound and the non-target nucleic acid, the more likely the oligomeric compound will cross-react with the nucleic acid.

"Cure" means a method that restores health or a prescribed treatment for an illness.

"Coronary heart disease (CHD)" means a narrowing of the small blood vessels that supply blood and oxygen to the heart, which is often a result of atherosclerosis.

"Deoxyribonucleotide" means a nucleotide having a hydrogen at the 2' position of the sugar portion of the nucleotide. Deoxyribonucleotides may be modified with any of a variety of substituents.

"Diabetes mellitus" or "diabetes" is a syndrome characterized by disordered metabolism and abnormally high blood sugar (hyperglycemia) resulting from insufficient levels of insulin or reduced insulin sensitivity. The characteristic symptoms are excessive urine production (polyuria) due to high blood glucose levels, excessive thirst and increased fluid intake (polydipsia) attempting to compensate for increased urination, blurred vision due to high blood glucose effects on the eye's optics, unexplained weight loss, and lethargy.

"Diabetic dyslipidemia" or "type 2 diabetes with dyslipidemia" means a condition characterized by Type 2 diabetes, reduced HDL-C, elevated triglycerides, and elevated small, dense LDL particles.

"Diluent" means an ingredient in a composition that lacks pharmacological activity, but is pharmaceutically necessary or desirable. For example, the diluent in an injected composition may be a liquid, e.g. saline solution.

"Dyslipidemia" refers to a disorder of lipid and/or lipoprotein metabolism, including lipid and/or lipoprotein overproduction or deficiency. Dyslipidemias may be manifested by elevation of lipids such as chylomicron, cholesterol and triglycerides as well as lipoproteins such as low-density lipoprotein (LDL) cholesterol. An example of a dyslipidemia is chylomicronemia or hypertriglyceridemia.

"Dosage unit" means a form in which a pharmaceutical agent is provided, e.g. pill, tablet, or other dosage unit known in the art. In certain embodiments, a dosage unit is a vial containing lyophilized antisense oligonucleotide. In certain embodiments, a dosage unit is a vial containing reconstituted antisense oligonucleotide.

"Dose" means a specified quantity of a pharmaceutical agent provided in a single administration, or in a specified time period. In certain embodiments, a dose can be administered in one, two, or more boluses, tablets, or injections. For example, in certain embodiments where subcutaneous administration is desired, the desired dose requires a volume not easily accommodated by a single injection, therefore, two or more injections can be used to achieve the desired dose. In certain embodiments, the pharmaceutical agent is administered by infusion over an extended period of time or continuously. Doses can be stated as the amount of pharmaceutical agent per hour, day, week, or month. Doses can also be stated as mg/kg or g/kg.

"Effective amount" or "therapeutically effective amount" means the amount of active pharmaceutical agent sufficient to effectuate a desired physiological outcome in an individual in need of the agent. The effective amount can vary among individuals depending on the health and physical condition of the individual to be treated, the taxonomic group of the individuals to be treated, the formulation of the composition, assessment of the individual's medical condition, and other relevant factors.

"Fibrates" are agonists of peroxisome proliferator-activated receptor-α (PPAR-α), acting via transcription factors regulating various steps in lipid and lipoprotein metabolism. By interacting with PPAR-α, fibrates recruit different cofactors and regulate gene expression. As a consequence, fibrates are effective in lowering fasting TG levels as well as post-prandial TG and TRL remnant particles. Fibrates also have modest LDL-C lowering and HDL-C raising effects. Reduction in the expression and levels of ApoC-III is a consistent effect of PPAR-α agonists (Hertz et al. *J Biol Chem*, 1995, 270(22):13470-13475). A 36% reduction in plasma ApoC-III levels was reported with fenofibrate treatment in the metabolic syndrome (Watts et al. *Diabetes*, 2003, 52:803-811). However, fibrates have been ineffective in treating LPLD subjects with hypertriglyceridemia.

The "Fredrickson" system is used to classify primary (genetic) causes of dyslipidemia into several subgroups or types. Dyslipidemia types that may be amenable to therapy with the compounds disclosed herein include, but are not limited to, Fredrickson Type I, FCS, LPLD.

"Fredrickson Type I" is also known as "Lipoprotein lipase deficiency", "LPLD", "Familial Chylomicronemia Syndrome" or "FCS" and exists in several forms: Type Ia (also known as Buerger-Gruestz syndrome) is a lipoprotein lipase deficiency commonly due to a deficiency of LPL or altered ApoC-II; Type Ib (also known as familial apoprotein CII deficiency) is a condition caused by lack of lipoprotein lipase activator apoprotein C-II; and Type Ic is a chylomicronemia due to circulating inhibitor of lipoprotein lipase. Type I is a rare disorder that usually presents in childhood. It is characterized by severe elevations in chylomicrons and extremely elevated TG levels (always reaching well above 1000 mg/dL and not infrequently rising as high as 10,000 mg/dL or more) with episodes of abdominal pain, recurrent acute pancreatitis, eruptive cutaneous xanthomata, and hepatosplenomegaly. Patients rarely develop atherosclerosis, perhaps because their plasma lipoprotein particles are too large to enter into the arterial intima (Nordestgaard et al., J Lipid Res, 1988, 29:1491-1500; Nordestgaard et al., Arteriosclerosis, 1988, 8:421-428). Type I is usually caused by mutations of either the LPL gene, or of the gene's cofactor ApoC-II, resulting in the inability of affected individuals to produce sufficient functionally active LPL. Patients are either homozygous for such mutations or compound heterozygous. Fredrickson Type I can also be due to mutations in the GPIHBP1, APOA5, LMF1 or other genes leading to dysfunctional LPL. Brunzell, In: Pagon R A, Adam M P, Bird T D, Dolan C R, Fong C T, Stephens K, editors. GeneReviews™ [Internet]. Seattle (Wash.): University of Washington, Seattle; 1993-2013. 1999 Oct. 12 [updated 2011 Dec. 15]. Further, Fredrickson Type I, in some instances, can be due to the presence of LPL inhibitors (e.g., anti-LPL antibodies) in an individual causing dysfunctional LPL. The prevalence of Fredrickson Type I is approximately 1 in 1,000,000 in the general population and much higher in South Africa and Eastern Quebec as a result of a founder effect. Patients respond minimally, or not at all, to TG-lowering drugs (Tremblay et al., J Clin Lipidol, 2011, 5:37-44; Brisson et al., Pharmacogenet Genom, 2010, 20:742-747) and hence restriction of dietary fat to 20 grams/day or less is used to manage the symptoms of this rare disorder.

"Fredrickson Type II" is the most common form of primary hyperlipidemia. It is further classified into Type IIa and Type IIb, depending mainly on whether there is elevation in VLDL in addition to LDL cholesterol (LDL-C). Type IIa (familial hypercholesterolemia) may be sporadic (due to dietary factors), polygenic, or truly familial as a result of a mutation in either the LDL receptor gene on chromosome 19 (0.2% of the population) or the apolipoprotein B (apoB) gene (0.2%). The familial form is characterized by tendon xanthoma, xanthelasma and premature cardiovascular disease. The incidence of this disease is about 1 in 500 for heterozygotes, and 1 in 1,000,000 for homozygotes. Type IIb (also known as familial combined hyperlipoproteinemia) is a mixed hyperlipidemia (high cholesterol and TG levels), caused by elevations in LDL-C and in VLDL. The high VLDL levels are due to overproduction of substrates, including TG, acetyl CoA, and an increase in B-100 synthesis. They may also be caused by the decreased clearance of LDL. Prevalence in the population is about 10%.

"Fredrickson Type III" (also known as dysbetalipoproteinemia) is a remnant removal disease, or broad-beta disease (Fern et al., *J Clin Pathol*, 2008, 61:1174-118). It is due to cholesterol-rich VLDL (β-VLDL). Typically, patients with this condition have elevated plasma cholesterol and TG levels because of impaired clearance of chylomicron and VLDL remnants (e.g. IDL). The impaired clearance is due to a defect in apolipoprotein E (apoE). Normally functioning apoE contained on the remnants would enable binding to the LDL receptor and removal from the circulation. Accumulation of the remnants in affected individuals can result in xanthomatosis and premature coronary and/or peripheral vascular disease. The most common cause for Type III is the presence of apoE E2/E2 genotype. Its prevalence has been estimated to be approximately 1 in 10,000.

"Fredrickson Type IV" (also known as familial hypertriglyceridemia) is an autosomal dominant condition occurring in approximately 1% of the population. TG levels are elevated as a result of excess hepatic production of VLDL or heterozygous LPL deficiency, but are almost always less than 1000 mg/dL. Serum cholesterol levels are usually within normal limits. The disorder is heterogeneous and the phenotype strongly influenced by environmental factors, particularly carbohydrate and ethanol consumption.

"Fredrickson Type V" has high VLDL and chylomicrons. It is characterized by carriers of loss-of-function LPL gene variants associated with LPL activity of at least 20% (i.e. partial LPL deficiency as compared to Fredrickson Type I). These patients present with lactescent plasma and severe hypertriglyceridemia because of chylomicrons and VLDL. TG levels are invariably greater than 1000 mg/dL and total cholesterol levels are always elevated. The LDL-C level is usually low. It is also associated with increased risk for acute pancreatitis, glucose intolerance and hyperuricemia. Symptoms generally present in adulthood (>35 years) and, although the prevalence is relatively rare, it is much more common than homozygous or compound heterozygous LPL deficient patients.

"Fully complementary" or "100% complementary" means each nucleobase of a nucleobase sequence of a first nucleic acid has a complementary nucleobase in a second nucleobase sequence of a second nucleic acid. In certain embodiments, a first nucleic acid is an antisense compound and a second nucleic acid is a target nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as a "gap" or "gap segment" and the external regions may be referred to as "wings" or "wing segments."

"Gap-widened" means a chimeric antisense compound having a gap segment of 12 or more contiguous 2'-deoxyribonucleosides positioned between and immediately adjacent to 5' and 3' wing segments having from one to six nucleosides.

"Genetic screening" means to screen for genotypic variations or mutations in an animal. In some instances the mutation can lead to a phenotypic change in the animal. In certain instances the phenotypic change is, or leads to, a disease, disorder or condition in the animal. For example, mutations in the LPL or ApoC-II genes can lead to Fredrickson Type I dyslipidemia, FCS, LPLD. Genetic screening can be done by any of the art known techniques, for example, sequencing of the LPL or ApoC-II gene or mRNA to detect mutations. The sequence of the animal being screened is compared to the sequence of a normal animal to determine whether there is any mutation in the sequence. Alternatively, for example, identification of mutations in the LPL or ApoC-II gene or mRNA can be performed using PCR amplification and gel or chip analysis.

"Glucose" is a monosaccharide used by cells as a source of energy and inflammatory intermediate. "Plasma glucose" refers to glucose present in the plasma.

"High density lipoprotein" or "HDL" refers to a macromolecular complex of lipids (cholesterol, triglycerides and phospholipids) and proteins (apolipoproteins (apo) and enzymes). The surface of HDL contains chiefly apolipoproteins A, C and E. The function of some of these apoproteins is to direct HDL from the peripheral tissues to the liver. Serum HDL levels can be affected by underlying genetic causes (Weissglas-Volkov and Pajukanta, *J Lipid Res*, 2010, 51:2032-2057). Epidemiological studies have indicated that increased levels of HDL protect against cardiovascular disease or coronary heart disease (Gordon et al., Am. J. Med. 1977. 62: 707-714). These effects of HDL are independent of triglyceride and LDL concentrations. In clinical practice, a low plasma HDL is more commonly associated with other disorders that increase plasma triglycerides, for example, central obesity, insulin resistance, type 2 diabetes mellitus and renal disease (chronic renal failure or nephrotic proteinuria) (Kashyap. Am. J. Cardiol. 1998. 82: 42U-48U).

"High density lipoprotein-Cholesterol" or "HDL-C" means cholesterol associated with high density lipoprotein particles. Concentration of HDL-C in serum (or plasma) is typically quantified in mg/dL or nmol/L. "HDL-C" and "plasma HDL-C" mean HDL-C in serum and plasma, respectively.

"HMG-CoA reductase inhibitor" means an agent that acts through the inhibition of the enzyme HMG-CoA reductase, such as atorvastatin, rosuvastatin, fluvastatin, lovastatin, pravastatin, and simvastatin.

"Hybridization" means the annealing of complementary nucleic acid molecules. In certain embodiments, complementary nucleic acid molecules include an antisense compound and a target nucleic acid.

"Hypercholesterolemia" means a condition characterized by elevated cholesterol or circulating (plasma) cholesterol, LDL-cholesterol and VLDL-cholesterol, as per the guidelines of the Expert Panel Report of the National Cholesterol Educational Program (NCEP) of Detection, Evaluation of Treatment of high cholesterol in adults (see, Arch. Int. Med. (1988) 148, 36-39).

"Hyperlipidemia" or "hyperlipemia" is a condition characterized by elevated serum lipids or circulating (plasma) lipids. This condition manifests an abnormally high concentration of fats. The lipid fractions in the circulating blood are cholesterol, low density lipoproteins, very low density lipoproteins, chylomicrons and triglycerides. The Fredrickson classification of hyperlipidemias is based on the pattern of TG and cholesterol-rich lipoprotein particles, as measured by electrophoresis or ultracentrifugation and is commonly used to characterize primary causes of hyperlipidemias such as hypertriglyceridemia (Fredrickson and Lee, Circulation, 1965, 31:321-327; Fredrickson et al., New Eng J Med, 1967, 276 (1): 34-42).

"Hypertriglyceridemia" means a condition characterized by elevated triglyceride levels. Hypertriglyceridemia is the consequence of increased production and/or reduced or delayed catabolism of triglyceride (TG)-rich lipoproteins: VLDL and, to a lesser extent, chylomicrons (CM). Its etiology includes primary (i.e. genetic causes) and secondary (other underlying causes such as diabetes, metabolic syndrome/insulin resistance, obesity, physical inactivity, cigarette smoking, excess alcohol and a diet very high in carbohydrates) factors or, most often, a combination of both (Yuan et al. *CMAJ*, 2007, 176:1113-1120). Hypertriglyceridemia is a common clinical trait associated with an increased risk of cardiometabolic disease (Hegele et al. 2009, Hum Mol Genet, 18: 4189-4194; Hegele and Pollex 2009, Mol Cell Biochem, 326: 35-43) as well as of occurrence of acute pancreatitis in the most severe forms (Toskes 1990, Gastroenterol Clin North Am, 19: 783-791; Gaudet et al. 2010, Atherosclerosis Supplements, 11: 55-60; Catapano et al. 2011, Atherosclerosis, 217S: S1-S44; Tremblay et al. 2011, J Clin Lipidol, 5: 37-44). Examples of cardiometabolic disease include, but are not limited to, diabetes, metabolic syndrome/insulin resistance, and genetic disorders such as familial chylomicronemia syndrome (FCS), familial combined hyperlipidemia and familial hypertriglyceridemia. Borderline high TG levels (150-199 mg/dL) are commonly found in the general population and are a common component of the metabolic syndrome/insulin resistance states. The same is true for high TG levels (200-499 mg/dL) except that as plasma TG levels increase, underlying genetic factors play an increasingly important etiologic role. Very high TG levels (≥500 mg/dL) are most often associated with elevated CM levels as well, and are accompanied by increasing risk for acute pancreatitis. The risk of pancreatitis is considered clinically significant if TG levels exceed 880 mg/dL (>10 mmol) and the European Atherosclerosis Society/European Society of Cardiology (EAS/ESC) 2011 guidelines state that actions to prevent acute pancreatitis are mandatory (Catapano et al. 2011, Atherosclerosis, 217S: S1-S44). According to the EAS/ESC 2011 guidelines, hypertriglyceridemia is the cause of approximately 10% of all cases of pancreatitis, and development of pancreatitis can occur at TG levels between 440-880 mg/dL. Based on evidence from clinical studies demonstrating that elevated TG levels are an independent risk factor for atherosclerotic CVD, the guidelines from both the National Cholesterol Education Program Adult Treatment Panel III (NCEP 2002, Circulation, 106: 3143-421) and the American Diabetes Association (ADA 2008, Diabetes Care, 31: S12-S54.) recommend a target TG level of less than 150 mg/dL to reduce cardiovascular risk.

"Identifying" or "diagnosing" an animal with a named disease, disorder or condition means identifying, by art known methods, a subject prone to, or having, the named disease, disorder or condition.

"Identifying" or "diagnosing" an animal with Fredrickson Type 1 dyslipidemia means to identify a subject prone to, or having, Fredrickson Type I (a, b or c) dyslipidemia, FCS, LPLD. Identification of subjects with Fredrickson Type I, FCS, LPLD, can done by an examination of the subject's medical history in conjunction with any art known screening technique e.g., genetic screening or screening for LPL inhibitors. For example, a patient with a documented medical history of fasting TG above 750 mg/dL is then screened for mutations in the LPL gene or genes affecting the LPL such as ApoC2, ApoA5, GPIHBP1 or LMF1.

"Identifying" or "diagnosing" an animal with metabolic or cardiovascular disease means identifying a subject prone to, or having, a metabolic disease, a cardiovascular disease, or a metabolic syndrome; or, identifying a subject having any symptom of a metabolic disease, cardiovascular disease, or metabolic syndrome including, but not limited to, hypercholesterolemia, hyperglycemia, hyperlipidemia, hypertriglyceridemia, hypertension increased insulin resistance, decreased insulin sensitivity, above normal body weight, and/or above normal body fat content or any combination thereof. Such identification can be accomplished by any method, including but not limited to, standard clinical tests or assessments, such as measuring serum or circulating (plasma) cholesterol, measuring serum or circulating (plasma) blood-glucose, measuring serum or circulating (plasma) triglycerides, measuring blood-pressure, measuring body fat content, measuring body weight, and the like.

"Improved cardiovascular outcome" means a reduction in the occurrence of adverse cardiovascular events, or the risk thereof. Examples of adverse cardiovascular events include, without limitation, death, reinfarction, stroke, cardiogenic shock, pulmonary edema, cardiac arrest, and atrial dysrhythmia.

"Immediately adjacent" means there are no intervening elements between the immediately adjacent elements, for example, between regions, segments, nucleotides and/or nucleosides.

"Increasing HDL" or "raising HDL" means increasing the level of HDL in an animal after administration of at least one compound of the invention, compared to the HDL level in an animal not administered any compound.

"Individual" or "subject" or "animal" means a human or non-human animal selected for treatment or therapy.

"Induce", "inhibit", "potentiate", "elevate", "increase", "decrease", "reduce" or the like denote quantitative differences between two states. For example, "an amount effective to inhibit the activity or expression of ApoCIII" means that the level of activity or expression of ApoCIII in a treated sample will differ from the level of ApoCIII activity or expression in an untreated sample. Such terms are applied to, for example, levels of expression, and levels of activity.

"Inhibiting the expression or activity" refers to a reduction or blockade of the expression or activity of a RNA or protein and does not necessarily indicate a total elimination of expression or activity.

"Insulin resistance" is defined as the condition in which normal amounts of insulin are inadequate to produce a normal insulin response from fat, muscle and liver cells. Insulin resistance in fat cells results in hydrolysis of stored triglycerides, which elevates free fatty acids in the blood plasma. Insulin resistance in muscle reduces glucose uptake whereas insulin resistance in liver reduces glucose storage, with both effects serving to elevate blood glucose. High plasma levels of insulin and glucose due to insulin resistance often leads to metabolic syndrome and type 2 diabetes.

"Insulin sensitivity" is a measure of how effectively an individual processes glucose. An individual having high insulin sensitivity effectively processes glucose whereas an individual with low insulin sensitivity does not effectively process glucose.

"Internucleoside linkage" refers to the chemical bond between nucleosides.

"Intravenous administration" means administration into a vein.

"Linked nucleosides" means adjacent nucleosides which are bonded together.

"Lipid-lowering" means a reduction in one or more lipids in a subject. "Lipid-raising" means an increase in a lipid (e.g., HDL) in a subject. Lipid-lowering or lipid-raising can occur with one or more doses over time.

"Lipid-lowering therapy" or "lipid lowering agent" means a therapeutic regimen provided to a subject to reduce one or more lipids in a subject. In certain embodiments, a lipid-lowering therapy is provided to reduce one or more of CETP, ApoB, total cholesterol, LDL-C, VLDL-C, IDL-C, non-HDL-C, triglycerides, small dense LDL particles, and Lp(a) in a subject. Examples of lipid-lowering therapy include statins, fibrates, MTP inhibitors.

"Lipoprotein", such as VLDL, LDL and HDL, refers to a group of proteins found in the serum, plasma and lymph and are important for lipid transport. The chemical composition of each lipoprotein differs in that the HDL has a higher proportion of protein versus lipid, whereas the VLDL has a lower proportion of protein versus lipid.

"Lipoprotein Lipase" or "LPL" refers to an enzyme that hydrolyzes TGs found in lipoproteins, such as CM or VLDL, into free fatty acids and monoacylglycerols. LPL requires apo C-II as a cofactor to function in hydrolyzing TGs. LPL is mainly produced in skeletal muscle, fat tissue, and heart muscle. Hydrolysis and removal of TG from CM and VLDL normally protects against excessive postprandial rise in CM mass and TG.

"Lipoprotein lipase deficient", "lipoprotein lipase deficiency", "LPL deficiency" or "LPLD" is also known as "Fredrickson's Type I dyslipidemia", "chylomicronemia", "Familial Chylomicronemia Syndrome" or "FCS". Although subjects with LPLD generally lack LPL or LPL activity necessary for effective breakdown of fatty acids such as TGs, these subjects may still have a minimal LPL activity or express a minimal level of LPL. In some instances, a LPLD subject may express LPL or have LPL activity up to about, or no more than, 20%, 19%, 18%, 17%, 16%, 15%, 14%, 13%, 12%, 11%, 10%, 9%, 8%, 7%, 6%, 5%, 4%, 3%, 2% or 1% activity. In other instances, the LPLD subject has no measurable LPL or LPL activity. One embodiment of LPLD encompasses subjects with "hyperlipoproteinemia type Ia" (also known as "Fredrickson's Type Ia") and refers to the inability of the subjects to produce sufficient functional lipoprotein lipase enzymes necessary for effective breakdown of fatty acids such as TGs. The inability to breakdown TGs leads to hypertriglyceridemia in the subject and, often more than 12 hours after meals, hyperTG and chylomicronemia are still present and visible as lipemia. Type Ia is commonly caused by one or more mutations in the LPL gene. As disclosed herein, LPLD also encompasses subjects that have dysfunctional lipoprotein lipase such as those subjects with "hyperlipoproteinemia type Ib" (also known as "Fredrickson's Type Ib") and "hyperlipoproteinemia type Ic" (also known as "Fredrickson's Type Ic"). Type Ib is caused by lack of lipoprotein lipase activator apoprotein C-II. Type Ic is due to a circulating inhibitor of lipoprotein lipase. As with Type 1a, Type 1b/1c subjects suffer from an inability to breakdown TGs leading to hypertriglyceridemia and hyperTG and chylomicronemia are still present and visible as lipemia often more than 12 hours after meals. In certain embodiments, LPLD is associated with at least one mutation in the LPL gene such as P207L, G188L or D9N or other mutations that affect LPL (Brunzell, In: Pagon R A, Adam M P, Bird T D, Dolan C R, Fong C T, Stephens K, editors. GeneReviews™ [Internet]. Seattle (Wash.): University of Washington, Seattle; 1993-2013. 1999 Oct. 12 [updated 2011 Dec. 15]).

"Low density lipoprotein-cholesterol (LDL-C)" means cholesterol carried in low density lipoprotein particles. Concentration of LDL-C in serum (or plasma) is typically quantified in mg/dL or nmol/L. "Serum LDL-C" and "plasma LDL-C" mean LDL-C in the serum and plasma, respectively.

"Major risk factors" refers to factors that contribute to a high risk for a particular disease or condition. In certain embodiments, major risk factors for coronary heart disease include, without limitation, cigarette smoking, hypertension, low HDL-C, family history of coronary heart disease, age, and other factors disclosed herein.

"Metabolic disorder" or "metabolic disease" refers to a condition characterized by an alteration or disturbance in metabolic function. "Metabolic" and "metabolism" are terms well known in the art and generally include the whole range of biochemical processes that occur within a living organism. Metabolic disorders include, but are not limited to, hyperglycemia, prediabetes, diabetes (type 1 and type 2), obesity, insulin resistance, metabolic syndrome and dyslipidemia due to type 2 diabetes.

"Metabolic syndrome" means a condition characterized by a clustering of lipid and non-lipid cardiovascular risk factors of metabolic origin. In certain embodiments, metabolic syndrome is identified by the presence of any 3 of the following factors: waist circumference of greater than 102 cm in men or greater than 88 cm in women; serum triglyceride of at least 150 mg/dL; HDL-C less than 40 mg/dL in men or less than 50 mg/dL in women; blood pressure of at least 130/85 mmHg; and fasting glucose of at least 110 mg/dL. These determinants can be readily measured in clinical practice (JAMA, 2001, 285: 2486-2497).

"Mismatch" or "non-complementary nucleobase" refers to the case when a nucleobase of a first nucleic acid is not capable of pairing with the corresponding nucleobase of a second or target nucleic acid.

"Mixed dyslipidemia" means a condition characterized by elevated cholesterol and elevated triglycerides.

"Modified internucleoside linkage" refers to a substitution or any change from a naturally occurring internucleoside bond. For example, a phosphorothioate linkage is a modified internucleoside linkage.

"Modified nucleobase" refers to any nucleobase other than adenine, cytosine, guanine, thymidine, or uracil. For example, 5-methylcytosine is a modified nucleobase. An "unmodified nucleobase" means the purine bases adenine (A) and guanine (G), and the pyrimidine bases thymine (T), cytosine (C), and uracil (U).

"Modified nucleoside" means a nucleoside having at least one modified sugar moiety, and/or modified nucleobase.

"Modified nucleotide" means a nucleotide having at least one modified sugar moiety, modified internucleoside linkage and/or modified nucleobase.

"Modified oligonucleotide" means an oligonucleotide comprising at least one modified nucleotide.

"Modified sugar" refers to a substitution or change from a natural sugar. For example, a 2'-O-methoxyethyl modified sugar is a modified sugar.

"Motif" means the pattern of chemically distinct regions in an antisense compound.

"Naturally occurring internucleoside linkage" means a 3' to 5' phosphodiester linkage.

"Natural sugar moiety" means a sugar found in DNA (2'-H) or RNA (2'-OH).

"Nicotinic acid" or "niacin" has been reported to decrease fatty acid influx to the liver and the secretion of VLDL by the liver. This effect appears to be mediated in part by the effects on hormone-sensitive lipase in the adipose tissue. Nicotinic acid has key action sites in both liver and adipose tissue. In the liver, nicotinic acid is reported to inhibit diacylglycerol acyltransferase-2 (DGAT-2) that results in the decreased secretion of VLDL particles from the liver, which is also reflected in reductions of both IDL and LDL particles, in addition, nicotinic acid raises HDL-C and apo A1 primarily by stimulating apo A1 production in the liver and has also been shown to reduce VLDL-ApoCIII concentrations in patients with hyperlipidemia (Wahlberg et al. Acta Med Scand 1988; 224:319-327). The effects of nicotinic acid on lipolysis and fatty acid mobilization in adipocytes are well established. However, nicotinic acid has not been effective in treating LPLD subjects with hypertriglyceridemia.

"Nucleic acid" refers to molecules composed of monomeric nucleotides. A nucleic acid includes ribonucleic acids (RNA), deoxyribonucleic acids (DNA), single-stranded nucleic acids (ssDNA), double-stranded nucleic acids (dsDNA), small interfering ribonucleic acids (siRNA), and microRNAs (miRNA). A nucleic acid may also comprise a combination of these elements in a single molecule.

"Nucleobase" means a heterocyclic moiety capable of pairing with a base of another nucleic acid.

"Nucleobase complementarity" refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the oligonucleotide and the target nucleic acid are considered to be complementary at that nucleobase pair.

"Nucleobase sequence" means the order of contiguous nucleobases independent of any sugar, linkage, or nucleobase modification.

"Nucleoside" means a nucleobase linked to a sugar.

"Nucleoside mimetic" includes those structures used to replace the sugar or the sugar and the base, and not necessarily the linkage at one or more positions of an oligomeric compound; for example nucleoside mimetics having morpholino, cyclohexenyl, cyclohexyl, tetrahydropyranyl, bicyclo or tricyclo sugar mimetics such as non-furanose sugar units.

"Nucleotide" means a nucleoside having a phosphate group covalently linked to the sugar portion of the nucleoside.

"Nucleotide mimetic" includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage).

"Oligomeric compound" or "oligomer" means a polymer of linked monomeric subunits which is capable of hybridizing to a region of a nucleic acid molecule. In certain embodiments, oligomeric compounds are oligonucleosides. In certain embodiments, oligomeric compounds are oligonucleotides. In certain embodiments, oligomeric compounds are antisense compounds. In certain embodiments, oligomeric compounds are antisense oligonucleotides. In certain embodiments, oligomeric compounds are chimeric oligonucleotides.

"Oligonucleotide" means a polymer of linked nucleosides each of which can be modified or unmodified, independent from one another.

"Parenteral administration" means administration through injection or infusion. Parenteral administration includes subcutaneous administration, intravenous administration, intramuscular administration, intraarterial administration, intraperitoneal administration, or intracranial administration, e.g. intrathecal or intracerebroventricular administration. Administration can be continuous, chronic, short or intermittent.

"Peptide" means a molecule formed by linking at least two amino acids by amide bonds. Peptide refers to polypeptides and proteins.

"Pharmaceutical agent" means a substance that provides a therapeutic benefit when administered to an individual. For example, in certain embodiments, an antisense oligonucleotide targeted to ApoCIII is pharmaceutical agent.

"Pharmaceutical composition" or "composition" means a mixture of substances suitable for administering to an individual. For example, a pharmaceutical composition may comprise one or more active agents and a pharmaceutical carrier, such as a sterile aqueous solution.

"Pharmaceutically acceptable carrier" means a medium or diluent that does not interfere with the structure of the compound. Certain of such carriers enable pharmaceutical compositions to be formulated as, for example, tablets, pills, dragees, capsules, liquids, gels, syrups, slurries, suspension and lozenges for the oral ingestion by a subject. Certain of such carriers enable pharmaceutical compositions to be formulated for injection, infusion or topical administration. For example, a pharmaceutically acceptable carrier can be a sterile aqueous solution.

"Pharmaceutically acceptable derivative" or "salts" encompasses derivatives of the compounds described herein such as solvates, hydrates, esters, prodrugs, polymorphs, isomers, isotopically labelled variants, pharmaceutically acceptable salts and other derivatives known in the art.

"Pharmaceutically acceptable salts" means physiologically and pharmaceutically acceptable salts of antisense compounds, i.e., salts that retain the desired biological activity of the parent compound and do not impart undesired toxicological effects thereto. The term "pharmaceutically acceptable salt" or "salt" includes a salt prepared from pharmaceutically acceptable non-toxic acids or bases, including inorganic or organic acids and bases. Pharmaceutically acceptable salts of the compounds described herein may be prepared by methods well-known in the art. For a review of pharmaceutically acceptable salts, see Stahl and Wermuth, Handbook of Pharmaceutical Salts: Properties, Selection and Use (Wiley-VCH, Weinheim, Germany, 2002). Sodium salts of antisense oligonucleotides are useful and are well accepted for therapeutic administration to humans. Accordingly, in one embodiment the compounds described herein are in the form of a sodium salt.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i e linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" refers to delaying or forestalling the onset or development of a disease, disorder, or condition for a period of time from minutes to indefinitely. Prevent also means reducing risk of developing a disease, disorder, or condition.

"Prodrug" means a therapeutic agent that is prepared in an inactive form that is converted to an active form (i.e., a drug) within the body or cells thereof by the action of endogenous enzymes or other chemicals or conditions.

"Raise" means to increase in amount. For example, to raise plasma HDL levels means to increase the amount of HDL in the plasma.

"Ratio of TG to HDL" means the TG levels relative to HDL levels. The occurrence of high TG and/or low HDL has been linked to cardiovascular disease incidence, outcomes and mortality. "Improving the ratio of TG to HDL" means to decrease TG and/or raise HDL levels.

"Reduce" means to bring down to a smaller extent, size, amount, or number. For example, to reduce plasma triglyceride levels means to bring down the amount of triglyceride in the plasma.

"Region" or "target region" is defined as a portion of the target nucleic acid having at least one identifiable structure, function, or characteristic. For example, a target region may encompass a 3' UTR, a 5' UTR, an exon, an intron, an exon/intron junction, a coding region, a translation initiation region, translation termination region, or other defined nucleic acid region. The structurally defined regions for ApoCIII can be obtained by accession number from sequence databases such as NCBI and such information is incorporated herein by reference. In certain embodiments, a target region may encompass the sequence from a 5' target site of one target segment within the target region to a 3' target site of another target segment within the target region.

"Ribonucleotide" means a nucleotide having a hydroxy at the 2' position of the sugar portion of the nucleotide. Ribonucleotides can be modified with any of a variety of substituents.

"Second agent" or "second therapeutic agent" means an agent that can be used in combination with a "first agent". A second therapeutic agent can include, but is not limited to, an siRNA or antisense oligonucleotide including antisense oligonucleotides targeting ApoCIII. A second agent can also include anti-ApoCIII antibodies, ApoCIII peptide inhibitors, DGAT1 inhibitors, cholesterol lowering agents, lipid lowering agents, glucose lowering agents and anti-inflammatory agents.

"Segments" are defined as smaller, sub-portions of regions within a nucleic acid. For example, a "target segment" means the sequence of nucleotides of a target nucleic acid to which one or more antisense compounds is targeted. "5' target site" refers to the 5'-most nucleotide of a target segment. "3' target site" refers to the 3'-most nucleotide of a target segment.

"Shortened" or "truncated" versions of antisense oligonucleotides or target nucleic acids taught herein have one, two or more nucleosides deleted.

"Side effects" means physiological responses attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum may indicate liver toxicity or liver function abnormality. For example, increased bilirubin may indicate liver toxicity or liver function abnormality.

"Single-stranded oligonucleotide" means an oligonucleotide which is not hybridized to a complementary strand.

"Specifically hybridizable" refers to an antisense compound having a sufficient degree of complementarity to a target nucleic acid to induce a desired effect, while exhibiting minimal or no effects on non-target nucleic acids under conditions in which specific binding is desired, i.e. under physiological conditions in the case of in vivo assays and therapeutic treatments.

"Statin" means an agent that inhibits the activity of HMG-CoA reductase. Statins reduce synthesis of cholesterol in the liver by competitively inhibiting HMG-CoA reductase activity. The reduction in intracellular cholesterol concentration induces LDL receptor expression on the hepatocyte cell surface, which results in increased extraction of LDL-C from the blood and a decreased concentration of circulating LDL-C and other apo-B containing lipoproteins including TG-rich particles. Independent of their effects on LDL-C and LDL receptor, statins lower the plasma concentration and cellular mRNA levels of ApoC-III (Ooi et al. *Clinical Sci*, 2008, 114:611-624). As statins have significant effects on mortality as well as most cardiovascular disease outcome parameters, these drugs are the first choice to reduce both total cardiovascular disease risk and moderately elevated TG levels. More potent statins (atorvastatin, rosuvastatin, and pitavastatin) demonstrate a robust lowering of TG levels, especially at high doses and in patients with elevated TG. However, statins have been ineffective in treating LPLD subjects with hypertriglyceridemia.

"Subcutaneous administration" means administration just below the skin.

"Subject" means a human or non-human animal selected for treatment or therapy.

"Symptom of cardiovascular disease or disorder" means a phenomenon that arises from and accompanies the cardiovascular disease or disorder and serves as an indication of it. For example, angina; chest pain; shortness of breath; palpitations; weakness; dizziness; nausea; sweating; tachycardia; bradycardia; arrhythmia; atrial fibrillation; swelling in the lower extremities; cyanosis; fatigue; fainting; numbness of the face; numbness of the limbs; claudication or cramping of muscles; bloating of the abdomen; or fever are symptoms of cardiovascular disease or disorder.

"Targeting" or "targeted" means the process of design and selection of an antisense compound that will specifically hybridize to a target nucleic acid and induce a desired effect.

"Target nucleic acid," "target RNA," and "target RNA transcript" all refer to a nucleic acid capable of being targeted by antisense compounds.

"Therapeutic lifestyle change" means dietary and lifestyle changes intended to lower fat/adipose tissue mass and/or cholesterol. Such change can reduce the risk of developing heart disease, and may includes recommendations for dietary intake of total daily calories, total fat, saturated fat, polyunsaturated fat, monounsaturated fat, carbohydrate, protein, cholesterol, insoluble fiber, as well as recommendations for physical activity.

"Treat" refers to administering a compound of the invention to effect an alteration or improvement of a disease, disorder, or condition.

"Triglyceride" or "TG" means a lipid or neutral fat consisting of glycerol combined with three fatty acid molecules.

"Type 2 diabetes," (also known as "type 2 diabetes mellitus", "diabetes mellitus, type 2", "non-insulin-dependent diabetes (NIDDM)", "obesity related diabetes", or "adult-onset diabetes") is a metabolic disorder that is primarily characterized by insulin resistance, relative insulin deficiency, and hyperglycemia.

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

"Wing segment" means one or a plurality of nucleosides modified to impart to an oligonucleotide properties such as enhanced inhibitory activity, increased binding affinity for a target nucleic acid, or resistance to degradation by in vivo nucleases.

Certain Embodiments

Certain embodiments provide a method of reducing ApoCIII levels in an animal with Fredrickson Type I dyslipidemia, FCS, LPLD, comprising administering a therapeutically effective amount of a compound comprising an ApoCIII specific inhibitor to the animal. In certain embodiments, ApoCIII levels are reduced in the liver, adipose tissue, heart, skeletal muscle or small intestine.

Certain embodiments provide a method of treating, preventing, delaying or ameliorating Fredrickson Type I dyslipidemia, FCS, LPLD, in an animal comprising administering a therapeutically effective amount of a compound comprising an ApoCIII specific inhibitor to the animal. In certain embodiments, a cardiovascular and/or metabolic disease or disorder, or symptom or risk thereof, related to Fredrickson Type I dyslipidemia, FCS, LPLD, is improved.

Certain embodiments provide a method of treating, preventing, delaying or ameliorating pancreatitis in an animal with Fredrickson Type I dyslipidemia, FCS, LPLD, comprising administering a therapeutically effective amount of a compound comprising an ApoCIII specific inhibitor to the animal. In certain embodiments, pancreatitis, or a symptom or risk thereof, is improved.

Certain embodiments provide a method of reducing TG levels in an animal with Fredrickson Type I dyslipidemia, FCS, LPLD, comprising administering a therapeutically effective amount of a compound comprising an ApoCIII specific inhibitor to the animal.

In certain embodiments, the animal has a TG level of at least ≥1200 mg/dL, ≥1100 mg/dL, ≥1000 mg/dL, ≥900 mg/dL, ≥880 mg/dL, ≥850 mg/dL, ≥800 mg/dL, ≥750 mg/dL, ≥700 mg/dL, ≥650 mg/dL, ≥600 mg/dL, ≥550 mg/dL, ≥500 mg/dL, ≥450 mg/dL, ≥440 mg/dL, ≥400 mg/dL, ≥350 mg/dL, ≥300 mg/dL, ≥250 mg/dL, ≥200 mg/dL, ≥150 mg/dL In certain embodiments, the animal has a history of TG level ≥880 mg/dL, fasting TG level ≥750 mg/dL and/or TG level ≥440 mg/dL after dieting.

In certain embodiments, the compound decreases TGs (postprandial or fasting) by at least 90%, by at least 80%, by at least 70%, by at least 60%, by at least 50%, by at least 45%, at least 40%, by at least 35%, by at least 30%, by at least 25%, by at least 20%, by at least 15%, by at least 10%, by at least 5% or by at least 1% from the baseline TG level. In certain embodiments, the TG (postprandial or fasting) level is ≤1900 mg/dL, ≤1800 mg/dL, ≤1700 mg/dL, ≤1600 mg/dL, ≤1500 mg/dL, ≤1400 mg/dL, ≤1300 mg/dL, ≤1200 mg/dL, ≤1100 mg/dL, ≤1000 mg/dL, ≤900 mg/dL, ≤800 mg/dL, ≤750 mg/dL, ≤700 mg/dL, ≤650 mg/dL, ≤600 mg/dL, ≤550 mg/dL, ≤500 mg/dL, ≤450 mg/dL, ≤400 mg/dL, ≤350 mg/dL, ≤300 mg/dL, ≤250 mg/dL, ≤200 mg/dL, ≤150 mg/dL or ≤100 mg/dL.

Certain embodiments provide a method of increasing HDL levels and/or improving the ratio of TG to HDL in an animal with Fredrickson Type I dyslipidemia, FCS, LPLD, comprising administering a therapeutically effective amount of a compound comprising an ApoCIII specific inhibitor to the animal. In certain embodiments, the compound increases HDL (postprandial or fasting) by at least 90%, by at least 80%, by at least 70%, by at least 60%, by at least 50%, by at least 45%, at least 40%, by at least 35%, by at least 30%, by at least 25%, by at least 20%, by at least 15%, by at least 10%, by at least 5% or by at least 1% from the baseline HDL level.

In certain embodiments, the compound decreases ApoCIII by about 81%, decreases TG by about 69%, decreases VLDL ApoCIII by about 80%, increases HDL by about 78%, decreases non-HDL-C by about 58% and/or decreases ApoB by about 13%.

Certain embodiments provide a method of preventing, delaying or ameliorating a cardiovascular and/or metabolic disease, disorder, condition, or symptom thereof, in an animal with Fredrickson Type I dyslipidemia, FCS, LPLD, comprising administering a therapeutically effective amount of a compound comprising an ApoCIII specific inhibitor to the animal. In certain embodiments, the compound prevents, delays or ameliorates the cardiovascular and/or metabolic disease, disorder, condition, or symptom thereof, in the animal with Fredrickson Type I dyslipidemia, FCS, LPLD, by decreasing TG levels, increasing HDL levels in the animal and/or improving the ratio of TG to HDL.

Certain embodiments provide a method of preventing, delaying or ameliorating pancreatitis, or symptom thereof, in an animal with Fredrickson Type I dyslipidemia, FCS, LPLD, comprising administering a therapeutically effective amount of a compound comprising an ApoCIII specific inhibitor to the animal. In certain embodiments, the compound prevents, delays or ameliorates pancreatitis, or symptom thereof, in the animal with Fredrickson Type I dyslipidemia, FCS, LPLD, by decreasing TG levels, increasing HDL levels in the animal and/or improving the ratio of TG to HDL.

Certain embodiments provide a method of preventing, delaying or ameliorating pancreatitis, or symptom thereof, in an animal with Fredrickson Type I dyslipidemia, FCS, LPLD, comprising administering a therapeutically effective amount of a compound comprising an ApoCIII specific inhibitor to the animal. In certain embodiments, the compound prevents, delays or ameliorates the pancreatitis, or symptom thereof, in the animal with Fredrickson Type I dyslipidemia, FCS, LPLD, by decreasing TG levels, increasing HDL levels in the animal and/or improving the ratio of TG to HDL.

Certain embodiments provide a method of preventing, treating, ameliorating, delaying the onset, or reducing the risk of, a cardiovascular disease, disorder or condition in an animal with Fredrickson Type I dyslipidemia, FCS, LPLD, comprising administering a therapeutically effective amount of a compound comprising an ApoCIII specific inhibitor to the animal. In certain embodiments, the compound prevents, treats, ameliorates, delays the onset, or reduces of the risk of the cardiovascular disease, disorder or condition in the animal with Fredrickson Type I dyslipidemia, FCS, LPLD, by decreasing TG levels, increasing HDL levels and/or improving the ratio of TG to HDL.

Certain embodiments provide a method of decreasing CETP, VLDL, VLDL ApoCIII, cholesterol, chylomicrons and/or ApoB levels in an animal with Fredrickson Type I dyslipidemia, FCS, LPLD, comprising administering a therapeutically effective amount of a compound comprising an ApoCIII specific inhibitor to the animal. In certain embodiments, the ApoB is ApoB-48 or ApoB-100. In certain embodiments, the amount of ApoB-48 reflects the amount of chylomicrons in the animal. In certain embodiments, the cholesterol is total cholesterol or non-HDL-cholesterol.

Certain embodiments provide a method of increasing ApoA1, PON1, fat clearance, chylomicron-triglyceride (CM-TG) clearance and/or HDL in an animal with Fredrickson Type I dyslipidemia, FCS, LPLD, comprising administering a therapeutically effective amount of a compound comprising an ApoCIII specific inhibitor to the animal. Certain embodiments provide a method for improving the ratio of TG to HDL in an animal with Fredrickson Type I dyslipidemia, FCS, LPLD comprising administering a therapeutically effective amount of a compound comprising an ApoCIII specific inhibitor to the animal.

Certain embodiments provide a method for treating adult patients with Fredrickson Type I dyslipidemia, FCS, LPLD suffering from severe or multiple pancreatitis attacks comprising comprising administering a therapeutically effective amount of a compound comprising an ApoCIII specific inhibitor to the patient. In certain embodiments, the patient suffers from pancreatitis despite dietary fat restrictions.

Certain embodiments provide a method for identifying a subject suffering from Fredrickson Type I dyslipidemia, FCS, LPLD, comprising genetically screening the subject.

Certain embodiments provide a method for identifying a subject at risk for Fredrickson Type I dyslipidemia, FCS, LPLD, comprising genetically screening the subject. In certain embodiments the genetic screening is performed by sequence analysis of the gene or RNA transcript encoding LPL or ApoC-II. In certain embodiments, the subject is genetically screened for at least one mutation in the LPL gene such as P207L, G188L, D9N or other mutations that affect LPL (Brunzell, In: Pagon R A, Adam M P, Bird T D, Dolan C R, Fong C T, Stephens K, editors. GeneReviews™ [Internet]. Seattle (Wash.): University of Washington, Seattle; 1993-2013. 1999 Oct. 12 [updated 2011 Dec. 15]).

Certain embodiments provide a method for identifying a subject suffering from Fredrickson Type I dyslipidemia, FCS, LPLD, comprising screening the subject for the presence of LPL inhibiting antibodies. Certain embodiments provide a method for identifying a subject at risk for Fredrickson Type I dyslipidemia, FCS, LPLD, comprising screening the subject for the presence of LPL inhibiting antibodies.

In certain embodiments, the level of LPL expression in a LPLD subject is undetectable. In certain embodiments, the level of LPL in a LPLD subject is detectable. In certain embodiments, the level of LPL in the LPLD subject is at most 25%, at most 24%, at most 23%, at most 22%, at most 21%, at most 20%, at most 19%, at most 18%, at most 17%, at most 16%, at most 15%, at most 14%, at most 13%, at most 12%, at most 11%, at most 10%, at most 9%, at most 8%, at most 7%, at most 6%, at most 5%, at most 4%, at most 3%, at most 2% or at most 1% of the LPL level of a non-LPLD subject.

In certain embodiments, the level of LPL activity in a LPLD subject is undetectable. In certain embodiments, the level of LPL activity in a LPLD subject is detectable. In certain embodiments, the level of LPL activity in the LPLD subject is at most 25%, at most 24%, at most 23%, at most 22%, at most 21%, at most 20%, at most 19%, at most 18%, at most 17%, at most 16%, at most 15%, at most 14%, at most 13%, at most 12%, at most 11%, at most 10%, at most 9%, at most 8%, at most 7%, at most 6%, at most 5%, at most 4%, at most 3%, at most 2% or at most 1% of the LPL activity level of a non-LPLD subject. In certain embodiments, the ApoCIII nucleic acid is any of the sequences set forth in GENBANK Accession No. NM_000040.1 (incorporated herein as SEQ ID NO: 1), GENBANK Accession No. NT_033899.8 truncated from nucleotides 20262640 to 20266603 (incorporated herein as SEQ ID NO: 2), and GenBank Accession No. NT_035088.1 truncated from nucleotides 6238608 to 6242565 (incorporated herein as SEQ ID NO: 4).

In certain embodiments, the ApoCIII specific inhibitor is a nucleic acid, peptide, antibody, small molecule or other agent capable of inhibiting the expression of ApoCIII. In certain embodiments, the nucleic acid is an antisense compound targeting ApoCIII. In certain embodiments, the antisense compound is an antisense oligonucleotide. In certain embodiments, the antisense oligonucleotide is a modified oligonucleotide. In certain embodiments, the modified oligonucleotide has a sequence complementary to SEQ ID NO: 1, SEQ ID NO: 2 or SEQ ID NO: 4. In certain embodiments, the modified oligonucleotide is at least 70%, at least 75%, at least 80%, at least 85%, at least 90%, at least 95%, at least 98% or at least 100% complementary to SEQ ID NO: 1, SEQ ID NO: 2 or SEQ ID NO: 4.

In certain embodiments, the modified oligonucleotide has a nucleobase sequence comprising at least 8 contiguous nucleobases of an antisense oligonucleotide complementary to an ApoCIII. In certain embodiments, the modified oligonucleotide has a nucleobase sequence comprising at least 8 contiguous nucleobases of ISIS 304801 (SEQ ID NO: 3). In certain embodiments, the modified oligonucleotide has a nucleobase sequence of ISIS 304801 (SEQ ID NO: 3). In certain embodiments, the modified oligonucleotide targeting ApoCIII has a sequence other than that of SEQ ID NO: 3. In certain embodiments, the modified oligonucleotide has a nucleobase sequence comprising at least 8 contiguous nucleobases of a sequence selected from any sequence disclosed in U.S. Pat. No. 7,598,227, U.S. Pat. No. 7,750,141, PCT Publication WO 2004/093783 or PCT Publication WO 2012/149495, all incorporated-by-reference herein. In certain embodiments, the modified oligonucleotide has a sequence selected from any sequence disclosed in U.S. Pat. No. 7,598,227, U.S. Pat. No. 7,750,141, PCT Publication WO 2004/093783 or PCT Publication WO 2012/149495, all incorporated-by-reference herein.

In certain embodiments, the modified oligonucleotide consists of a single-stranded modified oligonucleotide.

In certain embodiments, the modified oligonucleotide consists of 12-30 linked nucleosides.

In certain embodiments, the modified oligonucleotide consists of 20 linked nucleosides. In certain embodiments, the modified oligonucleotide consists of 20 linked nucleosides and the nucleobase sequence of ISIS 304801 (SEQ ID NO: 3).

In certain embodiments, the compound comprises at least one modified internucleoside linkage. In certain embodiments, the internucleoside linkage is a phosphorothioate internucleoside linkage. In certain embodiments, each internucleoside linkage is a phosphorothioate internucleoside linkage.

In certain embodiments, the compound comprises at least one nucleoside comprising a modified sugar. In certain embodiments, the at least one modified sugar is a bicyclic sugar. In certain embodiments, the at least one modified sugar comprises a 2'-O-methoxyethyl.

In certain embodiments, the compound comprises at least one nucleoside comprising a modified nucleobase. In certain embodiments, the modified nucleobase is a 5-methylcytosine.

In certain embodiments, the compound comprises a modified oligonucleotide comprising: (i) a gap segment consisting of linked deoxynucleosides; (ii) a 5' wing segment consisting of linked nucleosides; (iii) a 3' wing segment consisting of linked nucleosides, wherein the gap segment is positioned immediately adjacent to and between the 5' wing segment and the 3' wing segment and wherein each nucleoside of each wing segment comprises a modified sugar.

In certain embodiments, the compound comprises a modified oligonucleotide comprising: (i) a gap segment consisting of 8-12 linked deoxynucleosides; (ii) a 5' wing segment consisting of 1-5 linked nucleosides; (iii) a 3' wing segment consisting of 1-5 linked nucleosides, wherein the gap segment is positioned immediately adjacent to and between the 5' wing segment and the 3' wing segment, wherein each nucleoside of each wing segment comprises a 2'-O-methoxyethyl sugar, wherein each cytosine is a 5-methylcytosine, and wherein each internucleoside linkage is a phosphorothioate linkage.

In certain embodiments, the compound comprises a modified oligonucleotide comprising: (i) a gap segment consisting of ten linked deoxynucleosides; (ii) a 5' wing segment consisting of five linked nucleosides; (iii) a 3' wing segment consisting of five linked nucleosides, wherein the gap segment is positioned immediately adjacent to and between the 5' wing segment and the 3' wing segment, wherein each nucleoside of each wing segment comprises a 2'-O-methoxyethyl sugar, wherein each cytosine is a 5-methylcytosine, and wherein each internucleoside linkage is a phosphorothioate linkage.

Certain embodiments provide a method of reducing the risk of a cardiovascular disease in an animal with Fredrickson Type I dyslipidemia, FCS, LPLD, by administering to the animal a therapeutically effective amount of a compound comprising a modified oligonucleotide consisting of 12 to 30 linked nucleosides, wherein the modified oligonucleotide is complementary to an ApoCIII nucleic acid and wherein the modified oligonucleotide decreases TG levels, increases HDL levels and/or improves the ratio of TG to HDL. In certain embodiments, the ApoCIII nucleic acid is SEQ ID NO: 1, SEQ ID NO: 2 or SEQ ID NO: 4. In certain embodiments, the modified oligonucleotide is at least 70%, least 75%, least 80%, at least 85%, at least 90%, at least 95%, at least 98% or 100% complementary to SEQ ID NO: 1, SEQ ID NO: 2 or SEQ ID NO: 4. In certain embodiments, the modified oligonucleotide comprises at least 8 contiguous nucleobases of an antisense oligonucleotide targeting ApoCIII. In further embodiments, the modified oligonucleotide comprises at least 8 contiguous nucleobases of the nucleobase sequence of ISIS 304801 (SEQ ID NO: 3).

Certain embodiments provide a method of preventing, treating, ameliorating, or reducing at least one symptom of a cardiovascular disease in an animal with Fredrickson Type I dyslipidemia, FCS, LPLD, comprising administering to the animal a therapeutically effective amount of a compound comprising a modified oligonucleotide consisting of 12 to 30 linked nucleosides and is complementary to an ApoCIII nucleic acid. In certain embodiments, the ApoCIII nucleic acid is either SEQ ID NO: 1, SEQ ID NO: 2 or SEQ ID NO: 4. In certain embodiments, the modified oligonucleotide is at least 70%, least 75%, at least 80%, at least 85%, at least 90%, at least 95%, at least 98% or 100% complementary to SEQ ID NO: 1, SEQ ID NO: 2 or SEQ ID NO: 4. In further embodiments, the modified oligonucleotide administered to the animal prevents, treats, ameliorates or reduces at least one symptom of the cardiovascular disease by decreasing TG levels, increasing HDL levels and/or improving the ratio of TG to HDL. In certain embodiments, the modified oligonucleotide comprises at least 8 contiguous nucleobases of an antisense oligonucleotide targeting ApoCIII. In further embodiments, the modified oligonucleotide comprises at least 8 contiguous nucleobases of ISIS 304801 (SEQ ID NO: 3).

In further embodiments, symptoms of a cardiovascular disease include, but are not limited to, angina; chest pain; shortness of breath; palpitations; weakness; dizziness; nausea; sweating; tachycardia; bradycardia; arrhythmia; atrial fibrillation; swelling in the lower extremities; cyanosis; fatigue; fainting; numbness of the face; numbness of the limbs; claudication or cramping of muscles; bloating of the abdomen; or fever.

Certain embodiments provide a method of decreasing TG levels, raising HDL levels and/or improving the ratio of TG to HDL in an animal with Fredrickson Type I dyslipidemia, FCS, LPLD, by administering to the animal a therapeutically effective amount of a compound consisting of a modified oligonucleotide targeting ApoCIII. Further embodiments provide a method of preventing, treating, ameliorating or reducing at least one symptom of a cardiovascular and/or metabolic disease, disorder, condition, or symptom thereof, in the animal by administering to the animal a compound consisting of a modified oligonucleotide targeting ApoCIII, thereby decreasing TG levels, increasing the HDL levels and/or improving the ratio of TG to HDL in the animal.

Certain embodiments provide a method of decreasing TG levels, raising HDL levels and/or improving the ratio of TG to HDL in an animal with Fredrickson Type I dyslipidemia, FCS, LPLD, by administering to the animal a therapeutically effective amount of a compound consisting of the nucleobase sequence of ISIS 304801 (SEQ ID NO: 3). Further embodiments provide a method of preventing, treating, ameliorating or reducing at least one symptom of a cardiovascular and/or metabolic disease, disorder, condition, or symptom thereof, in the animal by administering to the animal a compound consisting of the nucleobase sequence of ISIS 304801 (SEQ ID NO: 3), thereby decreasing TG levels, increasing the HDL levels and/or improving the ratio of TG to HDL in the animal.

Certain embodiments provide a method of decreasing TG levels, raising HDL levels and/or improving the ratio of TG to HDL in an animal with Fredrickson Type I dyslipidemia, FCS, LPLD, by administering to the animal a therapeutically effective amount of a modified oligonucleotide having the sequence of ISIS 304801 (SEQ ID NO: 3), wherein the modified oligonucleotide comprises: (i) a gap segment consisting of ten linked deoxynucleosides; (ii) a 5' wing segment consisting of five linked nucleosides; (iii) a 3' wing segment consisting of five linked nucleosides, wherein the gap segment is positioned immediately adjacent to and between the 5' wing segment and the 3' wing segment, wherein each nucleoside of each wing segment comprises a 2'-O-methoxyethyl sugar, wherein each cytosine is a 5-methylcytosine, and wherein each internucleoside linkage is a phosphorothioate linkage.

Certain embodiments provide a method of preventing, delaying, treating, ameliorating, or reducing at least one symptom of a cardiovascular and/or metabolic disease, disorder, condition, or symptom thereof, in an animal with Fredrickson Type I dyslipidemia, FCS, LPLD, by administering to the animal a therapeutically effective amount of a modified oligonucleotide targeting ApoCIII, wherein the modified oligonucleotide of the compound comprises: (i) a gap segment consisting of ten linked deoxynucleosides; (ii) a 5' wing segment consisting of five linked nucleosides; (iii) a 3' wing segment consisting of five linked nucleosides, wherein the gap segment is positioned immediately adjacent to and between the 5' wing segment and the 3' wing segment, wherein each nucleoside of each wing segment comprises a 2'-O-methoxyethyl sugar, wherein each cytosine is a 5-methylcytosine, and wherein each internucleoside linkage is a phosphorothioate linkage.

Certain embodiments provide a method of preventing, delaying, treating, ameliorating, or reducing at least one symptom of a cardiovascular and/or metabolic disease, disorder, condition, or symptom thereof, in an animal with Fredrickson Type I dyslipidemia, FCS, LPLD, by administering to the animal a therapeutically effective amount of a modified oligonucleotide having the sequence of ISIS 304801 (SEQ ID NO: 3), wherein the modified oligonucleotide of the compound comprises: (i) a gap segment consisting of ten linked deoxynucleosides; (ii) a 5' wing segment consisting of five linked nucleosides; (iii) a 3' wing segment consisting of five linked nucleosides, wherein the gap segment is positioned immediately adjacent to and between the 5' wing segment and the 3' wing segment, wherein each nucleoside of each wing segment comprises a 2'-O-methoxyethyl sugar, wherein each cytosine is a 5-methylcytosine, and wherein each internucleoside linkage is a phosphorothioate linkage.

Certain embodiments provide a method of decreasing TG levels, raising the HDL levels and/or improving the ratio of TG to HDL in an animal with Fredrickson Type I dyslipidemia, FCS, LPLD, by administering to the animal a therapeutically effective amount of a compound comprising a modified oligonucleotide consisting of 12 to 30 linked nucleosides, wherein the modified oligonucleotide is complementary to an ApoCIII nucleic acid. In certain embodiments, the ApoCIII nucleic acid is either SEQ ID NO: 1, SEQ ID NO: 2 or SEQ ID NO: 4. In certain embodiments, the modified oligonucleotide is at least 80%, at least 85%, at least 90%, at least 95%, at least 98% or at least 100% complementary to SEQ ID NO: 1, SEQ ID NO: 2 or SEQ ID NO: 4.

Certain embodiments provide a method of preventing, delaying, treating, ameliorating, or reducing at least one symptom of a cardiovascular and/or metabolic disease, disorder, condition, or symptom thereof, in an animal with Fredrickson Type I dyslipidemia, FCS, LPLD, by administering to the animal a compound comprising a therapeutically effective amount of a modified oligonucleotide consisting of 12 to 30 linked nucleosides, wherein the modified oligonucleotide is complementary to an ApoCIII nucleic acid, and decreases TG levels and/or raises the HDL levels in the animal. In certain embodiments, the ApoCIII nucleic acid is either SEQ ID NO: 1, SEQ ID NO: 2 or SEQ ID NO: 4. In certain embodiments, the modified oligonucleotide is at least 80%, at least 85%, at least 90%, at least 95%, at least 98% or at least 100% complementary to SEQ ID NO: 1, SEQ ID NO: 2 or SEQ ID NO: 4.

In certain embodiments, the animal is human.

In certain embodiments, the cardiovascular disease is aneurysm, angina, arrhythmia, atherosclerosis, cerebrovascular disease, coronary heart disease, hypertension, dyslipidemia, hyperlipidemia, hypertriglyceridemia or hypercholesterolemia. In certain embodiments, the dyslipidemia is hypertriglyceridemia or chylomicronemia (e.g., FCS). In certain embodiments, the metabolic disease is diabetes, obesity or metabolic syndrome.

In certain embodiments, the animal with Fredrickson Type I dyslipidemia, FCS, LPLD, is at risk for pancreatitis. In certain embodiments, reducing ApoCIII levels in the liver and/or small intestine prevents pancreatitis. In certain embodiments, reducing TG levels, raising HDL levels and/or improving the ratio of TG to HDL prevents pancreatitis.

In certain embodiments, reducing ApoCIII levels in the liver and/or small intestine of an animal with Fredrickson Type I dyslipidemia, FCS, LPLD, enhances clearance of postprandial TG. In certain embodiments, raising HDL levels and/or improving the ratio of TG to HDL enhance clearance of postprandial TG in an animal with Fredrickson Type I dyslipidemia, FCS, LPLD. In certain embodiments, reducing ApoCIII levels in the liver and/or small intestine lowers postprandial triglyceride in an animal with Fredrickson Type I dyslipidemia, FCS, LPLD. In certain embodiments, raising HDL levels and/or improving the ratio of TG to HDL lowers postprandial TG.

In certain embodiments, reducing ApoCIII levels in the liver and/or small intestine of an animal with Fredrickson Type I dyslipidemia, FCS, LPLD, improves the ratio of HDL to TG.

In certain embodiments, the compound is parenterally administered. In further embodiments, the parenteral administration is subcutaneous.

In certain embodiments, the compound is co-administered with a second agent or therapy. In certain embodiments, the second agent is an ApoCIII lowering agent, Apo C-II lowering agent, DGAT1 lowering agent, LPL raising agent, cholesterol lowering agent, non-HDL lipid lowering agent, LDL lowering agent, TG lowering agent, cholesterol lowering agent, HDL raising agent, fish oil, niacin (nicotinic acid), fibrate, statin, DCCR (salt of diazoxide), glucose-lowering agent or anti-diabetic agents. In certain embodiments, the second therapy is dietary fat restriction.

In certain embodiments, the ApoCIII lowering agents include an ApoCIII antisense oligonucleotide different from the first agent, fibrate or an Apo B antisense oligonucleotide.

In certain embodiments, the DGAT1 lowering agent is LCQ908.

In certain embodiments, the LPL raising agents include gene therapy agents that raise the level of LPL (e.g., Glybera®, normal copies of ApoC-II, GPIHBP1, APOA5, LMF1 or other genes that, when mutated, can lead to dysfunctional LPL).

In certain embodiments, the glucose-lowering and/or anti-diabetic agents include, but are not limited to, PPAR agonist, a dipeptidyl peptidase (IV) inhibitor, a GLP-1 analog, insulin or an insulin analog, an insulin secretagogue, a SGLT2 inhibitor, a human amylin analog, a biguanide, an alpha-glucosidase inhibitor, metformin, sulfonylurea, rosiglitazone, meglitinide, thiazolidinedione, alpha-glucosidase inhibitor and the like. The sulfonylurea can be acetohexamide, chlorpropamide, tolbutamide, tolazamide, glimepiride, a glipizide, a glyburide, or a gliclazide. The meglitinide can be nateglinide or repaglinide. The thiazolidinedione can be pioglitazone or rosiglitazone. The alpha-glucosidase can be acarbose or miglitol.

In certain embodiments, the cholesterol or lipid lowering agents include, but are not limited to, statins, bile acids sequestrants, nicotinic acid and fibrates. The statins can be atorvastatin, fluvastatin, lovastatin, pravastatin, rosuvastatin and simvastatin and the like. The bile acid sequestrants can be colesevelam, cholestyramine, colestipol and the like. The fibrates can be gemfibrozil, fenofibrate, clofibrate and the like. The therapeutic lifestyle change can be dietary fat restriction.

In certain embodiments, the HDL increasing agents include cholesteryl ester transfer protein (CETP) inhibiting drugs (such as Torcetrapib), peroxisome proliferation activated receptor agonists, Apo-A1, Pioglitazone and the like.

In certain embodiments, the compound and the second agent are administered concomitantly or sequentially.

In certain embodiments, the compound is a salt form. In further embodiments, the compound further comprises of a pharmaceutically acceptable carrier or diluent.

Certain embodiments provide a compound comprising an ApoCIII specific inhibitor for use in the preparation of a medicament for treating, preventing, delaying or ameliorating Fredrickson Type I dyslipidemia, FCS, LPLD.

Certain embodiments provide use of a compound comprising an ApoCIII specific inhibitor in the preparation of a medicament for decreasing ApoCIII levels in an animal with Fredrickson Type I dyslipidemia, FCS, LPLD. In certain embodiments, ApoCIII levels are decreased in the liver or small intestine.

Certain embodiments provide a use of a compound comprising an ApoCIII specific inhibitor in the preparation of a medicament for decreasing TG levels, increasing HDL levels and/or improving the ratio of TG to HDL in an animal with Fredrickson Type I dyslipidemia, FCS, LPLD.

Certain embodiments provide use of a compound comprising an ApoCIII specific inhibitor in the preparation of a medicament for preventing, treating, ameliorating or reducing at least one symptom of a cardiovascular or metabolic disease by decreasing TG levels, increasing HDL levels and/or improving the ratio of TG to HDL in an animal with Fredrickson Type I dyslipidemia, FCS, LPLD.

Certain embodiments provide use of a compound comprising an ApoCIII specific inhibitor in the preparation of a medicament for treating an animal with Fredrickson Type I dyslipidemia, FCS, LPLD, at risk for or having pancreatitis.

In certain embodiments, the ApoCIII specific inhibitor used in the preparation of a medicament is a nucleic acid, peptide, antibody, small molecule or other agent capable of inhibiting the expression of ApoCIII. In certain embodiments, the nucleic acid is an antisense compound. In certain embodiments, the antisense compound is a modified oligonucleotide targeting ApoCIII. In certain embodiments, the modified oligonucleotide has a nucleobase sequence comprising at least 8 contiguous nucleobases of ISIS 304801 (SEQ ID NO: 3). In certain embodiments, the modified oligonucleotide is at least 70%, at least 75%, at least 80%, at least 85%, at least 90%, at least 95%, at least 98% or at least 100% complementary to SEQ ID NO: 1, SEQ ID NO: 2 or SEQ ID NO: 4.

Certain embodiments provide a compound comprising an ApoCIII specific inhibitor for use in treating, preventing, delaying or ameliorating Fredrickson Type I dyslipidemia, FCS, LPLD.

Certain embodiments provide use of a compound comprising an ApoCIII specific inhibitor for decreasing ApoCIII levels in an animal with Fredrickson Type I dyslipidemia, FCS, LPLD. In certain embodiments, ApoCIII levels are decreased in the liver or small intestine.

Certain embodiments provide a use of a compound comprising an ApoCIII specific inhibitor for decreasing TG levels, increasing HDL levels and/or improving the ratio of TG to HDL in an animal with Fredrickson Type I dyslipidemia, FCS, LPLD.

Certain embodiments provide use of a compound comprising an ApoCIII specific inhibitor for preventing, treating, ameliorating or reducing at least one symptom of a cardiovascular disease by decreasing TG levels, increasing HDL levels and/or improving the ratio of TG to HDL in an animal with Fredrickson Type I dyslipidemia, FCS, LPLD.

Certain embodiments provide use of a compound comprising an ApoCIII specific inhibitor for treating an animal with Fredrickson Type I dyslipidemia, FCS, LPLD, at risk for or having pancreatitis.

In certain embodiments, the ApoCIII specific inhibitor used is a nucleic acid, peptide, antibody, small molecule or other agent capable of inhibiting the expression of ApoCIII. In certain embodiments, the nucleic acid is an antisense compound. In certain embodiments, the antisense compound is a modified oligonucleotide targeting ApoCIII. In certain embodiments, the modified oligonucleotide has a nucleobase sequence comprising at least 8 contiguous nucleobases of ISIS 304801 (SEQ ID NO: 3). In certain embodiments, the modified oligonucleotide is at least 70%, at least 75%, at least 80%, at least 85%, at least 90%, at least 95%, at least 98% or at least 100% complementary to SEQ ID NO: 1, SEQ ID NO: 2 or SEQ ID NO: 4.

Certain embodiments provide a composition comprising an ApoCIII specific inhibitor for use in: reducing TG levels in an animal with Fredrickson Type I dyslipidemia, FCS, LPLD; increasing HDL levels and/or improving the ratio of TG to HDL in an animal with Fredrickson Type I dyslipidemia, FCS, LPLD; preventing, delaying or ameliorating a cardiovascular and/or metabolic disease, disorder, condition, or a symptom thereof, in an animal with Fredrickson Type I dyslipidemia, FCS, LPLD; and/or preventing, delaying or ameliorating pancreatitis, or a symptom thereof, in an animal with Fredrickson Type I dyslipidemia, FCS, LPLD. In certain embodiments, the ApoCIII specific inhibitor is a nucleic acid, peptide, antibody, small molecule or other agent capable of inhibiting the expression of ApoCIII. In certain embodiments, the nucleic acid is an antisense compound. In certain embodiments, the antisense compound is a modified oligonucleotide targeting ApoCIII. In certain embodiments, the modified oligonucleotide has a nucleobase sequence comprising at least 8 contiguous nucleobases of ISIS 304801 (SEQ ID NO: 3). In certain embodiments, the modified oligonucleotide is at least 70%, at least 75%, at least 80%, at least 85%, at least 90%, at least 95%, at least 98% or at least 100% complementary to SEQ ID NO: 1, SEQ ID NO: 2 or SEQ ID NO: 4.

Certain embodiments provide a composition to reduce TG levels in an animal with Fredrickson Type I dyslipidemia, FCS, LPLD; increase HDL levels and/or improving the ratio of TG to HDL in an animal with Fredrickson Type I dyslipidemia, FCS, LPLD; prevent, delay or ameliorate a cardiovascular and/or metabolic disease, disorder, condition, or a symptom thereof, in an animal with Fredrickson Type I dyslipidemia, FCS, LPLD; and/or prevent, delay or ameliorate pancreatitis, or a symptom thereof, in an animal with Fredrickson Type I dyslipidemia, FCS, LPLD, comprising an ApoCIII specific inhibitor. In certain embodiments, the ApoCIII specific inhibitor is a nucleic acid, peptide, antibody, small molecule or other agent capable of inhibiting the expression of ApoCIII. In certain embodiments, the nucleic acid is an antisense compound. In certain embodiments, the antisense compound is a modified oligonucleotide targeting ApoCIII. In certain embodiments, the modified oligonucleotide has a nucleobase sequence comprising at least 8 contiguous nucleobases of ISIS 304801 (SEQ ID NO: 3). In certain embodiments, the modified oligonucleotide is at least 70%, at least 75%, at least 80%, at least 85%, at least 90%, at least 95%, at least 98% or at least 100% complementary to SEQ ID NO: 1, SEQ ID NO: 2 or SEQ ID NO: 4.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that it is capable of undergoing hybridization to a target nucleic acid through hydrogen bonding.

Antisense compounds provided herein refer to oligomeric compounds capable of undergoing hybridization to a target nucleic acid through hydrogen bonding. Examples of antisense compounds include single-stranded and double-stranded compounds, such as, antisense oligonucleotides, siRNAs, shRNAs, and miRNAs.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to an ApoCIII nucleic acid is 12 to 30 nucleotides in length.

In other words, antisense compounds are from 12 to 30 linked nucleobases. In other embodiments, the antisense compound comprises a modified oligonucleotide consisting of 8 to 80, 10 to 80, 12 to 50, 15 to 30, 18 to 24, 19 to 22, or 20 linked nucleobases. In certain such embodiments, the antisense compound comprises a modified oligonucleotide consisting of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked nucleobases in length, or a range defined by any two of the above values. In some embodiments, the antisense compound is an antisense oligonucleotide.

In certain embodiments, the antisense compound comprises a shortened or truncated modified oligonucleotide. The shortened or truncated modified oligonucleotide can have one or more nucleosides deleted from the 5' end (5' truncation), one or more nucleosides deleted from the 3' end (3' truncation) or one or more nucleosides deleted from the central portion. Alternatively, the deleted nucleosides may be dispersed throughout the modified oligonucleotide, for example, in an antisense compound having one nucleoside deleted from the 5' end and one nucleoside deleted from the 3' end.

When a single additional nucleoside is present in a lengthened oligonucleotide, the additional nucleoside may be located at the central portion, 5' or 3' end of the oligonucleotide. When two or more additional nucleosides are present, the added nucleosides may be adjacent to each other, for example, in an oligonucleotide having two nucleosides added to the central portion, to the 5' end (5' addition), or alternatively to the 3' end (3' addition), of the oligonucleotide. Alternatively, the added nucleosides may be dispersed throughout the antisense compound, for example, in an oligonucleotide having one nucleoside added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to an ApoCIII nucleic acid have chemically modified subunits arranged in patterns, or motifs, to confer to the antisense compounds properties such as enhanced inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of a RNA: DNA duplex.

Antisense compounds having a gapmer motif are considered chimeric antisense compounds. In a gapmer an internal region having a plurality of nucleotides that supports RNase H cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE, and 2'-O—CH$_3$, among others), and bicyclic sugar modified nucleosides (such bicyclic sugar modified nucleosides may include those having a 4'-(CH2) n-O-2' bridge, where n=1 or n=2). Preferably, each distinct region comprises uniform sugar moieties. The wing-gap-wing motif is frequently described as "X-Y-Z", where "X" represents the length of the 5' wing region, "Y" represents the length of the gap region, and "Z" represents the length of the 3' wing region. As used herein, a gapmer described as "X-Y-Z" has a configuration such that the gap segment is positioned immediately adjacent to each of the 5' wing segment and the 3' wing segment. Thus, no intervening nucleotides exist between the 5' wing segment and gap segment, or the gap segment and the 3' wing segment. Any of the antisense compounds described herein can have a gapmer motif. In some embodiments, X and Z are the same; in other embodiments they are different. In a preferred embodiment, Y is between 8 and 15 nucleotides. X, Y or Z can be any of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more nucleotides. Thus, gapmers include, but are not limited to, for example 5-10-5, 4-8-4, 4-12-3, 4-12-4, 3-14-3, 2-13-5, 2-16-2, 1-18-1, 3-10-3, 2-10-2, 1-10-1, 2-8-2, 6-8-6, 5-8-5, 1-8-1, 2-6-2, 2-13-2, 1-8-2, 2-8-3, 3-10-2, 1-18-2 or 2-18-2.

In certain embodiments, the antisense compound as a "wingmer" motif, having a wing-gap or gap-wing configuration, i.e. an X-Y or Y-Z configuration as described above for the gapmer configuration. Thus, wingmer configurations include, but are not limited to, for example 5-10, 8-4, 4-12, 12-4, 3-14, 16-2, 18-1, 10-3, 2-10, 1-10, 8-2, 2-13 or 5-13.

In certain embodiments, antisense compounds targeted to an ApoCIII nucleic acid possess a 5-10-5 gapmer motif.

In certain embodiments, an antisense compound targeted to an ApoCIII nucleic acid has a gap-widened motif.

Target Nucleic Acids, Target Regions and Nucleotide Sequences

Nucleotide sequences that encode ApoCIII include, without limitation, the following: GENBANK Accession No. NM_000040.1 (incorporated herein as SEQ ID NO: 1), GENBANK Accession No. NT_033899.8 truncated from nucleotides 20262640 to 20266603 (incorporated herein as SEQ ID NO: 2) and GenBank Accession No. NT_035088.1 truncated from nucleotides 6238608 to 6242565 (incorporated herein as SEQ ID NO: 4).

It is understood that the sequence set forth in each SEQ ID NO in the Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region may encompass a 3' UTR, a 5' UTR, an exon, an intron, an exon/intron junction, a coding region, a translation initiation region, translation termination region, or other defined nucleic acid region. The structurally defined regions for ApoCIII can be obtained by accession number from sequence databases such as NCBI and such information is incorporated herein by reference. In certain embodiments, a target region may encompass the sequence from a 5' target site of one target segment within the target region to a 3' target site of another target segment within the target region.

In certain embodiments, a "target segment" is a smaller, sub-portion of a target region within a nucleic acid. For example, a target segment can be the sequence of nucleotides of a target nucleic acid to which one or more antisense compounds are targeted. "5' target site" refers to the 5'-most nucleotide of a target segment. "3' target site" refers to the 3'-most nucleotide of a target segment.

A target region may contain one or more target segments. Multiple target segments within a target region may be overlapping. Alternatively, they may be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed, herein.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

Suitable target segments may be found within a 5' UTR, a coding region, a 3' UTR, an intron, an exon, or an exon/intron junction. Target segments containing a start codon or a stop codon are also suitable target segments. A suitable target segment may specifically exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There can be variation in activity (e.g., as defined by percent reduction of target nucleic acid levels) of the antisense compounds within an active target region. In certain embodiments, reductions in ApoCIII mRNA levels are indicative of inhibition of ApoCIII expression. Reductions in levels of an ApoCIII protein can be indicative of inhibition of target mRNA expression. Further, phenotypic changes can be indicative of inhibition of ApoCIII expression. For example, an increase in HDL level, decrease in LDL level, or decrease in TG level are among phenotypic changes that may be assayed for inhibition of ApoCIII expression. Other phenotypic indications, e.g., symptoms associated with a cardiovascular or metabolic disease, may also be assessed; for example, angina; chest pain; shortness of breath; palpitations; weakness; dizziness; nausea; sweating; tachycardia; bradycardia; arrhythmia; atrial fibrillation; swelling in the lower extremities; cyanosis; fatigue; fainting; numbness of the face; numbness of the limbs; claudication or cramping of muscles; bloating of the abdomen; or fever.

Hybridization

In some embodiments, hybridization occurs between an antisense compound disclosed herein and an ApoCIII nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art (Sambrook and Russell, Molecular Cloning: A Laboratory Manual, $3^{rd}$ Ed., 2001, CSHL Press). In certain embodiments, the antisense compounds provided herein are specifically hybridizable with an ApoCIII nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as an ApoCIII nucleic acid).

An antisense compound may hybridize over one or more segments of an ApoCIII nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 75%, 80%, 85%, 86%, 87%, 88%, 89%, 90%, 91%, 92%, 93%, 94%, 95%, 96%, 97%, 98%, 99%, or 100% complementary to an ApoCIII nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining non-complementary nucleobases may be clustered or interspersed with complementary nucleobases and need not be contiguous to each other or to complementary nucleobases. As such, an antisense compound which is 18 nucleobases in length having 4 (four) non-complementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

In certain embodiments, the antisense compounds provided herein, or specified portions thereof, are fully complementary (i.e. 100% complementary) to a target nucleic acid, or specified portion thereof. For example, an antisense compound may be fully complementary to an ApoCIII nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase(s) can be at the 5' end or 3' end of the antisense compound. Alternatively, the non-complementary nucleobase(s) can be at an internal position of the antisense compound. When two or more non-complementary nucleobases are present, they can be contiguous (i.e. linked) or non-contiguous. In one embodiment, a non-complementary nucleobase is located in the wing segment of a gapmer antisense oligonucleotide.

In certain embodiments, antisense compounds that are, or are up to, 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as an ApoCIII nucleic acid, or specified portion thereof.

In certain embodiments, antisense compounds that are, or are up to, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as an ApoCIII nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds are complementary to at least an 8 nucleobase portion of a target segment. In certain embodiments, the antisense compounds are complementary to at least a 10 nucleobase portion of a target segment. In certain embodiments, the antisense compounds are complementary to at least a 12 nucleobase portion of a target segment. In certain embodiments, the antisense compounds are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or sequence of a compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides can also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to an ApoCIII nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds of the invention can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise chemically modified ribofuranose ring moieties. Examples of chemically modified ribofuranose rings include without limitation, addition of substitutent groups (including 5' and 2' substituent groups, bridging of non-geminal ring atoms to form bicyclic nucleic acids (BNA), replacement of the ribosyl ring oxygen atom with S, N(R), or C($R_1$)($R_2$) (R, $R_1$ and $R_2$ are each independently H, $C_1$-$C_{12}$ alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-$OCH_3$, 2'-$OCH_2CH_3$, 2'-$OCH_2CH_2F$ and 2'-$O(CH_2)_2OCH_3$ substituent groups. The substituent at the 2' position can also be selected from allyl, amino, azido, thio, O-allyl, O—$C_1$-$C_{10}$ alkyl, $OCF_3$, $OCH_2F$, $O(CH_2)_2SCH_3$, $O(CH_2)_2$—O—N($R_m$)($R_n$), O—$CH_2$—C(=O)—N($R_m$)($R_n$), and O—$CH_2$—C(=O)—N($R_l$)—($CH_2$)$_2$—N($R_m$)($R_n$), where each $R_l$, $R_m$ and $R_n$ is, independently, H or substituted or unsubstituted $C_1$-$C_{10}$ alkyl.

As used herein, "bicyclic nucleosides" refer to modified nucleosides comprising a bicyclic sugar moiety. Examples of bicyclic nucleic acids (BNAs) include without limitation nucleosides comprising a bridge between the 4' and the 2' ribosyl ring atoms. In certain embodiments, antisense compounds provided herein include one or more BNA nucleosides wherein the bridge comprises one of the formulas: 4'-($CH_2$)—O-2' (LNA); 4'-($CH_2$)—S-2; 4'-($CH_2$)$_2$—O-2' (ENA); 4'-CH($CH_3$)—O-2' and 4'-CH($CH_2OCH_3$)—O-2' (and analogs thereof see U.S. Pat. No. 7,399,845, issued on Jul. 15, 2008); 4'-C($CH_3$)($CH_3$)—O-2' (and analogs thereof see PCT/US2008/068922 published as WO/2009/006478, published Jan. 8, 2009); 4'-$CH_2$—N($OCH_3$)-2' (and analogs thereof see PCT/US2008/064591 published as WO/2008/150729, published Dec. 11, 2008); 4'-$CH_2$—O—N($CH_3$)-2' (see published U.S. Patent Application US2004-0171570, published Sep. 2, 2004); 4'-$CH_2$—N(R)—O-2', wherein R is H, $C_1$-$C_{12}$ alkyl, or a protecting group (see U.S. Pat. No. 7,427,672, issued on Sep. 23, 2008); 4'-$CH_2$—C(H)($CH_3$)-2' (see Chattopadhyaya et al., *J. Org. Chem.*, 2009, 74, 118-134); and 4'-$CH_2$—C—(=$CH_2$)-2' (and analogs thereof see PCT/US2008/066154 published as WO 2008/154401, published on Dec. 8, 2008).

Further bicyclic nucleosides have been reported in published literature (see for example: Srivastava et al., *J. Am. Chem. Soc.*, 2007, 129(26) 8362-8379; Frieden et al., *Nucleic Acids Research*, 2003, 21, 6365-6372; Elayadi et al., *Curr. Opinion Invens. Drugs*, 2001, 2, 558-561; Braasch et al., *Chem. Biol.*, 2001, 8, 1-7; Orum et al., *Curr. Opinion Mol. Ther.*, 2001, 3, 239-243; Wahlestedt et al., *Proc. Natl. Acad. Sci. U.S.A*, 2000, 97, 5633-5638; Singh et al., *Chem. Commun.*, 1998, 4, 455-456; Koshkin et al., *Tetrahedron*, 1998, 54, 3607-3630; Kumar et al., *Bioorg. Med. Chem. Lett.*, 1998, 8, 2219-2222; Singh et al., *J. Org. Chem.*, 1998, 63, 10035-10039; U.S. Pat. Nos. 7,399,845; 7,053,207; 7,034,133; 6,794,499; 6,770,748; 6,670,461; 6,525,191; 6,268,490; U.S. patent Publication Nos.: US2008-0039618; US2007-0287831; US2004-0171570; U.S. patent applications, Ser. Nos. 12/129,154; 61/099,844; 61/097,787; 61/086,231; 61/056,564; 61/026,998; 61/026,995; 60/989,574; International applications WO 2007/134181; WO 2005/021570; WO 2004/106356; WO 94/14226; and PCT International Applications Nos.: PCT/US2008/068922; PCT/US2008/066154; and PCT/US2008/064591). Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

As used herein, "monocyclic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "4'-2' bicyclic nucleoside" or "4' to 2' bicyclic nucleoside" refers to a bicyclic nucleoside comprising a furanose ring comprising a bridge connecting two carbon atoms of the furanose ring connects the 2' carbon atom and the 4' carbon atom of the sugar ring.

In certain embodiments, bicyclic sugar moieties of BNA nucleosides include, but are not limited to, compounds having at least one bridge between the 4' and the 2' carbon atoms of the pentofuranosyl sugar moiety including without limitation, bridges comprising 1 or from 1 to 4 linked groups independently selected from —[C($R_a$)($R_b$)]$_n$—, —C($R_a$)=C($R_b$)—, —C($R_a$)=N—, —C(=N$R_a$)—, —C(=O)—, —C(=S)—, —O—, —Si($R_a$)$_2$—, —S(=O)$_x$—, and —N($R_a$)—; wherein: x is 0, 1, or 2; n is 1, 2, 3, or 4; each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl (S(=O)$_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl or a protecting group.

In certain embodiments, the bridge of a bicyclic sugar moiety is, —[C($R_a$)($R_b$)]$_n$—, —[C($R_a$)($R_b$)]$_n$—O—, —C($R_aR_b$)—N(R)—O— or —C($R_aR_b$)—O—N(R)—. In certain embodiments, the bridge is 4'-CH$_2$-2', 4'-(CH$_2$)$_2$-2', 4'-(CH$_2$)$_3$-2', 4'-CH$_2$—O-2', 4'-(CH$_2$)$_2$—O-2', 4'-CH$_2$—O—N(R)-2' and 4'-CH$_2$—N(R)—O-2'- wherein each R is, independently, H, a protecting group or $C_1$-$C_{12}$ alkyl.

In certain embodiments, bicyclic nucleosides are further defined by isomeric configuration. For example, a nucleoside comprising a 4'-(CH$_2$)—O-2' bridge, may be in the α-L configuration or in the β-D configuration. Previously, α-L-methyleneoxy (4'-CH$_2$—O-2') BNA's have been incorporated into antisense oligonucleotides that showed antisense activity (Frieden et al., *Nucleic Acids Research*, 2003, 21, 6365-6372).

In certain embodiments, bicyclic nucleosides include those having a 4' to 2' bridge wherein such bridges include without limitation, α-L-4'-(CH$_2$)—O-2', β-D-4'-CH$_2$—O-2', 4'-(CH$_2$)$_2$—O-2', 4'-CH$_2$—O—N(R)-2', 4'-CH$_2$—N(R)—O-2', 4'-CH(CH$_3$)—O-2', 4'-CH$_2$—S-2', 4'-CH$_2$—N(R)-2', 4'-CH$_2$—CH(CH$_3$)-2', and 4'-(CH$_2$)$_3$-2', wherein R is H, a protecting group or $C_1$-$C_{12}$ alkyl.

In certain embodiment, bicyclic nucleosides have the formula:

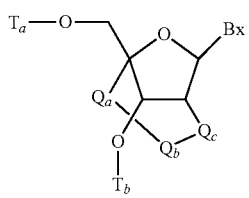

wherein:

Bx is a heterocyclic base moiety;

-$Q_a$-$Q_b$-$Q_c$- is —CH$_2$—N($R_c$)—CH$_2$—, —C(=O)—N($R_c$)—CH$_2$—, —CH$_2$—O—N($R_c$)—, —CH$_2$—N($R_c$)—O— or —N($R_c$)—O—CH$_2$;

$R_c$ is $C_1$-$C_{12}$ alkyl or an amino protecting group; and $T_a$ and $T_b$ are each, independently, H, a hydroxyl protecting group, a conjugate group, a reactive phosphorus group, a phosphorus moiety or a covalent attachment to a support medium.

In certain embodiments, bicyclic nucleosides have the formula:

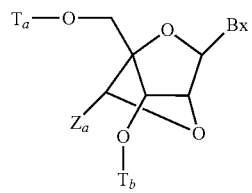

wherein:

Bx is a heterocyclic base moiety;

$T_a$ and $T_b$ are each, independently, H, a hydroxyl protecting group, a conjugate group, a reactive phosphorus group, a phosphorus moiety or a covalent attachment to a support medium;

$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol or substituted thiol.

In one embodiment, each of the substituted groups, is, independently, mono or poly substituted with substituent groups independently selected from halogen, oxo, hydroxyl, $OJ_c$, $NJ_cJ_d$, $SJ_c$, $N_3$, $OC(=X)J_c$, and $NJ_eC(=X)NJ_cJ_d$, wherein each $J_c$, $J_d$ and $J_e$ is, independently, H, $C_1$-$C_6$ alkyl, or substituted $C_1$-$C_6$ alkyl and X is O or $NJ_c$.

In certain embodiments, bicyclic nucleosides have the formula:

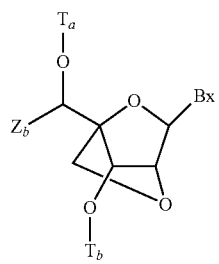

wherein:

Bx is a heterocyclic base moiety;

$T_a$ and $T_b$ are each, independently, H, a hydroxyl protecting group, a conjugate group, a reactive phosphorus group, a phosphorus moiety or a covalent attachment to a support medium;

$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl or substituted acyl (C(=O)—).

In certain embodiments, bicyclic nucleosides have the formula:

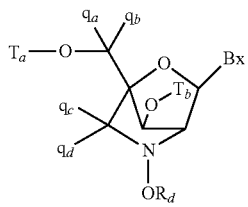

wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium;
$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

In certain embodiments, bicyclic nucleosides have the formula:

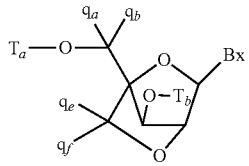

wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium;
$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$;
or $q_e$ and $q_f$ together are =C($q_g$)($q_h$);
$q_g$ and $q_h$ are each, independently, H, halogen, $C_1$-$C_{12}$ alkyl or substituted $C_1$-$C_{12}$ alkyl.

The synthesis and preparation of adenine, cytosine, guanine, 5-methyl-cytosine, thymine and uracil bicyclic nucleosides having a 4'-$CH_2$—O-2' bridge, along with their oligomerization, and nucleic acid recognition properties have been described (Koshkin et al., *Tetrahedron*, 1998, 54, 3607-3630). The synthesis of bicyclic nucleosides has also been described in WO 98/39352 and WO 99/14226.

Analogs of various bicyclic nucleosides that have 4' to 2' bridging groups such as 4'-$CH_2$—O-2' and 4'-$CH_2$—S-2', have also been prepared (Kumar et al., *Bioorg. Med. Chem. Lett.*, 1998, 8, 2219-2222). Preparation of oligodeoxyribonucleotide duplexes comprising bicyclic nucleosides for use as substrates for nucleic acid polymerases has also been described (Wengel et al., WO 99/14226). Furthermore, synthesis of 2'-amino-BNA, a novel conformationally restricted high-affinity oligonucleotide analog has been described in the art (Singh et al., *J. Org. Chem.*, 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleosides have the formula:

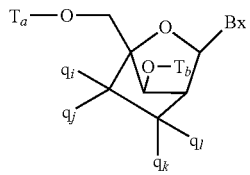

wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium;
each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$; and
$q_i$ and $q_j$ or $q_l$ and $q_k$ together are =C($q_g$)($q_h$), wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'-($CH_2$)$_3$-2' bridge and the alkenyl analog bridge 4'-CH=CH—$CH_2$-2' have been described (Frier et al., *Nucleic Acids Research*, 1997, 25(22), 4429-4443 and Albaek et al., *J. Org. Chem.*, 2006, 71, 7731-7740). The synthesis and preparation of carbocyclic bicyclic nucleosides along with their oligomerization and biochemical studies have also been described (Srivastava et al., *J. Am. Chem. Soc.* 2007, 129(26), 8362-8379).

In certain embodiments, bicyclic nucleosides include, but are not limited to, (A) α-L-methyleneoxy (4'-$CH_2$—O-2) BNA (B) β-D-methyleneoxy (4'-$CH_2$—O-2) BNA (C) ethyleneoxy (4'-($CH_2$)$_2$—O-2') BNA, (D) aminooxy (4'-$CH_2$—O—N(R)-2') BNA, (E) oxyamino (4'-$CH_2$—N(R)—O-2) BNA, (F) methyl(methyleneoxy) (4'-CH($CH_3$)—O-2) BNA (also referred to as constrained ethyl or cEt), (G) methylenethio (4'-$CH_2$—S-2') BNA, (H) methylene-amino (4'-$CH_2$—N(R)-2') BNA, (I) methyl carbocyclic (4'-$CH_2$—CH($CH_3$)-2) BNA, (J) propylene carbocyclic (4'-($CH_2$)$_3$-2') BNA, and (K) vinyl BNA as depicted below.

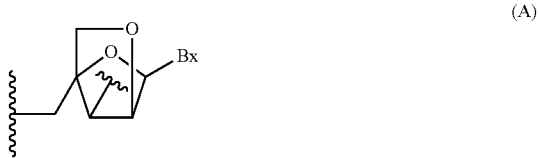

(A)

(B) 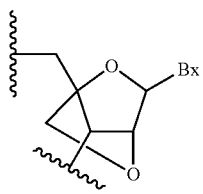

(C) 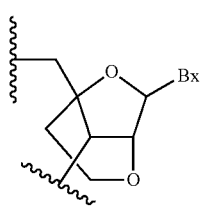

(D) 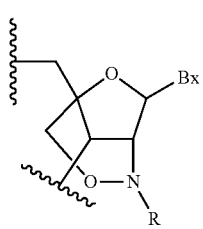

(E) 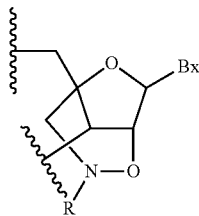

(F) 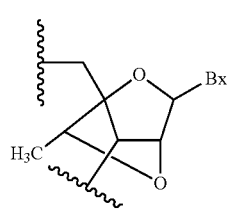

(G) 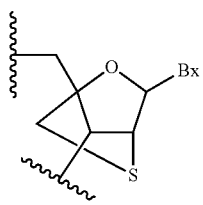

(H) 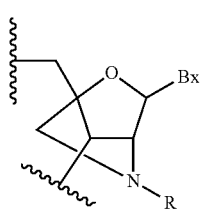

(I) 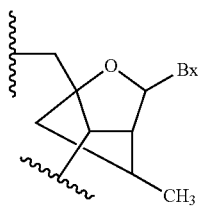

(J) 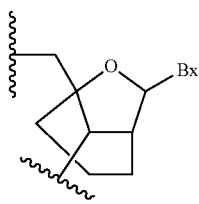

(K) 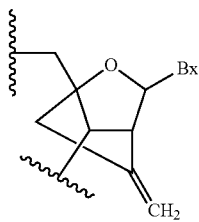

wherein Bx is the base moiety and R is, independently, H, a protecting group, $C_1$-$C_6$ alkyl or $C_1$-$C_6$ alkoxy.

As used herein, the term "modified tetrahydropyran nucleoside" or "modified THP nucleoside" means a nucleoside having a six-membered tetrahydropyran "sugar" substituted for the pentofuranosyl residue in normal nucleosides and can be referred to as a sugar surrogate. Modified THP nucleosides include, but are not limited to, what is referred to in the art as hexitol nucleic acid (HNA), anitol nucleic acid (ANA), manitol nucleic acid (MNA) (see Leumann, *Bioorg. Med. Chem.*, 2002, 10, 841-854) or fluoro HNA (F-HNA) having a tetrahydropyranyl ring system as illustrated below.

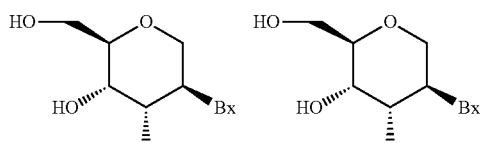

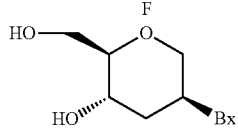

In certain embodiment, sugar surrogates are selected having the formula:

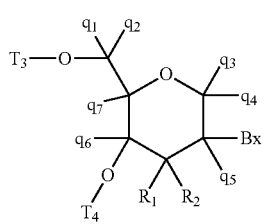

wherein:
Bx is a heterocyclic base moiety;
$T_3$ and $T_4$ are each, independently, an internucleoside linking group linking the tetrahydropyran nucleoside analog to the oligomeric compound or one of $T_3$ and $T_4$ is an internucleoside linking group linking the tetrahydropyran nucleoside analog to an oligomeric compound or oligonucleotide and the other of $T_3$ and $T_4$ is H, a hydroxyl protecting group, a linked conjugate group or a 5' or 3'-terminal group;
$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and
one of $R_1$ and $R_2$ is hydrogen and the other is selected from halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$ and CN, wherein X is O, S or $NJ_1$ and each $J_1$, $J_2$ and $J_3$ is, independently, H or $C_1$-$C_6$ alkyl.

In certain embodiments, $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides are provided wherein one of $R_1$ and $R_2$ is F. In certain embodiments, $R_1$ is fluoro and $R_2$ is H; $R_1$ is methoxy and $R_2$ is H, and $R_1$ is methoxyethoxy and $R_2$ is H.

In certain embodiments, sugar surrogates comprise rings having more than 5 atoms and more than one heteroatom. For example nucleosides comprising morpholino sugar moieties and their use in oligomeric compounds has been reported (see for example: Braasch et al., *Biochemistry*, 2002, 41, 4503-4510; and U.S. Pat. Nos. 5,698,685; 5,166, 315; 5,185,444; and 5,034,506). As used here, the term "morpholino" means a sugar surrogate having the following formula:

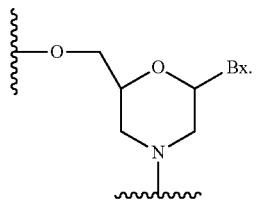

In certain embodiments, morpholinos may be modified, for example by adding or altering various substituent groups from the above morpholino structure. Such sugar surrogates are referred to herein as "modified morpholinos."

Combinations of modifications are also provided without limitation, such as 2'-F-5'-methyl substituted nucleosides (see PCT International Application WO 2008/101157 published on Aug. 21, 2008 for other disclosed 5',2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-$CH_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

In certain embodiments, antisense compounds comprise one or more modified cyclohexenyl nucleosides, which is a nucleoside having a six-membered cyclohexenyl in place of the pentofuranosyl residue in naturally occurring nucleosides. Modified cyclohexenyl nucleosides include, but are not limited to those described in the art (see for example commonly owned, published PCT Application WO 2010/036696, published on Apr. 10, 2010, Robeyns et al., *J. Am. Chem. Soc.*, 2008, 130(6), 1979-1984; Horvath et al., *Tetrahedron Letters*, 2007, 48, 3621-3623; Nauwelaerts et al., *J. Am. Chem. Soc.*, 2007, 129(30), 9340-9348; Gu et al., *Nucleosides, Nucleotides & Nucleic Acids*, 2005, 24(5-7), 993-998; Nauwelaerts et al., *Nucleic Acids Research*, 2005, 33(8), 2452-2463; Robeyns et al., *Acta Crystallographica, Section F: Structural Biology and Crystallization Communications*, 2005, F61(6), 585-586; Gu et al., *Tetrahedron*, 2004, 60(9), 2111-2123; Gu et al., *Oligonucleotides*, 2003, 13(6), 479-489; Wang et al., *J. Org. Chem.*, 2003, 68, 4499-4505; Verbeure et al., *Nucleic Acids Research*, 2001, 29(24), 4941-4947; Wang et al., *J. Org. Chem.*, 2001, 66, 8478-82; Wang et al., *Nucleosides, Nucleotides & Nucleic Acids*, 2001, 20(4-7), 785-788; Wang et al., *J. Am. Chem.*, 2000, 122, 8595-8602; Published PCT application, WO 06/047842; and Published PCT Application WO 01/049687; the text of each is incorporated by reference herein, in their entirety). Certain modified cyclohexenyl nucleosides have Formula X.

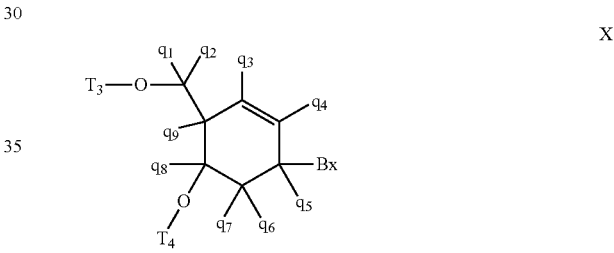

wherein independently for each of said at least one cyclohexenyl nucleoside analog of Formula X:
Bx is a heterocyclic base moiety;
$T_3$ and $T_4$ are each, independently, an internucleoside linking group linking the cyclohexenyl nucleoside analog to an antisense compound or one of $T_3$ and $T_4$ is an internucleoside linking group linking the tetrahydropyran nucleoside analog to an antisense compound and the other of $T_3$ and $T_4$ is H, a hydroxyl protecting group, a linked conjugate group, or a 5'- or 3'-terminal group; and
$q_1$, $q_2$, $q_3$, $q_4$, $q_5$, $q_6$, $q_7$, $q_8$ and $q_9$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or other sugar substituent group.

Many other monocyclic, bicyclic and tricyclic ring systems are known in the art and are suitable as sugar surrogates that can be used to modify nucleosides for incorporation into oligomeric compounds as provided herein (see for example review article: Leumann, Christian J. *Bioorg. & Med. Chem.*, 2002, 10, 841-854). Such ring systems can undergo various additional substitutions to further enhance their activity.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: $O[(CH_2)_nO]_mCH_3$, $O(CH_2)_nNH_2$, $O(CH_2)_nCH_3$, $O(CH_2)_nF$, $O(CH_2)_nONH_2$, $OCH_2C(=O)N(H)CH_3$, and $O(CH_2)_nON[(CH_2)_nCH_3]_2$, where n and m are from 1 to about 10. Other 2'-substituent groups can also be selected from: $C_1$-$C_{12}$ alkyl, substituted alkyl, alkenyl, alkynyl, alkaryl, aralkyl, O-alkaryl or O-aralkyl, SH, $SCH_3$, OCN, Cl, Br, CN, F, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an antisense compound, and other substituents having similar properties. In certain embodiments, modified nucleosides comprise a 2'-MOE side chain (Baker et al., *J. Biol. Chem.,* 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (Martin, *Helv. Chim. Acta,* 1995, 78, 486-504; Altmann et al., *Chimia,* 1996, 50, 168-176; Altmann et al., *Biochem. Soc. Trans.,* 1996, 24, 630-637; and Altmann et al., *Nucleosides Nucleotides,* 1997, 16, 917-926).

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring; and nucleosides with non-bridging 2' substituents, such as allyl, amino, azido, thio, O-allyl, O—$C_1$-$C_{10}$ alkyl, —$OCF_3$, O—$(CH_2)_2$—O—$CH_3$, 2'-$O(CH_2)_2SCH_3$, O—$(CH_2)_2$—O—$N(R_m)(R_n)$, or O—$CH_2$—C(=O)—$N(R_m)(R_n)$, where each $R_m$ and $R_n$ is, independently, H or substituted or unsubstituted $C_1$-$C_{10}$ alkyl. 2'-modified nucleosides may further comprise other modifications, for example at other positions of the sugar and/or at the nucleobase.

As used herein, "2'-F" refers to a nucleoside comprising a sugar comprising a fluoro group at the 2' position of the sugar ring.

As used herein, "2'-OMe" or "2'-$OCH_3$", "2'-O-methyl" or "2'-methoxy" each refers to a nucleoside comprising a sugar comprising an —$OCH_3$ group at the 2' position of the sugar ring.

As used herein, "MOE" or "2'-MOE" or "2'-$OCH_2CH_2OCH_3$" or "2'-O-methoxyethyl" each refers to a nucleoside comprising a sugar comprising a —$OCH_2CH_2OCH_3$ group at the 2' position of the sugar ring.

Methods for the preparations of modified sugars are well known to those skilled in the art. Some representative U.S. patents that teach the preparation of such modified sugars include without limitation, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,670,633; 5,700,920; 5,792,847 and 6,600,032 and International Application PCT/US2005/019219, filed Jun. 2, 2005 and published as WO 2005/121371 on Dec. 22, 2005, and each of which is herein incorporated by reference in its entirety.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

In nucleotides having modified sugar moieties, the nucleobase moieties (natural, modified or a combination thereof) are maintained for hybridization with an appropriate nucleic acid target.

In certain embodiments, antisense compounds comprise one or more nucleosides having modified sugar moieties. In certain embodiments, the modified sugar moiety is 2'-MOE. In certain embodiments, the 2'-MOE modified nucleosides are arranged in a gapmer motif. In certain embodiments, the modified sugar moiety is a bicyclic nucleoside having a (4'-CH(CH$_3$)—O-2') bridging group. In certain embodiments, the (4'-CH(CH$_3$)—O-2') modified nucleosides are arranged throughout the wings of a gapmer motif.

Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications may impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., *Antisense Research and Applications,* CRC Press, Boca Raton, 1993, pp. 276-278).

Additional modified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-aminoadenine, 8-azaguanine and 8-azaadenine, 7-deazaguanine and 7-deazaadenine and 3-deazaguanine and 3-deazaadenine.

Heterocyclic base moieties may include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and O-6 substituted purines, including 2 aminopropyladenine, 5-propynyluracil and 5-propynylcytosine.

In certain embodiments, antisense compounds targeted to an ApoCIII nucleic acid comprise one or more modified nucleobases. In certain embodiments, gap-widened antisense oligonucleotides targeted to an ApoCIII nucleic acid comprise one or more modified nucleobases. In certain embodiments, the modified nucleobase is 5-methylcytosine.

In certain embodiments, each cytosine is a 5-methylcytosine.

RNAi Compounds

In certain embodiments, antisense compounds are interfering RNA compounds (RNAi), which include double-stranded RNA compounds (also referred to as short-interfering RNA or siRNA) and single-stranded RNAi compounds (or ssRNA). Such compounds work at least in part through the RISC pathway to degrade and/or sequester a target nucleic acid (thus, include microRNA/microRNA-mimic compounds). In certain embodiments, antisense compounds comprise modifications that make them particularly suited for such mechanisms.

i. ssRNA Compounds

In certain embodiments, antisense compounds including those particularly suited for use as single-stranded RNAi compounds (ssRNA) comprise a modified 5'-terminal end. In certain such embodiments, the 5'-terminal end comprises a modified phosphate moiety. In certain embodiments, such modified phosphate is stabilized (e.g., resistant to degradation/cleavage compared to unmodified 5'-phosphate). In certain embodiments, such 5'-terminal nucleosides stabilize the 5'-phosphorous moiety. Certain modified 5'-terminal nucleosides may be found in the art, for example in WO/2011/139702.

In certain embodiments, the 5'-nucleoside of an ssRNA compound has Formula IIc:

IIc wherein:

$T_1$ is an optionally protected phosphorus moiety;

$T_2$ is an internucleoside linking group linking the compound of Formula IIc to the oligomeric compound;

A has one of the formulas:

$Q_1$ and $Q_2$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, substituted $C_2$-$C_6$ alkynyl or $N(R_3)(R_4)$;

$Q_3$ is O, S, $N(R_5)$ or $C(R_6)(R_7)$;

each $R_3$, $R_4$ $R_5$, $R_6$ and $R_7$ is, independently, H, $C_1$-$C_6$ alkyl, substituted $C_1$-$C_6$ alkyl or $C_1$-$C_6$ alkoxy;

$M_3$ is O, S, $NR_{14}$, $C(R_{15})(R_{16})$, $C(R_{15})(R_{16})C(R_{17})(R_{18})$, $C(R_{15})$=$C(R_{17})$, $OC(R_{15})(R_{16})$ or $OC(R_{15})(Bx_2)$;

$R_{14}$ is H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

$R_{15}$, $R_{16}$, $R_{17}$ and $R_{18}$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

$Bx_1$ is a heterocyclic base moiety;

or if $Bx_2$ is present then $Bx_2$ is a heterocyclic base moiety and $Bx_1$ is H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

$J_4$, $J_5$, $J_6$ and $J_7$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

or $J_4$ forms a bridge with one of $J_5$ or $J_7$ wherein said bridge comprises from 1 to 3 linked biradical groups selected from O, S, $NR_{19}$, $C(R_{20})(R_{21})$, $C(R_{20})$=$C(R_{21})$, $C[$=$C(R_{20})(R_{21})]$ and $C($=$O)$ and the other two of $J_5$, $J_6$ and $J_7$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

each $R_{19}$, $R_{20}$ and $R_{21}$ is, independently, H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

G is H, OH, halogen or O—$[C(R_8)(R_9)]_n$—$[(C$=$O)_m$—$X_1]_j$—Z;

each $R_8$ and $R_9$ is, independently, H, halogen, $C_1$-$C_6$ alkyl or substituted $C_1$-$C_6$ alkyl;

$X_1$ is O, S or $N(E_1)$;

Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to about 6;

m is 0 or 1;

j is 0 or 1;

each substituted group comprises one or more optionally protected substituent groups independently selected from halogen, $OJ_1$, $N(J_1)(J_2)$, =$NJ_1$, $SJ_1$, $N_3$, CN, $OC$(=$X_2$)$J_1$, $OC$(=$X_2$)—$N(J_1)(J_2)$ and $C$(=$X_2$)$N(J_1)(J_2)$;

$X_2$ is O, S or $NJ_3$;

each $J_1$, $J_2$ and $J_3$ is, independently, H or $C_1$-$C_6$ alkyl;

when j is 1 then Z is other than halogen or $N(E_2)(E_3)$; and wherein said oligomeric compound comprises from 8 to 40 monomeric subunits and is hybridizable to at least a portion of a target nucleic acid.

In certain embodiments, $M_3$ is O, CH=CH, $OCH_2$ or $OC(H)(Bx_2)$. In certain embodiments, $M_3$ is O.

In certain embodiments, $J_4$, $J_5$, $J_6$ and $J_7$ are each H. In certain embodiments, $J_4$ forms a bridge with one of $J_5$ or $J_7$.

In certain embodiments, A has one of the formulas:

wherein:

$Q_1$ and $Q_2$ are each, independently, H, halogen, $C_1$-$C_6$ alkyl, substituted $C_1$-$C_6$ alkyl, $C_1$-$C_6$ alkoxy or substituted $C_1$-$C_6$ alkoxy. In certain embodiments, $Q_1$ and $Q_2$ are each H. In certain embodiments, $Q_1$ and $Q_2$ are each, independently, H or halogen. In certain embodiments, $Q_1$ and $Q_2$ is H and the other of $Q_1$ and $Q_2$ is F, $CH_3$ or $OCH_3$.

In certain embodiments, $T_1$ has the formula:

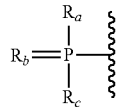

wherein:

$R_a$ and $R_c$ are each, independently, protected hydroxyl, protected thiol, $C_1$-$C_6$ alkyl, substituted $C_1$-$C_6$ alkyl, $C_1$-$C_6$ alkoxy, substituted $C_1$-$C_6$ alkoxy, protected amino or substituted amino; and $R_b$ is O or S. In certain embodiments, $R_b$ is O and $R_a$ and $R_c$ are each, independently, $OCH_3$, $OCH_2CH_3$ or $CH(CH_3)_2$.

In certain embodiments, G is halogen, $OCH_3$, $OCH_2F$, $OCHF_2$, $OCF_3$, $OCH_2CH_3$, $O(CH_2)_2F$, $OCH_2CHF_2$, $OCH_2CF_3$, $OCH_2$—CH═$CH_2$, $O(CH_2)_2$—$OCH_3$, $O(CH_2)_2$—$SCH_3$, $O(CH_2)_2$—$OCF_3$, $O(CH_2)_3$—$N(R_{10})(R_{11})$, $O(CH_2)_2$—$ON(R_{10})(R_{11})$, $O(CH_2)_2$—$O(CH_2)_2$—$N(R_{10})(R_{11})$, $OCH_2C(═O)$—$N(R_{10})(R_{11})$, $OCH_2C(═O)$—$N(R_{12})$—$(CH_2)_2$—$N(R_{10})(R_{11})$ or $O(CH_2)_2$—$N(R_{12})$—C($═NR_{13}$)[$N(R_{10})(R_{11})$] wherein $R_{10}$, $R_{11}$, $R_{12}$ and $R_{13}$ are each, independently, H or $C_1$-$C_6$ alkyl. In certain embodiments, G is halogen, $OCH_3$, $OCF_3$, $OCH_2CH_3$, $OCH_2CF_3$, $OCH_2$—CH═$CH_2$, $O(CH_2)_2$—$OCH_3$, $O(CH_2)_2$—$O(CH_2)_2$—$N(CH_3)_2$, $OCH_2C(═O)$—$N(H)CH_3$, $OCH_2C(═O)$—$N(H)$—$(CH_2)_2$—$N(CH_3)_2$ or $OCH_2$—$N(H)$—C($═NH$)$NH_2$. In certain embodiments, G is F, $OCH_3$ or $O(CH_2)_2$—$OCH_3$. In certain embodiments, G is $O(CH_2)_2$—$OCH_3$.

In certain embodiments, the 5'-terminal nucleoside has Formula IIe:

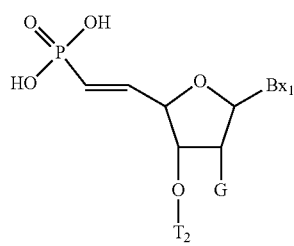

IIe

In certain embodiments, antisense compounds, including those particularly suitable for ssRNA comprise one or more type of modified sugar moieties and/or naturally occurring sugar moieties arranged along an oligonucleotide or region thereof in a defined pattern or sugar modification motif. Such motifs may include any of the sugar modifications discussed herein and/or other known sugar modifications.

In certain embodiments, the oligonucleotides comprise or consist of a region having uniform sugar modifications. In certain such embodiments, each nucleoside of the region comprises the same RNA-like sugar modification. In certain embodiments, each nucleoside of the region is a 2'-F nucleoside. In certain embodiments, each nucleoside of the region is a 2'-OMe nucleoside. In certain embodiments, each nucleoside of the region is a 2'-MOE nucleoside. In certain embodiments, each nucleoside of the region is a cEt nucleoside. In certain embodiments, each nucleoside of the region is an LNA nucleoside. In certain embodiments, the uniform region constitutes all or essentially all of the oligonucleotide. In certain embodiments, the region constitutes the entire oligonucleotide except for 1-4 terminal nucleosides.

In certain embodiments, oligonucleotides comprise one or more regions of alternating sugar modifications, wherein the nucleosides alternate between nucleotides having a sugar modification of a first type and nucleotides having a sugar modification of a second type. In certain embodiments, nucleosides of both types are RNA-like nucleosides. In certain embodiments the alternating nucleosides are selected from: 2'-OMe, 2'-F, 2'-MOE, LNA, and cEt. In certain embodiments, the alternating modifications are 2'-F and 2'-OMe. Such regions may be contiguous or may be interrupted by differently modified nucleosides or conjugated nucleosides.

In certain embodiments, the alternating region of alternating modifications each consist of a single nucleoside (i.e., the pattern is $(AB)_xA_y$ wherein A is a nucleoside having a sugar modification of a first type and B is a nucleoside having a sugar modification of a second type; x is 1-20 and y is 0 or 1). In certain embodiments, one or more alternating regions in an alternating motif includes more than a single nucleoside of a type. For example, oligonucleotides may include one or more regions of any of the following nucleoside motifs:

```
AABBAA;
ABBABB;
AABAAB;
ABBABAABB;
ABABAA;
AABABAB;
ABABAA;
ABBAABBABABAA;
BABBAABBABABAA;
or
ABABBAABBABABAA;
``` wherein A is a nucleoside of a first type and B is a nucleoside of a second type. In certain embodiments, A and B are each selected from 2'-F, 2'-OMe, BNA, and MOE.

In certain embodiments, oligonucleotides having such an alternating motif also comprise a modified 5' terminal nucleoside, such as those of formula IIc or IIe.

In certain embodiments, oligonucleotides comprise a region having a 2-2-3 motif. Such regions comprises the following motif:

-(A)$_2$-(B)$_x$-(A)$_2$-(C)$_y$-(A)$_3$- wherein: A is a first type of modified nucleoside;

B and C, are nucleosides that are differently modified than A, however, B and C may have the same or different modifications as one another;

x and y are from 1 to 15.

In certain embodiments, A is a 2'-OMe modified nucleoside. In certain embodiments, B and C are both 2'-F modified nucleosides. In certain embodiments, A is a 2'-OMe modified nucleoside and B and C are both 2'-F modified nucleosides.

In certain embodiments, oligonucleosides have the following sugar motif:

wherein:

Q is a nucleoside comprising a stabilized phosphate moiety. In certain embodiments, Q is a nucleoside having Formula IIc or IIe;

A is a first type of modified nucleoside;

B is a second type of modified nucleoside;

D is a modified nucleoside comprising a modification different from the nucleoside adjacent to it. Thus, if y is 0, then D must be differently modified than B and if y is 1, then D must be differently modified than A. In certain embodiments, D differs from both A and B.

X is 5-15;

Y is 0 or 1;

Z is 0-4.

In certain embodiments, oligonucleosides have the following sugar motif:

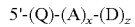

wherein:

Q is a nucleoside comprising a stabilized phosphate moiety. In certain embodiments, Q is a nucleoside having Formula IIc or IIe;

A is a first type of modified nucleoside;

D is a modified nucleoside comprising a modification different from A.

X is 11-30;

Z is 0-4.

In certain embodiments A, B, C, and D in the above motifs are selected from: 2'-OMe, 2'-F, 2'-MOE, LNA, and cEt. In certain embodiments, D represents terminal nucleosides. In certain embodiments, such terminal nucleosides are not designed to hybridize to the target nucleic acid (though one or more might hybridize by chance). In certain embodiments, the nucleobase of each D nucleoside is adenine, regardless of the identity of the nucleobase at the corresponding position of the target nucleic acid. In certain embodiments the nucleobase of each D nucleoside is thymine.

In certain embodiments, antisense compounds, including those particularly suited for use as ssRNA comprise modified internucleoside linkages arranged along the oligonucleotide or region thereof in a defined pattern or modified internucleoside linkage motif. In certain embodiments, oligonucleotides comprise a region having an alternating internucleoside linkage motif. In certain embodiments, oligonucleotides comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate internucleoside linkages. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least one block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

Oligonucleotides having any of the various sugar motifs described herein, may have any linkage motif. For example, the oligonucleotides, including but not limited to those described above, may have a linkage motif selected from non-limiting the table below:

| 5' most linkage | Central region | 3'-region |
| --- | --- | --- |
| PS | Alternating PO/PS | 6 PS |
| PS | Alternating PO/PS | 7 PS |
| PS | Alternating PO/PS | 8 PS | ii. siRNA Compounds

In certain embodiments, antisense compounds are double-stranded RNAi compounds (siRNA). In such embodiments, one or both strands may comprise any modification motif described above for ssRNA. In certain embodiments, ssRNA compounds may be unmodified RNA. In certain embodiments, siRNA compounds may comprise unmodified RNA nucleosides, but modified internucleoside linkages.

Several embodiments relate to double-stranded compositions wherein each strand comprises a motif defined by the location of one or more modified or unmodified nucleosides. In certain embodiments, compositions are provided comprising a first and a second oligomeric compound that are fully or at least partially hybridized to form a duplex region and further comprising a region that is complementary to and hybridizes to a nucleic acid target. It is suitable that such a composition comprise a first oligomeric compound that is an antisense strand having full or partial complementarity to a nucleic acid target and a second oligomeric compound that is a sense strand having one or more regions of complementarity to and forming at least one duplex region with the first oligomeric compound.

The compositions of several embodiments modulate gene expression by hybridizing to a nucleic acid target resulting in loss of its normal function. In some embodiments, the target nucleic acid is ApoCIII. In certain embodiment, the degradation of the targeted ApoCIII is facilitated by an activated RISC complex that is formed with compositions of the invention.

Several embodiments are directed to double-stranded compositions wherein one of the strands is useful in, for example, influencing the preferential loading of the opposite strand into the RISC (or cleavage) complex. The compositions are useful for targeting selected nucleic acid molecules and modulating the expression of one or more genes. In some embodiments, the compositions of the present invention hybridize to a portion of a target RNA resulting in loss of normal function of the target RNA.

Certain embodiments are drawn to double-stranded compositions wherein both the strands comprise a hemimer motif, a fully modified motif, a positionally modified motif or an alternating motif. Each strand of the compositions of the present invention can be modified to fulfill a particular role in for example the siRNA pathway. Using a different motif in each strand or the same motif with different chemical modifications in each strand permits targeting the antisense strand for the RISC complex while inhibiting the incorporation of the sense strand. Within this model, each strand can be independently modified such that it is enhanced for its particular role. The antisense strand can be modified at the 5'-end to enhance its role in one region of the RISC while the 3'-end can be modified differentially to enhance its role in a different region of the RISC.

The double-stranded oligonucleotide molecules can be a double-stranded polynucleotide molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. The double-stranded oligonucleotide molecules can be assembled from two separate oligonucleotides, where one strand is the sense strand and the other is the antisense strand, wherein the antisense and sense strands are self-complementary (i.e. each strand comprises nucleotide sequence that is complementary to nucleotide sequence in the other strand; such as where the antisense strand and sense strand form a duplex or double-stranded structure, for example wherein the double-stranded region is about 15 to about 30, e.g., about 15, 16, 17, 18, 19, 20, 21, 22, 23, 24, 25, 26, 27, 28, 29 or 30 base pairs; the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof (e.g., about 15 to about 25 or more nucleotides of the double-stranded oligonucleotide molecule are complementary to the target nucleic acid or a portion thereof). Alternatively, the double-stranded oligonucleotide is assembled from a single oligonucleotide, where the self-complementary sense and antisense regions of the siRNA are linked by means of a nucleic acid based or non-nucleic acid-based linker(s).

The double-stranded oligonucleotide can be a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof. The double-stranded oligonucleotide can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNAi.

In certain embodiments, the double-stranded oligonucleotide comprises separate sense and antisense sequences or regions, wherein the sense and antisense regions are covalently linked by nucleotide or non-nucleotide linkers molecules as is known in the art, or are alternately non-covalently linked by ionic interactions, hydrogen bonding, van der Waals interactions, hydrophobic interactions, and/or stacking interactions. In certain embodiments, the double-stranded oligonucleotide comprises nucleotide sequence that is complementary to nucleotide sequence of a target gene. In another embodiment, the double-stranded oligonucleotide interacts with nucleotide sequence of a target gene in a manner that causes inhibition of expression of the target gene.

As used herein, double-stranded oligonucleotides need not be limited to those molecules containing only RNA, but further encompasses chemically modified nucleotides and non-nucleotides. In certain embodiments, the short interfering nucleic acid molecules lack 2'-hydroxy (2'-OH) containing nucleotides. In certain embodiments short interfering nucleic acids optionally do not include any ribonucleotides (e.g., nucleotides having a 2'-OH group). Such double-stranded oligonucleotides that do not require the presence of ribonucleotides within the molecule to support RNAi can however have an attached linker or linkers or other attached or associated groups, moieties, or chains containing one or more nucleotides with 2'-OH groups. Optionally, double-stranded oligonucleotides can comprise ribonucleotides at about 5, 10, 20, 30, 40, or 50% of the nucleotide positions. As used herein, the term siRNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically modified siRNA, post-transcriptional gene silencing RNA (ptgsRNA), ssRNAi and others. In addition, as used herein, the term RNAi is meant to be equivalent to other terms used to describe sequence specific RNA interference, such as post transcriptional gene silencing, translational inhibition, or epigenetics. For example, double-stranded oligonucleotides can be used to epigenetically silence genes at both the post-transcriptional level and the pre-transcriptional level. In a non-limiting example, epigenetic regulation of gene expression by siRNA molecules of the invention can result from siRNA mediated modification of chromatin structure or methylation pattern to alter gene expression (see, for example, Verdel et al., 2004, Science, 303, 672-676; Pal-Bhadra et al., 2004, Science, 303, 669-672; Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237).

It is contemplated that compounds and compositions of several embodiments provided herein can target ApoCIII by a dsRNA-mediated gene silencing or RNAi mechanism, including, e.g., "hairpin" or stem-loop double-stranded RNA effector molecules in which a single RNA strand with self-complementary sequences is capable of assuming a double-stranded conformation, or duplex dsRNA effector molecules comprising two separate strands of RNA. In various embodiments, the dsRNA consists entirely of ribonucleotides or consists of a mixture of ribonucleotides and deoxynucleotides, such as the RNA/DNA hybrids disclosed, for example, by WO 00/63364, filed Apr. 19, 2000, or U.S. Ser. No. 60/130,377, filed Apr. 21, 1999. The dsRNA or dsRNA effector molecule may be a single molecule with a region of self-complementarity such that nucleotides in one segment of the molecule base pair with nucleotides in another segment of the molecule. In various embodiments, a dsRNA that consists of a single molecule consists entirely of ribonucleotides or includes a region of ribonucleotides that is complementary to a region of deoxyribonucleotides. Alternatively, the dsRNA may include two different strands that have a region of complementarity to each other.

In various embodiments, both strands consist entirely of ribonucleotides, one strand consists entirely of ribonucleotides and one strand consists entirely of deoxyribonucleotides, or one or both strands contain a mixture of ribonucleotides and deoxyribonucleotides. In certain embodiments, the regions of complementarity are at least 70, 80, 90, 95, 98, or 100% complementary to each other and to a target nucleic acid sequence. In certain embodiments, the region of the dsRNA that is present in a double-stranded conformation includes at least 19, 20, 21, 22, 23, 24, 25, 26, 27, 28, 29, 30, 50, 75, 100, 200, 500, 1000, 2000 or 5000 nucleotides or includes all of the nucleotides in a cDNA or other target nucleic acid sequence being represented in the dsRNA. In some embodiments, the dsRNA does not contain any single stranded regions, such as single stranded ends, or the dsRNA is a hairpin. In other embodiments, the dsRNA has one or more single stranded regions or overhangs. In certain embodiments, RNA/DNA hybrids include a DNA strand or region that is an antisense strand or region (e.g, has at least 70, 80, 90, 95, 98, or 100% complementarity to a target nucleic acid) and an RNA strand or region that is a sense strand or region (e.g, has at least 70, 80, 90, 95, 98, or 100% identity to a target nucleic acid), and vice versa.

In various embodiments, the RNA/DNA hybrid is made in vitro using enzymatic or chemical synthetic methods such as those described herein or those described in WO 00/63364, filed Apr. 19, 2000, or U.S. Ser. No. 60/130,377, filed Apr. 21, 1999. In other embodiments, a DNA strand synthesized in vitro is complexed with an RNA strand made in vivo or in vitro before, after, or concurrent with the transformation of the DNA strand into the cell. In yet other embodiments, the dsRNA is a single circular nucleic acid containing a sense and an antisense region, or the dsRNA includes a circular nucleic acid and either a second circular nucleic acid or a linear nucleic acid (see, for example, WO 00/63364, filed Apr. 19, 2000, or U.S. Ser. No. 60/130,377, filed Apr. 21, 1999.) Exemplary circular nucleic acids include lariat structures in which the free 5' phosphoryl group of a nucleotide becomes linked to the 2' hydroxyl group of another nucleotide in a loop back fashion.

In other embodiments, the dsRNA includes one or more modified nucleotides in which the 2' position in the sugar contains a halogen (such as fluorine group) or contains an alkoxy group (such as a methoxy group) which increases the half-life of the dsRNA in vitro or in vivo compared to the corresponding dsRNA in which the corresponding 2' position contains a hydrogen or an hydroxyl group. In yet other embodiments, the dsRNA includes one or more linkages between adjacent nucleotides other than a naturally-occurring phosphodiester linkage. Examples of such linkages include phosphoramide, phosphorothioate, and phosphorodithioate linkages. The dsRNAs may also be chemically modified nucleic acid molecules as taught in U.S. Pat. No. 6,673,661. In other embodiments, the dsRNA contains one or two capped strands, as disclosed, for example, by WO 00/63364, filed Apr. 19, 2000, or U.S. Ser. No. 60/130,377, filed Apr. 21, 1999.

In other embodiments, the dsRNA can be any of the at least partially dsRNA molecules disclosed in WO 00/63364, as well as any of the dsRNA molecules described in U.S. Provisional Application 60/399,998; and U.S. Provisional Application 60/419,532, and PCT/US2003/033466, the teaching of which is hereby incorporated by reference. Any of the dsRNAs may be expressed in vitro or in vivo using the methods described herein or standard methods, such as those described in WO 00/63364.

Compositions and Methods for Formulating Pharmaceutical Compositions

Antisense compounds may be admixed with pharmaceutically acceptable active or inert substance for the preparation of pharmaceutical compositions or formulations. Compositions and methods for the formulation of pharmaceutical compositions are dependent upon a number of criteria, including, but not limited to, route of administration, extent of disease, or dose to be administered.

Antisense compounds targeted to an ApoCIII nucleic acid can be utilized in pharmaceutical compositions by combining the antisense compound with a suitable pharmaceutically acceptable diluent or carrier.

In certain embodiments, the "pharmaceutical carrier" or "excipient" is a pharmaceutically acceptable solvent, suspending agent or any other pharmacologically inert vehicle for delivering one or more nucleic acids to an animal. The excipient can be liquid or solid and can be selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipients, which do not deleteriously react with nucleic acids, suitable for parenteral or non-parenteral administration can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to an ApoCIII nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or an oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression of ApoCIII nucleic acids or proteins can be tested in vitro in a variety of cell types. Cell types used for such analyses are available from commercial vendors (e.g. American Type Culture Collection, Manassas, Va.; Zen-Bio, Inc., Research Triangle Park, N.C.; Clonetics Corporation, Walkersville, Md.) and cells are cultured according to the vendor's instructions using commercially available reagents (e.g. Invitrogen Life Technologies, Carlsbad, Calif.). Illustrative cell types include, but are not limited to, HepG2 cells, Hep3B cells, Huh7 (hepatocellular carcinoma) cells, primary hepatocytes, A549 cells, GM04281 fibroblasts and LLC-MK2 cells.

In Vitro Testing of Antisense Oligonucleotides

Described herein are methods for treatment of cells with antisense oligonucleotides, which can be modified appropriately for treatment with other antisense compounds.

In general, cells are treated with antisense oligonucleotides when the cells reach approximately 60-80% confluence in culture.

One reagent commonly used to introduce antisense oligonucleotides into cultured cells includes the cationic lipid transfection reagent LIPOFECTIN® (Invitrogen, Carlsbad, Calif.). Antisense oligonucleotides are mixed with LIPOFECTIN® in OPTI-MEM® 1 (Invitrogen, Carlsbad, Calif.) to achieve the desired final concentration of antisense oligonucleotide and a LIPOFECTIN® concentration that typically ranges 2 to 12 ug/mL per 100 nM antisense oligonucleotide.

Another reagent used to introduce antisense oligonucleotides into cultured cells includes LIPOFECTAMINE 2000® (Invitrogen, Carlsbad, Calif.). Antisense oligonucleotide is mixed with LIPOFECTAMINE 2000® in OPTI-MEM® 1 reduced serum medium (Invitrogen, Carlsbad, Calif.) to achieve the desired concentration of antisense oligonucleotide and a LIPOFECTAMINE® concentration that typically ranges 2 to 12 ug/mL per 100 nM antisense oligonucleotide.

Another reagent used to introduce antisense oligonucleotides into cultured cells includes Cytofectin® (Invitrogen, Carlsbad, Calif.). Antisense oligonucleotide is mixed with Cytofectin® in OPTI-MEM® 1 reduced serum medium (Invitrogen, Carlsbad, Calif.) to achieve the desired concentration of antisense oligonucleotide and a Cytofectin® concentration that typically ranges 2 to 12 ug/mL per 100 nM antisense oligonucleotide.

Another reagent used to introduce antisense oligonucleotides into cultured cells includes Oligofectamine™ (Invitrogen Life Technologies, Carlsbad, Calif.). Antisense oligonucleotide is mixed with Oligofectamine™ in Opti-MEM™-1 reduced serum medium (Invitrogen Life Technologies, Carlsbad, Calif.) to achieve the desired concentration of oligonucleotide with an Oligofectamine™ to oligonucleotide ratio of approximately 0.2 to 0.8 µL per 100 nM.

Another reagent used to introduce antisense oligonucleotides into cultured cells includes FuGENE 6 (Roche Diagnostics Corp., Indianapolis, Ind.). Antisense oligomeric compound was mixed with FuGENE 6 in 1 mL of serum-free RPMI to achieve the desired concentration of oligonucleotide with a FuGENE 6 to oligomeric compound ratio of 1 to 4 µL of FuGENE 6 per 100 nM.

Another technique used to introduce antisense oligonucleotides into cultured cells includes electroporation (Sambrook and Russell in *Molecular Cloning. A Laboratory Manual.* Third Edition. Cold Spring Harbor Laboratory Press, Cold Spring Harbor, N.Y. 2001).

Cells are treated with antisense oligonucleotides by routine methods. Cells are typically harvested 16-24 hours after antisense oligonucleotide treatment, at which time RNA or protein levels of target nucleic acids are measured by methods known in the art and described herein (Sambrook and Russell in *Molecular Cloning. A Laboratory Manual.* Third Edition. Cold Spring Harbor Laboratory Press, Cold Spring Harbor, N.Y. 2001). In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art (Sambrook and Russell in *Molecular Cloning. A Laboratory Manual.* Third Edition. Cold Spring Harbor Laboratory Press, Cold Spring Harbor, N.Y. 2001). Antisense oligonucleotides are typically used at concentrations ranging from 1 nM to 300 nM when transfected with LIPOFECTAMINE2000® (Invitrogen, Carlsbad, Calif.), Lipofectin® (Invitrogen, Carlsbad, Calif.) or Cytofectin™ (Genlantis, San Diego, Calif.). Antisense oligonucleotides are used at higher concentrations ranging from 625 to 20,000 nM when transfected using electroporation.

RNA Isolation

RNA analysis can be performed on total cellular RNA or poly(A)+mRNA. Methods of RNA isolation are well known in the art (Sambrook and Russell in *Molecular Cloning. A Laboratory Manual.* Third Edition. Cold Spring Harbor Laboratory Press, Cold Spring Harbor, N.Y. 2001). RNA is prepared using methods well known in the art, for example, using the TRIZOL® Reagent (Invitrogen, Carlsbad, Calif.) according to the manufacturer's recommended protocols.

Analysis of Inhibition of Target Levels or Expression

Inhibition of levels or expression of an ApoCIII nucleic acid can be assayed in a variety of ways known in the art (Sambrook and Russell in *Molecular Cloning. A Laboratory Manual*. Third Edition. Cold Spring Harbor Laboratory Press, Cold Spring Harbor, N.Y. 2001). For example, target nucleic acid levels can be quantitated by, e.g., Northern blot analysis, competitive polymerase chain reaction (PCR), or quantitative real-time PCR. RNA analysis can be performed on total cellular RNA or poly(A)+mRNA. Methods of RNA isolation are well known in the art. Northern blot analysis is also routine in the art. Quantitative real-time PCR can be conveniently accomplished using the commercially available ABI PRISM® 7600, 7700, or 7900 Sequence Detection System, available from PE-Applied Biosystems, Foster City, Calif. and used according to manufacturer's instructions.

Quantitative Real-Time PCR Analysis of Target RNA Levels

Quantitation of target RNA levels may be accomplished by quantitative real-time PCR using the ABI PRISM® 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, Calif.). RT and real-time-PCR reactions are carried out by methods well known to those skilled in the art.

Gene (or RNA) target quantities obtained by real time PCR can be normalized using either the expression level of a gene whose expression is constant, such as cyclophilin A, or by quantifying total RNA using RIBOGREEN® (Invitrogen, Inc. Carlsbad, Calif.). Cyclophilin A expression is quantified by real time PCR, by being run simultaneously with the target, multiplexing, or separately. Total RNA is quantified using RIBOGREEN® RNA quantification reagent (Invitrogen, Inc. Carlsbad, Calif.). Methods of RNA quantification by RIBOGREEN® are taught in Jones, L. J., et al, (Analytical Biochemistry, 1998, 265, 368-374). A CYTOFLUOR® 4000 instrument (PE Applied Biosystems, Foster City, Calif.) is used to measure RIBOGREEN® fluorescence.

Probes and primers are designed to hybridize to an ApoCIII nucleic acid. Methods for designing real-time PCR probes and primers are well known in the art, and may include the use of software such as PRIMER EXPRESS® Software (Applied Biosystems, Foster City, Calif.).

Gene target quantities obtained by RT, real-time PCR can use either the expression level of GAPDH or Cyclophilin A, genes whose expression are constant, or by quantifying total RNA using RiboGreen™ (Molecular Probes, Inc. Eugene, Oreg.). GAPDH or Cyclophilin A expression can be quantified by RT, real-time PCR, by being run simultaneously with the target, multiplexing, or separately. Total RNA was quantified using RiboGreen™ RNA quantification reagent (Molecular Probes, Inc. Eugene, Oreg.).

Analysis of Protein Levels

Antisense inhibition of ApoCIII nucleic acids can be assessed by measuring ApoCIII protein levels. Protein levels of ApoCIII can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS) (Sambrook and Russell in *Molecular Cloning. A Laboratory Manual*. Third Edition. Cold Spring Harbor Laboratory Press, Cold Spring Harbor, N.Y. 2001). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Antibodies useful for the detection of human and mouse ApoCIII are commercially available.

In Vivo Testing of Antisense Compounds

Antisense compounds, for example, antisense oligonucleotides, are tested in animals to assess their ability to inhibit expression of ApoCIII and produce phenotypic changes. Testing can be performed in normal animals, or in experimental disease models. For administration to animals, antisense oligonucleotides are formulated in a pharmaceutically acceptable diluent, such as phosphate-buffered saline. Administration includes parenteral routes of administration. Calculation of antisense oligonucleotide dosage and dosing frequency depends upon factors such as route of administration and animal body weight. Following a period of treatment with antisense oligonucleotides, RNA is isolated from tissue and changes in ApoCIII nucleic acid expression are measured. Changes in ApoCIII protein levels are also measured.

Certain Indications

Novel effects of ApoCIII inhibition in patients with Fredrickson Type I dyslipidemia, FCS, LPLD, have been identified and disclosed herein. The example disclosed hereinbelow disclose surprising reductions in TG and increases in HDL among other biomarkers in Fredrickson Type I dyslipidemia, FCS, LPLD, patients who have little or no detectable LPL activity, Without being bound by any particular theory, two potential explanations for the surprising results are discussed. First, inhibiting ApoCIII may activate residual LPL activity in the Fredrickson Type I dyslipidemia, FCS, LPLD, patients. This is not a very likely explanation as these patients have little to no detectable LPL activity while ApoCIII inhibition has profoundly affected TG and HDL levels. Second, and more likely, is that ApoCIII inhibits clearance of TG particles mediated by apoE-mediated receptors such as the low density lipoprotein receptor-related protein 1 (LRP1) or Syndecan 1. Once ApoCIII is removed from VLDL and chylomicron particles, they become more amenable to uptake by the liver. Indeed, these receptor mediated clearance mechanisms may significantly contribute to the clinically observed phenotype (e.g., substantial TG lowering) observed in the Fredrickson Type I dyslipidemia, FCS, LPLD, patients treated with an ApoCIII inhibitor.

In certain embodiments, provided herein are methods of treating a subject with Fredrickson Type I dyslipidemia, FCS, LPLD, comprising administering one or more pharmaceutical compositions as described herein. In certain embodiments, the pharmaceutical composition comprises an antisense compound targeted to an ApoCIII.

In certain embodiments, administration of an antisense compound targeted to an ApoCIII nucleic acid to a subject with Fredrickson Type I dyslipidemia, FCS, LPLD, results in reduction of ApoCIII expression by at least about 15, 20, 25, 30, 35, 40, 45, 50, 55, 60, 65, 70, 75, 80, 85, 90, 95 or 99%, or a range defined by any two of these values. In certain embodiments, ApoCIII expression is reduced to ≤50 mg/L, ≤60 mg/L, ≤70 mg/L, ≤80 mg/L, ≤90 mg/L, ≤100 mg/L, ≤110 mg/L, ≤120 mg/L, ≤130 mg/L, ≤140 mg/L, ≤150 mg/L, ≤160 mg/L, ≤170 mg/L, ≤180 mg/L, ≤190 mg/L or ≤200 mg/L.

In certain embodiments, the subject has a disease or disorder related to Fredrickson Type I dyslipidemia, FCS, LPLD. In certain embodiments the disease or disorder is a cardiovascular or metabolic disease or disorder. In certain embodiments, the disease is pancreatitis.

In certain embodiments, the cardiovascular disease include, but are not limited to, aneurysm, angina, arrhythmia, atherosclerosis, cerebrovascular disease, coronary heart disease, hypertension, dyslipidemia, hyperlipidemia, hypertriglyceridemia, hypercholesterolemia, stroke and the like. In certain embodiments, the dyslipidemia is chylomicronemia (e.g., FCS) or hypertriglyceridemia. In certain embodiments, the disease is pancreatitis caused by dyslipidemia.

In certain embodiments, the metabolic disease or disorder include, but are not limited to, hyperglycemia, prediabetes, diabetes (type I and type II), obesity, insulin resistance, metabolic syndrome and diabetic dyslipidemia.

In certain embodiments, compounds targeted to ApoCIII as described herein modulate physiological markers or phenotypes of pancreatitis, a cardiovascular or a metabolic disease or disorder in a subject with Fredrickson Type I dyslipidemia, FCS, LPLD. In certain of the experiments, the compounds can increase or decrease physiological markers or phenotypes compared to untreated animals. In certain embodiments, the increase or decrease in physiological markers or phenotypes is associated with inhibition of ApoCIII by the compounds described herein.

In certain embodiments, physiological markers or phenotype of a cardiovascular disease or disorder can be quantifiable. For example, TG or HDL levels can be measured and quantified by, for example, standard lipid tests. In certain embodiments, physiological markers or phenotypes such as HDL can be increased by about 5, 10, 15, 20, 25, 30, 35, 40, 45, 50, 55, 60, 65, 70, 75, 80, 85, 90, 95 or 99%, or a range defined by any two of these values. In certain embodiments, physiological markers phenotypes such as TG (postprandial or fasting) can be decreased by about 5, 10, 15, 20, 25, 30, 35, 40, 45, 50, 55, 60, 65, 70, 75, 80, 85, 90, 95 or 99%, or a range defined by any two of these values. In certain embodiments, TG (postprandial or fasting) is reduced to ≤100 mg/dL, ≤110 mg/dL, ≤120 mg/dL, ≤130 mg/dL, ≤140 mg/dL, ≤150 mg/dL, ≤160 mg/dL, ≤170 mg/dL, ≤180 mg/dL, ≤190 mg/dL, ≤200 mg/dL, ≤210 mg/dL, ≤220 mg/dL, ≤230 mg/dL, ≤240 mg/dL, ≤250 mg/dL, ≤260 mg/dL, ≤270 mg/dL, ≤280 mg/dL, ≤290 mg/dL, ≤300 mg/dL, ≤350 mg/dL, ≤400 mg/dL, ≤450 mg/dL, ≤500 mg/dL, ≤550 mg/dL, ≤600 mg/dL, ≤650 mg/dL, ≤700 mg/dL, ≤750 mg/dL, ≤800 mg/dL, ≤850 mg/dL, ≤900 mg/dL, ≤950 mg/dL, ≤1000 mg/dL, ≤1100 mg/dL, ≤1200 mg/dL, ≤1300 mg/dL, ≤1400 mg/dL, ≤1500 mg/dL, ≤1600 mg/dL, ≤1700 mg/dL, ≤1800 mg/dL or ≤1900 mg/dL.

In certain embodiments, physiological markers or phenotypes of a metabolic disease or disorder can be quantifiable. For example, glucose levels or insulin resistance can be measured and quantified by standard tests known in the art. In certain embodiments, physiological markers or phenotypes such as glucose levels or insulin resistance can be decreased by about 5, 10, 15, 20, 25, 30, 35, 40, 45, 50, 55, 60, 65, 70, 75, 80, 85, 90, 95 or 99%, or a range defined by any two of these values. In certain embodiments, physiological markers phenotypes such as insulin sensitivity can be increased by about 5, 10, 15, 20, 25, 30, 35, 40, 45, 50, 55, 60, 65, 70, 75, 80, 85, 90, 95 or 99%, or a range defined by any two of these values.

Also, provided herein are methods for preventing, treating or ameliorating a symptom associated with a disease or disorder in a subject with Fredrickson Type I dyslipidemia, FCS, LPLD with a compound described herein. In certain embodiments, provided is a method for reducing the rate of onset of a symptom associated with a disease associated with Fredrickson Type I dyslipidemia, FCS, LPLD. In certain embodiments, provided is a method for reducing the severity of a symptom associated with Fredrickson Type I dyslipidemia, FCS, LPLD. In such embodiments, the methods comprise administering to an individual with Fredrickson Type I dyslipidemia a therapeutically effective amount of a compound targeted to an ApoCIII nucleic acid. In certain embodiments the disease or disorder is pancreatitis or a cardiovascular or metabolic disease or disorder.

Cardiovascular diseases or disorders are characterized by numerous physical symptoms. Any symptom known to one of skill in the art to be associated with a cardiovascular disease can be prevented, treated, ameliorated or otherwise modulated as set forth in the methods described herein. In certain embodiments, the symptom can be any of, but not limited to, angina, chest pain, shortness of breath, palpitations, weakness, dizziness, nausea, sweating, tachycardia, bradycardia, arrhythmia, atrial fibrillation, swelling in the lower extremities, cyanosis, fatigue, fainting, numbness of the face, numbness of the limbs, claudication or cramping of muscles, bloating of the abdomen or fever.

Metabolic diseases or disorders are characterized by numerous physical symptoms. Any symptom known to one of skill in the art to be associated with a metabolic disorder can be prevented, treated, ameliorated or otherwise modulated as set forth in the methods described herein. In certain embodiments, the symptom can be any of, but not limited to, excessive urine production (polyuria), excessive thirst and increased fluid intake (polydipsia), blurred vision, unexplained weight loss and lethargy.

Pancreatitis is characterized by numerous physical symptoms. Any symptom known to one of skill in the art to be associated with a pancreatitis can be prevented, treated, ameliorated or otherwise modulated as set forth in the methods described herein. In certain embodiments, the symptom can be any of, but not limited to, abdominal pain, vomiting, nausea, and abdominal sensitivity to pressure.

In certain embodiments, provided are methods of treating a subject with Fredrickson Type I dyslipidemia, FCS, LPLD, comprising administering a therapeutically effective amount of one or more pharmaceutical compositions as described herein. In certain embodiments, administration of a therapeutically effective amount of an antisense compound targeted to an ApoCIII nucleic acid is accompanied by monitoring of ApoCIII levels or disease markers associated with Fredrickson Type I dyslipidemia, FCS, LPLD, to determine a subject's response to the antisense compound. A subject's response to administration of the antisense compound is used by a physician to determine the amount and duration of therapeutic intervention.

In certain embodiments, pharmaceutical compositions comprising an antisense compound targeted to ApoCIII are used for the preparation of a medicament for treating a subject with Fredrickson Type I dyslipidemia, FCS, LPLD.

Administration

The compounds or pharmaceutical compositions of the present invention can be administered in a number of ways depending upon whether local or systemic treatment is desired and upon the area to be treated. Administration can be oral or parenteral.

In certain embodiments, the compounds and compositions as described herein are administered parenterally. Parenteral administration includes intravenous, intra-arterial, subcutaneous, intraperitoneal or intramuscular injection or infusion.

In certain embodiments, parenteral administration is by infusion. Infusion can be chronic or continuous or short or intermittent. In certain embodiments, infused pharmaceutical agents are delivered with a pump. In certain embodiments, the infusion is intravenous.

In certain embodiments, parenteral administration is by injection. The injection can be delivered with a syringe or a pump. In certain embodiments, the injection is a bolus injection. In certain embodiments, the injection is administered directly to a tissue or organ. In certain embodiments, parenteral administration is subcutaneous.

In certain embodiments, formulations for parenteral administration can include sterile aqueous solutions which can also contain buffers, diluents and other suitable additives such as, but not limited to, penetration enhancers, carrier compounds and other pharmaceutically acceptable carriers or excipients.

In certain embodiments, formulations for oral administration of the compounds or compositions of the invention can include, but is not limited to, pharmaceutical carriers, excipients, powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders can be desirable. In certain embodiments, oral formulations are those in which compounds of the invention are administered in conjunction with one or more penetration enhancers, surfactants and chelators.

Dosing

In certain embodiments, pharmaceutical compositions are administered according to a dosing regimen (e.g., dose, dose frequency, and duration) wherein the dosing regimen can be selected to achieve a desired effect. The desired effect can be, for example, reduction of ApoCIII or the prevention, reduction, amelioration or slowing the progression of a disease or condition associated with Fredrickson Type I dyslipidemia, FCS, LPLD.

In certain embodiments, the variables of the dosing regimen are adjusted to result in a desired concentration of pharmaceutical composition in a subject. "Concentration of pharmaceutical composition" as used with regard to dose regimen can refer to the compound, oligonucleotide, or active ingredient of the pharmaceutical composition. For example, in certain embodiments, dose and dose frequency are adjusted to provide a tissue concentration or plasma concentration of a pharmaceutical composition at an amount sufficient to achieve a desired effect.

Dosing is dependent on severity and responsiveness of the disease state to be treated, with the course of treatment lasting from several days to several months, or until a cure is effected or a diminution of the disease state is achieved. Dosing is also dependent on drug potency and metabolism. In certain embodiments, dosage is from 0.01 µg to 100 mg per kg of body weight, or within a range of 0.001 mg-1000 mg dosing, and may be given once or more daily, weekly, monthly or yearly, or even once every 2 to 20 years. Following successful treatment, it may be desirable to have the patient undergo maintenance therapy to prevent the recurrence of the disease state, wherein the oligonucleotide is administered in maintenance doses, ranging from 0.01 µg to 100 mg per kg of body weight, once or more daily, to once every 20 years or ranging from 0.001 mg to 1000 mg dosing.

Certain Combination Therapies

In certain embodiments, a first agent comprising the compound described herein is co-administered with one or more secondary agents. In certain embodiments, such second agents are designed to treat the same disease, disorder, or condition as the first agent described herein. In certain embodiments, such second agents are designed to treat a different disease, disorder, or condition as the first agent described herein. In certain embodiments, a first agent is designed to treat an undesired side effect of a second agent. In certain embodiments, second agents are co-administered with the first agent to treat an undesired effect of the first agent. In certain embodiments, such second agents are designed to treat an undesired side effect of one or more pharmaceutical compositions as described herein. In certain embodiments, second agents are co-administered with the first agent to produce a combinational effect. In certain embodiments, second agents are co-administered with the first agent to produce a synergistic effect. In certain embodiments, the co-administration of the first and second agents permits use of lower dosages than would be required to achieve a therapeutic or prophylactic effect if the agents were administered as independent therapy. In certain embodiments, the first agent is administered to a subject that has failed or become non-responsive to a second agent. In certain embodiments, the first agent is administered to a subject in replacement of a second agent.

In certain embodiments, one or more compositions described herein and one or more other pharmaceutical agents are administered at the same time. In certain embodiments, one or more compositions of the invention and one or more other pharmaceutical agents are administered at different times. In certain embodiments, one or more compositions described herein and one or more other pharmaceutical agents are prepared together in a single formulation. In certain embodiments, one or more compositions described herein and one or more other pharmaceutical agents are prepared separately.

In certain embodiments, second agents include, but are not limited to, ApoCIII lowering agent, DGAT1 inhibitor, LPL raising agent, cholesterol lowering agent, non-HDL lipid lowering (e.g., LDL) agent, HDL raising agent, fish oil, niacin (nicotinic acid), fibrate, statin, DCCR (salt of diazoxide), glucose-lowering agent and/or anti-diabetic agents. In certain embodiments, the first agent is administered in combination with the maximally tolerated dose of the second agent. In certain embodiments, the first agent is administered to a subject that fails to respond to a maximally tolerated dose of the second agent.

Examples of ApoCIII lowering agents include an ApoCIII antisense oligonucleotide different from the first agent, fibrate or an Apo B antisense oligonucleotide.

An example of a DGAT1 inhibitor is LCQ908 (Novartis Pharmaceuticals) currently being tested in a Phase 3 clinical trial for treating Familial Chylomicronemia Syndrome (FCS).

LPL raising agents include gene therapy agents that raise the level of LPL. Examples of such agents include copies of normal genes that supplement the lack of the normal gene. For example, Glybera® raises LPL levels by providing normal copies of the LPL gene to supplement a lack of the normal LPL gene. In other examples, the LPL raising agent includes normal copies of ApoC-II, GPIHBP1, APOA5, LMF1 or other genes that, when mutated, can lead to dysfunctional LPL. In certain embodiments, the combination of the first agent (e.g., ApoCIII ASO) and the second agent (e.g., Glybera) provides an additive or synergistic effect. In certain embodiments, the first agent (e.g., ApoCIII ASO) is administered to a subject that has failed or become non-responsive to a second agent (e.g., Glybera®).

Examples of glucose-lowering and/or anti-diabetic agents include, but is not limited to, a therapeutic lifestyle change, PPAR agonist, a dipeptidyl peptidase (IV) inhibitor, a GLP-1 analog, insulin or an insulin analog, an insulin secretagogue, a SGLT2 inhibitor, a human amylin analog, a biguanide, an alpha-glucosidase inhibitor, metformin, sulfonylurea, rosiglitazone, meglitinide, thiazolidinedione, alpha-glucosidase inhibitor and the like. The sulfonylurea can be acetohexamide, chlorpropamide, tolbutamide, tolazamide, glimepiride, a glipizide, a glyburide, or a gliclazide. The meglitinide can be nateglinide or repaglinide. The thiazolidinedione can be pioglitazone or rosiglitazone. The alpha-glucosidase can be acarbose or miglitol.

The cholesterol or lipid lowering therapy can include, but is not limited to, a therapeutic lifestyle change, statins, bile acids sequestrants, nicotinic acid and fibrates. The statins can be atorvastatin, fluvastatin, lovastatin, pravastatin, rosuvastatin and simvastatin and the like. The bile acid sequestrants can be colesevelam, cholestyramine, colestipol and the like. The fibrates can be gemfibrozil, fenofibrate, clofibrate and the like. The therapeutic lifestyle change can be dietary fat restriction.

HDL increasing agents include cholesteryl ester transfer protein (CETP) inhibiting drugs (such as Torcetrapib), peroxisome proliferation activated receptor agonists, Apo-A1, Pioglitazone and the like.

Certain Treatment Populations

Some types of hypertriglyceridemia can be characterized by the Fredrickson classification system or by the classification system described by Tremblay (Tremblay et al., J Clin Lipidol, 2011, 5:37-44). In certain embodiments, the compounds, compositions and methods described herein are useful in treating subjects with Fredrickson Type I dyslipidemia, FCS, LPLD.

Subjects with Fredrickson Type I dyslipidemia, FCS, LPLD, are at a significant risk of pancreatitis, cardiovascular and metabolic disease. For these subjects, recurrent pancreatitis is the most debilitating and potentially lethal complication; other sequalae include increased tendency for atherosclerosis and diabetes.

Fredrickson Type I, FCS, LPLD, subjects lack a significant amount of functionally active LPL. ApoCIII plays an important role in TG metabolism and is an independent risk factor for cardiovascular disease in subjects with functional or partially functional LPL. ApoCIII is currently in clinical trials to treat non-Fredrickson Type I hypertriglyceridemia subjects. However, as ApoCIII pathway is thought to work through the LPL pathway, inhibition of ApoCIII has not been considered as a treatment option for Fredrickson Type I, FCS, LPLD, subjects.

ApoCIII inhibition, as shown herein, unexpectedly decreases TG levels and/or raises HDL levels in Fredrickson Type I dyslipidemic, FCS, LPLD, subjects. The decrease in TG and/or increase in HDL can, in turn, prevent, treat, delay or ameliorate a disease, disorder, or symptom thereof, associated with Fredrickson Type I dyslipidemia, FCS, LPLD.

Certain Compounds

We have previously disclosed compositions comprising antisense compounds targeting ApoCIII and methods for inhibiting ApoCIII by the antisense compounds in US 20040208856 (U.S. Pat. No. 7,598,227), US 20060264395 (U.S. Pat. No. 7,750,141), WO 2004/093783 and WO 2012/149495, all incorporated-by-reference herein. In these applications, a series of antisense compounds was designed to target different regions of the human ApoCIII RNA, using published sequences (nucleotides 6238608 to 6242565 of GenBank accession number NT_035088.1, representing a genomic sequence, incorporated herein as SEQ ID NO: 4, and GenBank accession number NM_000040.1, incorporated herein as SEQ ID NO: 1). The compounds were chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-O-(2-methoxyethyl) nucleotides, also known as (2'-MOE) nucleotides. The internucleoside (backbone) linkages are phosphorothioate (P=S) throughout the oligonucleotide. All cytosine residues are 5-methylcytosines.

The antisense compounds were analyzed for their effect on human ApoCIII mRNA levels in HepG2 cells by quantitative real-time PCR. Several compounds demonstrated at least 45% inhibition of ApoCIII mRNA and are therefore preferred. Several compounds demonstrated at least 50% inhibition of human ApoCIII mRNA and are therefore preferred. Several compounds demonstrated at least 60% inhibition of human ApoCIII mRNA and are therefore preferred. Several compounds demonstrated at least 70% inhibition of human ApoCIII mRNA and are therefore preferred. Several compounds demonstrated at least 80% inhibition of human ApoCIII mRNA and are therefore preferred. Several compounds demonstrated at least 90% inhibition of human ApoCIII mRNA and are therefore preferred.

The target regions to which these preferred antisense compounds are complementary are referred to as "preferred target segments" and are therefore preferred for targeting by antisense compounds.

EXAMPLES

Non-Limiting Disclosure and Incorporation by Reference

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1

ISIS 304801 Clinical Trial

As described herein, an open label study was performed on patients with Fredrickson Type I dyslipidemia, FCS, LPLD, to evaluate the response to, and the pharmacodynamic effects of, the Study Drug ISIS 304801. ISIS 304801 was previously disclosed in U.S. Pat. No. 7,598,227 and has the sequence 5'-AGCTTCTTGTCCAGCTTTAT-3' (SEQ ID NO: 3) starting at position 508 on SEQ ID NO: 1 (GENBANK Accession No. NM_000040.1) or starting at position 3139 on SEQ ID NO: 2 (GENBANK Accession NT_033899.8 truncated from nucleotides 20262640 to 20266603). ISIS 304801 has a 5-10-5 MOE gapmer motif comprising a gap segment consisting of 10 linked deoxynucleosides, a 5' wing segment consisting of 5 linked nucleosides, a 3' wing segment consisting 5 linked nucleosides, wherein the gap segment is positioned immediately adjacent to and between the 5' wing segment and the 3' wing segment, wherein each nucleoside of each wing segment comprises a 2'-O-methyoxyethyl sugar, wherein each cytosine is a 5-methylcytosine, and wherein each internucleoside linkage is a phosphorothioate linkage. ISIS 304801 has been shown to be potent in inhibiting ApoC-III and tolerable when administered to subjects.

Many of the patients recruited for this study have been diagnosed with Fredrickson Type I dyslipidemia, FCS, LPLD. Fredrickson Type I, FCS, LPLD, patients with a history of TG level ≥880 mg/dL, fasting TG level ≥750 mg/dL during screening for the study and/or TG level ≥440 mg/dL after dieting but before the start of treatment are included in the study.

To enlarge the study population, some patients suffering from hyperTG but not diagnosed with Fredrickson Type I dyslipidemia, FCS, LPLD, may be screened for Fredrickson Type I dyslipidemia, FCS, LPLD. In an example, patients with hyperTG will be identified through their medical history with a TG level ≥880 mg/dL and/or by centrifugation of the lipids in their blood for fasting TG level ≥750 mg/dL. The patients with fasting TG level ≥750 mg/dL will be further screened for at least one of the following parameters to confirm the diagnosis of Fredrickson Type I dyslipidemia, FCS, LPLD:

(1) homozygous or compound heterozygous loss-of-function mutations in genes such as LPL (e.g., P207L, G188L, D9N), ApoC2, GPIHBP1, ApoC5 or LMF1 known to cause Fredrickson Type I dyslipidemia, FCS, LPLD;

(2) LPL activity ≤20% of normal; and (3) anti-LPL antibodies.

For each patient diagnosed with Fredrickson Type I dyslipidemia, FCS, LPLD, the participation period consists of a ≤8-week screening period, (which includes a 4-week tight diet control run-in qualification period), a 1-week study qualification/baseline assessment period, a 13-week treatment period, and a post-treatment evaluation period of 13 weeks, for a total of 35 weeks of study participation. Patients with a diet controlled TG level ≥440 mg/dL are included in the study. Concomitant medications and adverse events (AEs) are recorded throughout all periods of the study.

Patients are placed on a tightly controlled diet (after screening procedures are performed) for the duration of study participation. After 28 days on the controlled diet, patients have baseline measurements and are assessed for qualification of enrollment into the treatment phase of the study.

Endpoints to evaluate include: the pharmacodynamic (PD) effects of ISIS 304801 as measured by fasting lipoprotein, total ApoC-III, TG, ApoC-II (total and associated with VLDL), apolipoprotein B-100 (apoB-100 and/or apoB-48), apolipoprotein A-1 (apoA-1), apolipoprotein A-2 (apoA-2), apolipoprotein E (apoE), total cholesterol (TC), low-density lipoprotein-cholesterol (LDL-C), LDL-TG, VLDL-C, VLDL-TG, non-high-density lipoprotein-cholesterol (non-HDL-C), non-HDL-TG, HDL-C, HDL-TG, chylomicron-cholesterol (CM-C), chylomicron-triglyceride (CM-TG), free fatty acids (FFA), and glycerol levels; the post-prandial lipid, apolipoprotein and lipoprotein characteristics and kinetics, and glucose levels; and, the safety, tolerability and pharmacokinetics (PK) of ISIS 304801. Additional endpoints to be evaluated may include a decrease in CETP or an increase in ApoA1, PON1, fat clearance and triglyceride clearance, and an improvement in the ratio of HDL to TG.

Study Drug and Treatment

A solution of the Study Drug ISIS 304801 (200 mg/mL, 1.0 mL) contained in 2-mL stoppered glass vials is provided. Vials are for single-use only. ISIS 304801 solution and placebo are prepared by a pharmacist (or qualified delegate). A trained professional administers 300 mg of the Study Drug as a single SC injection in the abdomen, thigh, or outer area of the upper arm on each dosing day.

Patients receive 13 doses of the Study Drug administered by SC injection once a week for 13 weeks (Days 1, 8, 15, 22, 29, 36, 43, 50, 57, 64, 71, 78, and 85). Patients complete the treatment visits on Day 1±0 days and on Day 8, 15, 22, 29, 36, 43, 50, 57, 64, 71, 78, and 85 within ±1 day. Patients in an extensive PK group also visit the clinic on Day 2 and 86±0 days relative to Day 1 and 85, respectively, for a 24 hour blood draw. Patients complete the follow-up visits on Day 92 and 99 within ±1 day, Day 127 within ±3 days, and Day 176 within ±5 days of the scheduled visit date. Patients in the post-prandial assessment group also visit the clinic on Day 103 within ±2 days and on the day following the Day 103 visit for the 24 hour blood draw.

Preceding each visit that includes a blood draw for PD measurements (Days 8, 15, 29, 43, 57, 71, and 85), patients are provided a standardized pre-cooked meal for the dinner on the evening prior to their visit (to ensure equal moderation of fat intake, per patient and per time point) after which they remain fasted. Alcohol consumption is not allowed for 48 hrs preceding these clinic visits.

Blood is collected after fasting and/or after a meal for measurement of VLDL, ApoC-III and other PD markers on Days 8, 15, 29, 43, 57, 71, and 85 (prior to Study Drug administration).

Patients in the post-prandial assessment group consume standardized pre-cooked meals (lunches and dinners (provided) and instructions for breakfasts and snacks) for the 2 days prior to the post-prandial evaluations. On each of the post-prandial evaluation days, following the blood draws, patients consume a standardized liquid meal, which represents about a third of the daily caloric requirements, with a stable radioisotope tracer, followed by serial blood sampling. Patients receive a standardized pre-cooked meal 9 hrs after consuming the liquid meal, after which they fast until the 24 hour blood draw the following day.

In addition to trough sample collection, patients in the extensive PK assessment group undergo serial blood sampling for 24 hrs after their first (Day 1-2) and last (Day 85-86) dose of Study Drug. PK parameters such as area under the curve (AUC), trough concentration (Cmin) and others will be assessed.

Post-Treatment Evaluation Period

Patients are followed until Study Day 176. During this time, patients return to the study center for outpatient clinic visits on Study Days 92, 99, 127, and 176 (and Day 103 for patients in the post-prandial assessment group) for safety and clinical laboratory evaluations (blood draws), diet counseling and monitoring, concomitant medication usage recording, and AE event collection.

Blood samples for PK and PD analysis are collected periodically throughout the post-treatment evaluation period. Laboratory measurements of serum chemistry, urinalysis, coagulation, complement, hematology, immune function, thyroid function, and full lipid panel are performed at the various times throughout the study.

Post-prandial assessments are done in a subset of patients as described below.

Post-Prandial Meal, Sampling Schedule, and Assessment

Post-prandial assessment for lipoproteins metabolism are performed using a radiolabelled meal supplemented with a labeled tracer, 3H-palmitate (300 µCi, Perkin Elmer Inc., Woodbridge, ON, Canada), sonicated into the liquid meal. Palmitate is a fatty acid that is a common constituent of any diet. The 3H-palmitate tracer emits weak radioactivity, equivalent to an X-ray. Since dietary palmitate is incorporated into chylomicrons as they are formed in the enterocytes of the gut, this enables monitoring the appearance and clearance of newly-formed chylomicrons from circulation. The methodology to be applied for studying post-prandial kinetics of chylomicrons appearance and clearance is well-established (Mittendorfer et al. 2003, Diabetes, 52: 1641-1648; Bickerton et al. 2007; Normand-Lauziere et al. 2010, PLoS. One, 5: e10956).

A liquid meal (similar to a milkshake) containing a small amount (300 µCi) of radiolabelled fatty acids (3H-palmitate) will be provided. The liquid meal will provide about a third of the daily caloric requirements. From 1 hr prior to 9 hrs after the ingestion of the meal, a constant infusion of [U-13C]-K palmitate (0.01 µmol/kg/min in 100 ml 25% human serum albumin; Cambridge Isotopes Laboratories Inc., Andover, Mass.) and a primed (1.6 µmol/kg) continuous (0.05 µmol/kg/min) infusion of [1,1,2,3,3-2H]-glycerol (Cambridge Isotopes Laboratories Inc.) are administered as previously described (Normand-Lauziere et al. 2010, PLoS. One, 5: e10956). Plasma palmitate and glycerol appearance rates are calculated using Steele's non-steady state equation assuming a volume of distribution of 90 ml/kg and 230 ml/kg, respectively (Gastaldelli et al. 1999, J Appl. Physiol, 87: 1813-1822).

Blood samples are drawn at intervals before and after the ingestion of the radiolabelled meal on days prior to and after the Treatment phase as noted in the table below. A standardized meal is given to the participants after the 9 hr blood draw. Blood is collected in tubes containing Na2 EDTA and Orlistat (30 µg/ml, Roche, Mississauga, Canada) to prevent in vitro triacylglycerol lipolysis and separate samples will be collected in NaF tubes for plasma glucose determination.

The following are measured at each time-point:
Plasma and CM fraction levels for 3H-tracer
Plasma [U-13C]-K palmitate and [1,1,2,3,3-2H]-glycerol appearance rates
Plasma and CM fraction levels for TG, TC, and apoB
Plasma and VLDL fraction levels for apo CIII, apo CII, and apo E
Plasma levels for glucose Plasma samples may also be used for profiling of drug binding proteins, bioanalytical method validation purposes, stability and metabolite assessments, or to assess other actions of ISIS 304801 with plasma constituents.

Results

Results for three patients diagnosed with Fredrickson Type I dyslipidemia, FCS, LPLD, recruited for this study are presented below. Two patients are homozygous for the P207L null LPL gene mutation and one patient is compound heterozygous for the P207L and G188E null LPL gene mutations. All patients have LPL mass but no or extremely low levels (<5%) of LPL activity. The patients had a TG level ≥440 mg/dL after dieting but before the start of treatment. Two of the patients had confirmed past history of acute pancreatitis and one had been on gene therapy with Glybera® in December 2007.

The data for percent change in fasting ApoCIII levels is presented in the Table below. The results indicate that treatment with ISIS 304801 reduced fasting levels of ApoC-III. 'n.d.' indicates that data was not yet collected for that particular time point.

TABLE 1

Percent change in fasting ApoCIII levels

|  | Patient 1 | Patient 2 | Patient 3 |
| --- | --- | --- | --- |
| Day 1 | 0 | 0 | 0 |
| Day 8 | n.d. | −23 | −18 |
| Day 15 | n.d. | −63 | −44 |
| Day 29 | −47 | −69 | −61 |
| Day 43 | −58 | −80 | −77 |
| Day 57 | −60 | −85 | −85 |
| Day 71 | −66 | −90 | −84 |
| Day 85 | −71 | −91 | −84 |
| Day 92 | −71 | −90 | −81 |
| Day 99 | −62 | −87 | −78 |
| Day 127 | −61 | −68 | −75 |
| Day 176 | −14 | −67 | −39 |

Levels of fasting triglyceride levels were also measured. The data for percent change, as well as absolute levels, of fasting triglyceride levels, are presented in the Tables below. The results indicate that treatment with ISIS 304801 reduced fasting levels of triglycerides.

TABLE 2

Percent change in fasting triglyceride levels

|  | Patient 1 | Patient 2 | Patient 3 |
| --- | --- | --- | --- |
| Day 1 | 0 | 0 | 0 |
| Day 8 | −39 | −8 | −6 |
| Day 15 | −35 | −57 | −63 |
| Day 29 | −54 | −40 | −61 |
| Day 43 | −49 | −63 | −81 |
| Day 57 | −55 | −68 | −82 |
| Day 71 | −53 | −76 | −89 |
| Day 85 | −49 | −88 | −71 |
| Day 92 | −64 | −84 | −57 |
| Day 99 | −17 | −62 | −69 |
| Day 127 | −66 | −43 | −79 |
| Day 176 | −6 | −58 | −16 |

TABLE 3

Fasting triglyceride levels (mg/dL)

|  | Patient 1 | Patient 2 | Patient 3 |
| --- | --- | --- | --- |
| Day 1 | 1406 | 2083 | 2043 |
| Day 8 | 851 | 1918 | 1922 |
| Day 15 | 911 | 892 | 751 |
| Day 29 | 651 | 1260 | 804 |
| Day 43 | 719 | 775 | 389 |
| Day 57 | 633 | 667 | 368 |
| Day 71 | 658 | 505 | 234 |
| Day 85 | 723 | 251 | 595 |
| Day 92 | 510 | 324 | 874 |
| Day 99 | 1167 | 793 | 626 |
| Day 127 | 485 | 1197 | 429 |
| Day 176 | 1317 | 867 | 1706 |

Levels of fasting non-HDL cholesterol levels were also measured. The data for percent change, as well as absolute levels, of fasting non-HDL cholesterol levels, are presented in the Tables below. The results indicate that treatment with ISIS 304801 reduced fasting levels of non-HDL cholesterol.

TABLE 4

Percent change in fasting non-HDL cholesterol levels

|  | Patient 1 | Patient 2 | Patient 3 |
|---|---|---|---|
| Day 1 | 0 | 0 | 0 |
| Day 8 | −23 | −24 | −15 |
| Day 15 | −19 | −60 | −51 |
| Day 29 | −38 | −49 | −50 |
| Day 43 | −43 | −64 | −64 |
| Day 57 | −43 | −65 | −59 |
| Day 71 | −44 | −71 | −55 |
| Day 85 | −42 | −74 | −56 |
| Day 92 | −51 | −75 | −53 |
| Day 99 | −21 | −60 | −55 |
| Day 127 | −42 | −47 | −56 |
| Day 176 | −2 | −57 | −16 |

TABLE 5

Fasting non-HDL cholesterol levels (mg/dL)

|  | Patient 1 | Patient 2 | Patient 3 |
|---|---|---|---|
| Day 1 | 214 | 327 | 244 |
| Day 8 | 165 | 250 | 207 |
| Day 15 | 173 | 131 | 119 |
| Day 29 | 133 | 167 | 123 |
| Day 43 | 123 | 118 | 88 |
| Day 57 | 122 | 116 | 99 |
| Day 71 | 119 | 96 | 109 |
| Day 85 | 125 | 85 | 107 |
| Day 92 | 104 | 83 | 115 |
| Day 99 | 169 | 131 | 110 |
| Day 127 | 125 | 173 | 108 |
| Day 176 | 210 | 139 | 206 |

Levels of ApoB-48, a measure of chylomicrons, were also measured. The data for percent change, as well as absolute levels, of ApoB-48 levels, are presented in the Tables below. The results indicate that treatment with ISIS 304801 reduced fasting levels of ApoB-48.

TABLE 6

Percent change in ApoB-48 levels

|  | Patient 1 | Patient 2 | Patient 3 |
|---|---|---|---|
| Day 1 | 0 | 0 | 0 |
| Day 8 | 30 | 21 | 31 |
| Day 15 | 13 | −71 | −64 |
| Day 29 | −48 | −10 | −35 |
| Day 43 | −21 | −71 | −76 |

TABLE 6-continued

Percent change in ApoB-48 levels

|  | Patient 1 | Patient 2 | Patient 3 |
|---|---|---|---|
| Day 57 | −36 | −69 | −75 |
| Day 71 | −21 | −84 | −80 |
| Day 85 | 21 | −89 | −50 |
| Day 92 | −36 | −92 | −29 |
| Day 99 | 190 | −13 | −55 |
| Day 127 | −39 | 86 | −42 |
| Day 176 | 366 | −28 | 28 |

TABLE 7

ApoB-48 levels (mg/dL)

|  | Patient 1 | Patient 2 | Patient 3 |
|---|---|---|---|
| Day 1 | 1.68 | 3.40 | 2.16 |
| Day 8 | 2.19 | 4.13 | 2.82 |
| Day 15 | 1.89 | 1.00 | 0.78 |
| Day 29 | 0.87 | 3.07 | 1.40 |
| Day 43 | 1.32 | 0.99 | 0.51 |
| Day 57 | 1.07 | 1.04 | 0.55 |
| Day 71 | 1.32 | 0.53 | 0.43 |
| Day 85 | 2.03 | 0.36 | 1.07 |
| Day 92 | 1.07 | 0.28 | 1.53 |
| Day 99 | 4.87 | 2.97 | 0.98 |
| Day 127 | 1.03 | 6.34 | 1.26 |
| Day 176 | 7.83 | 2.45 | 2.77 |

The overall lipid profile in fasting FCS patients was measured at the end of treatment and compared to baseline. The data are presented in the Tables below and indicates that treatment with ISIS 304801 improved the overall lipid profile in the patients.

TABLE 8

Percent change (mean) in lipid profile

|  | % |
|---|---|
| ApoC-III | −81 |
| Triglycerides | −69 |
| HDL-C | +78 |
| VLDL ApoC-III | −80 |
| ApoB | −13 |
| Non-HDL-C | −58 |
| VLDL | −65 |
| Total cholestetol | −53 |

TABLE 9

Individual patient profile

| Lipid parameter | Patient # | Baseline (mg/dL) | End of treatment (mg/dL) | Absolute change (mg/dL) | % change | Mean % change |
|---|---|---|---|---|---|---|
| ApoC-III | 1 | 19 | 6 | −13 | −71 | −81 |
|  | 2 | 35 | 3 | −32 | −90 |  |
|  | 3 | 20 | 4 | −16 | −83 |  |
| Triglycerides | 1 | 1406 | 617 | −790 | −56 | −69 |
|  | 2 | 2083 | 288 | −1796 | −86 |  |
|  | 3 | 2043 | 735 | −1309 | −64 |  |
| VLDL ApoC-III | 1 | 12 | 5 | −8 | −64 | −80 |
|  | 2 | 33 | 3 | −30 | −92 |  |
|  | 3 | 17 | 2 | 15 | 86 |  |
| HDL-C | 1 | 16 | 24 | 8 | 50 | +78 |
|  | 2 | 8 | 21 | 13 | 163 |  |
|  | 3 | 14 | 17 | 3 | 21 |  |

TABLE 9-continued

Individual patient profile

| Lipid parameter | Patient # | Baseline (mg/dL) | End of treatment (mg/dL) | Absolute change (mg/dL) | % change | Mean % change |
|---|---|---|---|---|---|---|
| Non HDL-C | 1 | 214 | 115 | −100 | −47 | −58 |
| | 2 | 327 | 84 | −243 | −74 | |
| | 3 | 244 | 111 | −133 | −55 | |
| ApoB | 1 | 109 | 57 | −53 | −48 | −13 |
| | 2 | 65 | 68 | 3 | 5 | |
| | 3 | 114 | 120 | 6 | 5 | |

Safety Assessment

Treatment with ISIS 304801 did not have any issues of liver enzyme elevations more than three times the ULN, abnormalities in renal function, meaningful clinical changes in other laboratory values, or relates SAEs or significant AEs.

Treatment was tolerated by all the patients with no flu-like symptoms and infrequent mild site reactions, which was resolved without treatment. There were no discontinuations due to injection site reactions.

What is claimed is:

1. A method of treating or ameliorating lipoprotein lipase deficiency (LPLD) in an animal comprising administering a therapeutically effective amount of a compound comprising an ApoCIII specific inhibitor to the animal, wherein:
administering the compound reduces a triglyceride level by at least 10%, thereby treating or ameliorating LPLD.

2. The method of claim 1, wherein the ApoCIII specific inhibitor comprises a nucleic acid capable of inhibiting the expression or activity of ApoCIII.

3. The method of claim 1, wherein the ApoCIII specific inhibitor comprises an antisense compound targeting ApoCIII.

4. The method of claim 3, wherein the antisense compound comprises a modified oligonucleotide.

5. The method of claim 4, wherein the nucleobase sequence of the modified oligonucleotide is at least 80%, at least 90% or 100% complementary to a nucleobase sequence of SEQ ID NO: 1, SEQ ID NO: 2 or SEQ ID NO: 4.

6. The method of claim 3, wherein the antisense compound comprises a single-stranded modified oligonucleotide or a double-stranded modified oligonucleotide.

7. The method of claim 4, wherein the modified oligonucleotide consists of 12 to 30 linked nucleosides.

8. The method of claim 7, wherein the modified oligonucleotide consists of 20 linked nucleosides.

9. The method of claim 4, wherein the modified oligonucleotide has at least one modified internucleoside linkage, sugar moiety or nucleobase.

10. The method of claim 9, wherein the modified internucleoside linkage of the modified oligonucleotide is a phosphorothioate internucleoside linkage, the modified sugar is a bicyclic sugar or 2'-O-methoxyethyl sugar and the modified nucleobase is a 5-methylcytosine.

11. The method of claim 4, wherein the modified oligonucleotide comprises:
(a) a gap segment consisting of linked deoxynucleosides;
(b) a 5' wing segment consisting of linked nucleosides; and
(c) a 3' wing segment consisting of linked nucleosides;
wherein the gap segment is positioned immediately adjacent to and between the 5' wing segment and the 3' wing segment and wherein each nucleoside of each wing segment comprises a modified sugar.

12. The method of claim 4, wherein the modified oligonucleotide comprises:
(a) a gap segment consisting of 10 linked deoxynucleosides;
(b) a 5' wing segment consisting of 5 linked nucleosides; and
(c) a 3' wing segment consisting of 5 linked nucleosides;
wherein the gap segment is positioned immediately adjacent to and between the 5' wing segment and the 3' wing segment and wherein each nucleoside of each wing segment comprises a 2'-O-methoxyethyl sugar, wherein each cytosine is a 5-methylcytosine, and wherein each internucleoside linkage is a phosphorothioate linkage.

13. The method of claim 1, wherein the compound comprises a modified oligonucleotide having the sequence of SEQ ID NO: 3 wherein the modified oligonucleotide comprises:
(a) a gap segment consisting of 10 linked deoxynucleosides;
(a) a 5' wing segment consisting of 5 linked nucleosides; and
(b) a 3' wing segment consisting of 5 linked nucleosides;
wherein the gap segment is positioned immediately adjacent to and between the 5' wing segment and the 3' wing segment, wherein each nucleoside of each wing segment comprises a 2'-O-methoxyethyl sugar, wherein each cytosine is a 5-methylcytosine and wherein each internucleoside linkage is a phosphorothioate linkage.

14. The method of claim 1, wherein the compound is parenterally administered.

15. The method of claim 14, wherein the parenteral administration is subcutaneous administration.

16. The method of claim 1, further comprising administering a second agent.

17. The method of claim 16, wherein the second agent is selected from an ApoCIII lowering agent, cholesterol lowering agent, non-HDL lipid lowering agent, LDL lowering agent, TG lowering agent, cholesterol lowering agent, HDL raising agent, fish oil, niacin, fibrate, statin, DCCR (salt of diazoxide), glucose-lowering agent or anti-diabetic agents.

18. The method of claim 1, wherein the compound is administered as a composition further comprising a pharmaceutically acceptable carrier or diluent.

19. The method of claim 4, wherein the modified oligonucleotide has a nucleobase sequence comprising at least 8 contiguous nucleobases of SEQ ID NO: 3.

20. The method of claim 1, wherein the compound is in a salt form.

21. The method of claim 1, wherein the animal has Familial Chylomicronemia Syndrome (FCS).

22. The method of claim 1, wherein the animal has Fredrickson Type I dyslipidemia.

23. The method of claim 1, wherein the animal is a human.

* * * * *

SEQUENCE LISTING

```
<160> NUMBER OF SEQ ID NOS: 4

<210> SEQ ID NO 1
<211> LENGTH: 533
<212> TYPE: DNA
<213> ORGANISM: Homo sapiens
<220> FEATURE:
<221> NAME/KEY: CDS
<222> LOCATION: (47)..(346)

<400> SEQUENCE: 1
tgctcagttc atccctagag gcagctgctc caggaacaga ggtgcc atg cag ccc        55
                                                  Met Gln Pro
                                                    1 cgg gta ctc ctt gtt gtt gcc ctc ctg gcg ctc ctg gcc tct gcc cga      103
Arg Val Leu Leu Val Val Ala Leu Leu Ala Leu Leu Ala Ser Ala Arg
      5                  10                  15 gct tca gag gcc gag gat gcc tcc ctt ctc agc ttc atg cag ggt tac      151
Ala Ser Glu Ala Glu Asp Ala Ser Leu Leu Ser Phe Met Gln Gly Tyr
 20                  25                  30                  35 atg aag cac gcc acc aag acc gcc aag gat gca ctg agc agc gtg cag      199
Met Lys His Ala Thr Lys Thr Ala Lys Asp Ala Leu Ser Ser Val Gln
                 40                  45                  50 gag tcc cag gtg gcc cag cag gcc agg ggc tgg gtg acc gat ggc ttc      247
Glu Ser Gln Val Ala Gln Gln Ala Arg Gly Trp Val Thr Asp Gly Phe
             55                  60                  65 agt tcc ctg aaa gac tac tgg agc acc gtt aag gac aag ttc tct gag      295
Ser Ser Leu Lys Asp Tyr Trp Ser Thr Val Lys Asp Lys Phe Ser Glu
         70                  75                  80 ttc tgg gat ttg gac cct gag gtc aga cca act tca gcc gtg gct gcc      343
Phe Trp Asp Leu Asp Pro Glu Val Arg Pro Thr Ser Ala Val Ala Ala
     85                  90                  95 tga gacctcaata ccccaagtcc acctgcctat ccatcctgcg agctccttgg           396
gtcctgcaat ctccagggct gcccctgtag gttgcttaaa agggacagta ttctcagtgc    456
tctcctaccc cacctcatgc ctggccccccc tccaggcatg ctggcctccc aataaagctg    516
gacaagaagc tgctatg                                                   533

<210> SEQ ID NO 2
<211> LENGTH: 3964
<212> TYPE: DNA
```

<213> ORGANISM: Homo sapiens

<400> SEQUENCE: 2

| | |
|---|---|
| ctactccagg ctgtgttcag ggcttggggc tggtggaggg aggggcctga aattccagtg | 60 |
| tgaaaggctg agatgggccc gaggcccctg gcctatgtcc aagccatttc ccctctcacc | 120 |
| agcctctccc tggggagcca gtcagctagg aaggaatgag ggctccccag gcccaccccc | 180 |
| agttcctgag ctcatctggg ctgcagggct ggcgggacag cagcgtggac tcagtctcct | 240 |
| agggatttcc caactctccc gcccgcttgc tgcatctgga caccctgcct caggccctca | 300 |
| tctccactgg tcagcaggtg acctttgccc agcgccctgg gtcctcagtg cctgctgccc | 360 |
| tggagatgat ataaaacagg tcagaaccct cctgcctgtc tgctcagttc atccctagag | 420 |
| gcagctgctc caggtaatgc cctctgggga ggggaaagag gaggggagga ggatgaagag | 480 |
| gggcaagagg agctccctgc ccagcccagc cagcaagcct ggagaagcac ttgctagagc | 540 |
| taaggaagcc tcggagctgg acgggtgccc ccaccccctc atcataacct gaagaacatg | 600 |
| gaggcccggg aggggtgtca cttgcccaaa gctacacagg gggtggggct ggaagtggct | 660 |
| ccaagtgcag gttcccccct cattcttcag gcttagggct ggaggaagcc ttagacagcc | 720 |
| cagtcctacc ccagacaggg aaactgaggc ctggagaggg ccagaaatca cccaaagaca | 780 |
| cacagcatgt tggctggact ggacggagat cagtccagac cgcaggtgcc ttgatgttca | 840 |
| gtctggtggg ttttctgctc catcccaccc acctcccttt gggcctcgat ccctcgcccc | 900 |
| tcaccagtcc cccttctgag agcccgtatt agcagggagc cggcccctac tccttctggc | 960 |
| agacccagct aaggttctac cttaggggcc acgccacctc cccagggagg ggtccagagg | 1020 |
| catggggacc tggggtgccc ctcacaggac acttccttgc aggaacagag gtgccatgca | 1080 |
| gccccgggta ctccttgttg ttgccctcct ggcgctcctg gcctctgccc gtaagcactt | 1140 |
| ggtgggactg ggctggggc agggtggagg caacttgggg atcccagtcc caatgggtgg | 1200 |
| tcaagcagga gcccagggct cgtccagagg ccgatccacc ccactcagcc ctgctctttc | 1260 |
| ctcaggagct tcagaggccg aggatgcctc ccttctcagc ttcatgcagg gttacatgaa | 1320 |
| gcacgccacc aagaccgcca aggatgcact gagcagcgtg caggagtccc aggtggccca | 1380 |
| gcaggccagg tacacccgct ggcctccctc cccatccccc ctgccagctg cctccattcc | 1440 |
| cacccgcccc tgccctggtg agatcccaac aatggaatgg aggtgctcca gcctcccctg | 1500 |
| ggcctgtgcc tcttcagcct cctctttcct cacagggcct tgtcaggct gctgcgggag | 1560 |
| agatgacaga gttgagactg cattcctccc aggtccctcc tttctccccg gagcagtcct | 1620 |
| agggcgtgcc gttttagccc tcatttccat tttccttttcc tttcccttc tttctctttc | 1680 |
| tatttctttc tttctttctt tctttctttc tttcttcttt tctttctttc tttctttctt | 1740 |
| tctttctttc ctttctttct ttcctttctt tctttccttt ctttctttct ttcctttctt | 1800 |
| tctctttctt tctttctttc cttttctttt cttttccctct cttcctttct ctctttcttt | 1860 |
| cttcttcttt ttttttttaat ggagtctccc tctgtcacct aggctggagt gcagtggtgc | 1920 |
| catctcggct cactgcaacc tccgtctccc gggttcaacc cattctcctg cctcagcctc | 1980 |
| ccaagtagct gggattacag gcacgcgcca ccacacccag ctaattttg tattttagc | 2040 |
| agagatgggg tttcaccatg ttggccaggt tggtcttgaa ttcctgacct cagggggatcc | 2100 |
| tcctgcctcg gcctcccaaa gtgctgggat tacaggcatg agccactgcg cctggcccca | 2160 |
| ttttcctttt ctgaaggtct ggctagagca gtggtcctca gcctttttgg caccagggac | 2220 |
| cagttttgtg gtggacaatt tttccatggg ccagcgggga tggttttggg atgaagctgt | 2280 |

```
tccacctcag atcatcaggc attagattct cataaggagc cctccaccta gatccctggc    2340
atgtgcagtt cacaataggg ttcacactcc tatgagaatg taaggccact tgatctgaca    2400
ggaggcggag ctcaggcggt attgctcact cacccaccac tcacttcgtg ctgtgcagcc    2460
cggctcctaa cagtccatgg accagtacct atctatgact tgggggttgg ggaccccctgg   2520 gctaggggtt tgccttggga ggccccacct gacccaattc aagcccgtga gtgcttctgc    2580
tttgttctaa gacctggggc cagtgtgagc agaagtgtgt ccttcctctc ccatcctgcc    2640
cctgcccatc agtactctcc tctcccctac tcccttctcc acctcaccct gactggcatt    2700
agctggcata gcagaggtgt tcataaacat tcttagtccc cagaaccggc tttggggtag    2760
gtgttatttt ctcactttgc agatgagaaa attgaggctc agagcgatta ggtgacctgc    2820
cccagatcac acaactaatc aatcctccaa tgactttcca aatgagaggc tgcctccctc    2880
tgtcctaccc tgctcagagc caccaggttg tgcaactcca ggcggtgctg tttgcacaga    2940
aaacaatgac agccttgacc tttcacatct ccccaccctg tcactttgtg cctcaggccc    3000
aggggcataa acatctgagg tgacctggag atggcagggt ttgacttgtg ctggggttcc    3060
tgcaaggata tctcttctcc cagggtggca gctgtggggg attcctgcct gaggtctcag    3120
ggctgtcgtc cagtgaagtt gagagggtgg tgtggtcctg actggtgtcg tccagtgggg    3180
acatgggtgt gggtcccatg gttgcctaca gaggagttct catgccctgc tctgttgctt    3240
cccctgactg atttaggggc tgggtgaccg atggcttcag ttccctgaaa gactactgga    3300
gcaccgttaa ggacaagttc tctgagttct gggatttgga ccctgaggtc agaccaactt    3360
cagccgtggc tgcctgagac ctcaataccc caagtccacc tgcctatcca tcctgcgagc    3420
tccttgggtc ctgcaatctc cagggctgcc cctgtaggtt gcttaaaagg acagtattc    3480 tcagtgctct cctaccccac tcatgcctg gcccccctcc aggcatgctg gcctcccaat    3540
aaagctggac aagaagctgc tatgagtggg ccgtcgcaag tgtgccatct gtgtctgggc    3600
atgggaaagg gccgaggctg ttctgtgggt gggcactgga cagactccag gtcaggcagg    3660
catggaggcc agcgctctat ccaccttctg gtagctgggc agtctctggg cctcagtttc    3720
ttcatctcta aggtaggaat caccctccgt acctgccctt ccttgacagc tttgtgcgga    3780
aggtcaaaca ggacaataag tttgctgata cttgataaa ctgttaggtg ctgcacaaca    3840
tgacttgagt gtgtgcccca tgccagccac tatgcctggc acttaagttg tcatcagagt    3900
tgagactgtg tgtgtttact caaaactgtg gagctgacct cccctatcca ggcccccctag   3960 ccct                                                                  3964
```

<210> SEQ ID NO 3
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 3
agcttcttgt ccagctttat                                                 20

<210> SEQ ID NO 4
<211> LENGTH: 3958
<212> TYPE: DNA
<213> ORGANISM: Homo sapiens

<400> SEQUENCE: 4

-continued

```
ctactccagg ctgtgttcag ggcttggggc tggtggaggg aggggcctga aattccagtg      60
tgaaaggctg agatgggccc gaggcccctg gcctatgtcc aagccatttc ccctctcacc     120
agcctctccc tggggagcca gtcagctagg aaggaatgag ggctccccag gcccaccccc     180
agttcctgag ctcatctggg ctgcagggct ggcgggacag cagcgtggac tcagtctcct     240
agggatttcc caactctccc gcccgcttgc tgcatctgga caccctgcct caggccctca     300
tctccactgg tcagcaggtg acctttgccc agcgccctgg gtcctcagtg cctgctgccc     360
tggagatgat ataaaacagg tcagaaccct cctgcctgtc tgctcagttc atccctagag     420
gcagctgctc caggtaatgc cctctgggga ggggaaagag gaggggagga ggatgaagag     480
gggcaagagg agctccctgc ccagcccagc cagcaagcct ggagaagcac ttgctagagc     540
taaggaagcc tcggagctgg acgggtgccc cccacccctc atcataacct gaagaacatg     600
gaggcccggg aggggtgtca cttgcccaaa gctacatagg gggtggggct ggaagtggct     660
ccaagtgcag gttcccccct cattcttcag gcttagggct ggaggaagcc ttagacagcc     720
cagtcctacc ccagacaggg aaactgaggc ctggagaggg ccagaaatca cccaaagaca     780
cacagcatgt tggctggact ggacggagat cagtccagac cgcaggtgcc ttgatgttca     840
gtctggtggg ttttctgctc catcccaccc acctcccttt gggcctcgat ccctcgcccc     900
tcaccagtcc cccttctgag agcccgtatt gcagggagc cggcccctac tccttctggc     960
agacccagct aaggttctac cttaggggcc acgccacctc cccagggagg ggtccagagg    1020
catggggacc tggggtgccc ctcacaggac acttccttgc aggaacagag gtgccatgca    1080
gccccgggta ctccttgttg ttgccctcct ggcgctcctg gcctctgccc gtaagcactt    1140
ggtgggactg ggctggggc agggtggagg caacttgggg atcccagtcc caatgggtgg    1200
tcaagcagga gcccagggct cgtccatagg ccgatccacc ccactcagcc ctgctctttc    1260
ctcaggagct tcagaggccg aggatgcctc ccttctcagc ttcatgcagg gctacatgaa    1320
gcacgccacc aagaccgcca aggatgcact gagcagcgtg caggagtccc aggtggccca    1380
gcaggccagg tacacccgct ggcctccctc cccatccccc ctgccagctg cctccattcc    1440
cacccacccc tgccctggtg agatcccaac aatggaatgg aggtgctcca gcctcccctg    1500
ggcctgtgcc tcttcagcct cctctttcct cacagggcct tgtcaggct gctgcgggag    1560
agatgacaga gttgagactg cattcctccc aggtccctcc tttctcccca gagcagtcct    1620
agggcgcgcc gttttagccc tcatttccat tttccttttcc tttcccttc tttccctttc    1680
tatttctttc tttctttctt tctttcttt ttctttcttt tcctttcttc tttcttt     1740
tctttctttc ctttctttct ttcttttctt ctttcttttct ttcctttctt tctctttctt    1800
tctttctttc tttcctttttt ctttcttttcc ctctcttcct ttctctcttt ctttcttctt    1860
cttttttttt taatggagtc tccctctgtc acccaggctg gagtgcagtg gtgccatctc    1920
ggctcactgc aacctccgtc tcccgggttc aacccattct cctgcctcag cctcccaagt    1980
agctgggatt acaggcacgc gccaccacac ccagctaatt tttgtatttt tagcagagat    2040
ggggttcac catgttggcc aggttggtct tgaattcctg acctcagggg atcctcctgc    2100
ctcggcctcc caaagcgctg ggattacagg catgagccac tgcgcctggc cccattttcc    2160
ttttctgaag gtctggctag agcagtggtc ctcagccttt ttggcaccag gaccagttt    2220
tgtggtggac aattttttcca tgggccagcg gggatggttt tgggatgaag ctgttccacc    2280
tcagatcatc aggcattaga ttctcataag gagccctcca cctagatccc tggcatgtgc    2340
agttcacaac agggttcaca ctcctatgag aatgtaaggc cacttgatct gacaggaggc    2400
```

```
ggagctcagg cggtattgct cactcaccca ccactcactt cgtgctgtgc agcccggctc    2460
ctaacagtcc atggaccagt acctatctat gacttggggg ttggggaccc ctgggctagg    2520
ggtttgcctt gggaggcccc acctgaccta attcaagccc gtgagtgctt ctgctttgtt    2580
ctaagacctg gggccagtgt gagcagaagt gtgtccttcc tctcccatcc tgccctgcc     2640 catcagtact ctcctctccc ctactccctt ctccacctca ccctgactgg cattagctgg    2700
catagcagag gtgttcataa acattcttag tccccagaac cggctttggg gtaggtgtta    2760
ttttctcact ttgcagatga gaaaattgag gctcagagcg attaggtgac ctgccccaga    2820
tcacacaact aatcaatcct ccaatgactt tccaaatgag aggctgcctc cctctgtcct    2880
accctgctca gagccaccag gttgtgcaac tccaggcggt gctgtttgca cagaaaacaa    2940
tgacagcctt gacctttcac atctccccac cctgtcactt tgtgcctcag gcccaggggc    3000
ataaacatct gaggtgacct ggagatggca gggtttgact tgtgctgggg ttcctgcaag    3060
gatatctctt ctcccagggt ggcagctgtg ggggattcct gcctgaggtc tcagggctgt    3120
cgtccagtga agttgagagg gtggtgtggt cctgactggt gtcgtccagt ggggacatgg    3180
gtgtgggtcc catggttgcc tacagaggag ttctcatgcc ctgctctgtt gcttcccctg    3240
actgatttag gggctgggtg accgatggct tcagttccct gaaagactac tggagcaccg    3300
ttaaggacaa gttctctgag ttctgggatt tggaccctga ggtcagacca acttcagccg    3360
tggctgcctg agacctcaat accccaagtc cacctgccta tccatcctgc cagctccttg    3420
ggtcctgcaa tctccagggc tgcccctgta ggttgcttaa aagggacagt attctcagtg    3480
ctctcctacc ccacctcatg cctggccccc ctccaggcat gctggcctcc caataaagct    3540
ggacaagaag ctgctatgag tgggccgtcg caagtgtgcc atctgtgtct gggcatggga    3600
aagggccgag gctgttctgt gggtgggcac tggacagact ccaggtcagg caggcatgga    3660
ggccagcgct ctatccacct tctggtagct gggcagtctc tgggcctcag tttcttcatc    3720
tctaaggtag gaatcaccct ccgtaccctg ccttccttga cagctttgtg cggaaggtca    3780
aacaggacaa taagtttgct gatactttga taaactgtta ggtgctgcac aacatgactt    3840
gagtgtgtgc cccatgccag ccactatgcc tggcacttaa gttgtcatca gagttgagac    3900
tgtgtgtgtt tactcaaaac tgtggagctg acctccccta tccaggccac ctagccct     3958
```